United States Patent
Fukuda et al.

(10) Patent No.: US 7,560,569 B2
(45) Date of Patent: Jul. 14, 2009

(54) BICYCLOAMIDE DERIVATIVE

(75) Inventors: Yasumichi Fukuda, Tochigi (JP); Yoshikazu Asahina, Tochigi (JP); Satoru Katayama, Saitama (JP); Taku Shibue, Saitama (JP); Koji Murakami, Tochigi (JP); Tomohiro Ide, Ibaraki (JP)

(73) Assignee: Kyorin Pharmaceutical Co., Ltd, Tokyo (JP)

( * ) Notice: Subject to any disclaimer, the term of this patent is extended or adjusted under 35 U.S.C. 154(b) by 93 days.

(21) Appl. No.: 10/590,111

(22) PCT Filed: Feb. 17, 2005

(86) PCT No.: PCT/JP2005/002389

§ 371 (c)(1),
(2), (4) Date: May 14, 2007

(87) PCT Pub. No.: WO2005/077900

PCT Pub. Date: Aug. 25, 2005

(65) Prior Publication Data

US 2007/0265320 A1 Nov. 15, 2007

(30) Foreign Application Priority Data

Feb. 18, 2004 (JP) ............................. 2004-041407

(51) Int. Cl.
*C07D 277/06* (2006.01)
*C07D 263/04* (2006.01)
*C07D 207/09* (2006.01)

(52) U.S. Cl. ..................... 548/200; 548/215; 548/569

(58) Field of Classification Search .............. 548/200, 548/215, 569
See application file for complete search history.

(56) References Cited

U.S. PATENT DOCUMENTS

| | | | |
|---|---|---|---|
| 5,939,560 A | 8/1999 | Jenkins et al. | |
| 6,166,063 A | 12/2000 | Villhauer | |
| 6,201,132 B1 | 3/2001 | Jenkins et al. | |
| 6,432,969 B1 * | 8/2002 | Villhauer | 514/275 |
| 6,849,622 B2 | 2/2005 | Yasuda et al. | |
| 2001/0025023 A1 | 9/2001 | Carr | |
| 2001/0031780 A1 | 10/2001 | Kanstrup et al. | |
| 2002/0019411 A1 | 2/2002 | Robl et al. | |
| 2002/0103384 A1 | 8/2002 | Kanstrup et al. | |
| 2002/0193390 A1 | 12/2002 | Villhauer | |
| 2003/0100563 A1 | 5/2003 | Edmondson et al. | |
| 2003/0105077 A1 | 6/2003 | Kanstrup et al. | |
| 2003/0225102 A1 | 12/2003 | Sankaranarayanan | |
| 2004/0063935 A1 | 4/2004 | Yasuda et al. | |
| 2004/0072892 A1 | 4/2004 | Fukushima et al. | |
| 2004/0082607 A1 | 4/2004 | Oi et al. | |
| 2004/0106655 A1 | 6/2004 | Kitajima et al. | |
| 2004/0106802 A1 | 6/2004 | Sankaranarayanan | |
| 2004/0152745 A1 | 8/2004 | Jackson et al. | |
| 2004/0167133 A1 | 8/2004 | Edmondson et al. | |
| 2004/0167341 A1 | 8/2004 | Haffner et al. | |
| 2004/0171848 A1 | 9/2004 | Haffner et al. | |
| 2004/0176428 A1 | 9/2004 | Edmondson et al. | |
| 2004/0229926 A1 | 11/2004 | Yasuda et al. | |
| 2004/0242636 A1 | 12/2004 | Haffner et al. | |
| 2005/0054678 A1 | 3/2005 | Yasuda et al. | |
| 2005/0148606 A1 | 7/2005 | Kanstrup et al. | |
| 2005/0153973 A1 | 7/2005 | Aranyl et al. | |
| 2005/0245538 A1 | 11/2005 | Kitajima et al. | |
| 2006/0173056 A1 | 8/2006 | Kitajima et al. | |
| 2006/0241146 A1 | 10/2006 | Yasuda et al. | |
| 2006/0270679 A1 | 11/2006 | Edmondson et al. | |
| 2007/0112059 A1 | 5/2007 | Fukushima et al. | |
| 2007/0112205 A1 | 5/2007 | Fukushima et al. | |
| 2007/0167501 A1 | 7/2007 | Fukuda et al. | |

FOREIGN PATENT DOCUMENTS

| | | |
|---|---|---|
| JP | 2002-356472 | 12/2002 |
| JP | 2003-520849 | 7/2003 |
| JP | 2004-2367 | 1/2004 |
| JP | 2004-2368 | 1/2004 |
| JP | 2004-503531 | 2/2004 |
| WO | 98/19998 | 5/1998 |
| WO | 03/106456 | 12/2003 |
| WO | 2004/007446 | 1/2004 |
| WO | 2004/009544 | 1/2004 |

OTHER PUBLICATIONS

Diabetes Guide [online], [retrieved from the Internet on on Jun. 17, 2008] [URL; http://diabetes.webmd.com/guide/diabetes-overview].*
International Search Report issued Mar. 29, 2005 in the International (PCT) Application PCT/2005/002389 of which the present application is the U.S. National Stage.
International Preliminary Report on Patentability issued Sep. 19, 2006 in the International (PCT) Application PCT/2005/002389 of which the present application is the U.S. National Stage.
U.S. Appl. No. 10/588,660.

* cited by examiner

*Primary Examiner*—Rebecca L Anderson
*Assistant Examiner*—Shawquia Young
(74) *Attorney, Agent, or Firm*—Wenderoth, Lind & Ponack, L.L.P.

(57) ABSTRACT

Novel bicycloamide derivatives (general formula (1)) and pharmaceutically acceptable salts thereof effectively inhibit DPP-IV. The bicycloamide derivatives are represented by the general formula (1):

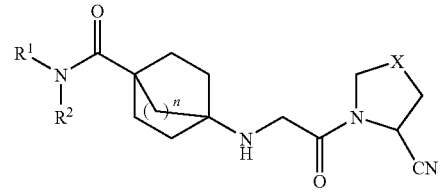

(1)

Pharmaceutically acceptable salts thereof are also included (Example: (2S,4S)-1-[[(4-carbamoylbicyclo[2.2.2]oct-1-yl)amino]acetyl]-4-fluoropyrrolidine-2-carbonitrile)).

8 Claims, 1 Drawing Sheet

BICYCLOAMIDE DERIVATIVE

TECHNICAL FIELD

The present invention relates to bicycloamide derivatives and pharmaceutically acceptable salts thereof that inhibit dipeptidylpeptidase IV (DPP-IV) and are useful in the prevention and/or treatment of type II diabetes and other diseases that involve DPP-IV.

BACKGROUND ART

Dipeptidylpeptidase IV (EC3.4.14.5, referred to as "DPP-IV" or "CD26," hereinafter) is a serine protease that specifically hydrolyzes polypeptides having proline or alanine at position 2 on the C-terminal side of these amino acid residues, cleaving dipeptides Xaa-Pro or Xaa-Ala from the N-terminus of the polypeptides (Xaa may be any amino acid).

One biological function of DPP-IV is the inactivation of glucagon-like peptide 1 (GLP-1) by cleaving the N-terminal His-Ala dipeptide of GLP-1 (Non-Patent Document 1). The GLP-1 inactivated by DPP-IV is thought to act as an antagonist on GLP-1 receptors, further decreasing the physiological activity of GLP-1 (Non-Patent Document 2). GLP-1, a peptide hormone secreted from endocrine L-cells found primarily in intestinal epithelium, is known to act on β-cells of the pancreatic Langerhans' islets in a glucose-dependent manner to promote the insulin secretion, thus decreasing the blood glucose level (Non-Patent Documents 3 and 4). Having an ability to promote insulin biosynthesis and β-cell growth, GLP-1 is an essential factor for the maintenance of β-cells (Non-Patent Documents 5 and 6). It has been reported that GLP-1 also acts to promote glucose utilization by peripheral tissue and, when intraventricularly administered, decreases food intake and motility of GI tract (Non-Patent Documents 7 through 10).

A DDP-IV inhibitor is believed to increase the GLP-1 activity by suppressing the decomposition of innate GLP-1. The increased GLP-1 activity stimulates insulin secretion and improves glucose metabolism. For this reason, DPP-IV inhibitors are expected to be useful in the prevention and/or treatment of diabetes, in particular type II diabetes (Non-Patent Documents 11 and 12). The compounds are expected to be also effective in the prevention and/or treatment of other diseases that are caused or worsened by decreased glucose metabolism (for example, diabetic complications, hyperinsulinemia, hyperglycemia, abnormal lipid metabolism and obesity).

The roles of DPP-IV in a living body other than the inactivation of GLP-1 and how the enzyme is involved in the onset of various diseases have been described in many reports as described below.

(a) DPP-IV inhibitors and their antibodies prevent the invasion of HIV into cells. Expression of CD26 is reduced in T-cells derived from patients infected with HIV-1 (Non-Patent Document 13). HIV-1 Tat protein binds to DPP-IV (Non-Patent Document 14).

(b) DPP-IV is involved in immune responses. DPP-IV inhibitors and their antibodies suppress the growth of T-cells stimulated by antigens (Non-Patent Document 15). T-cells stimulated by antigens express an increased level of DDP-IV (Non-Patent Document 16). DDP-IV is involved in the cytokine production and other functions of T-cells (Non-Patent Document 17). DDP-IV binds to adenosine deaminase (ADA) on the T-cell surface (Non-Patent Document 18).

(c) Expression of DPP-IV is increased in the skin fibroblasts of patients with rheumatoid arthritis, psoriasis, and lichen planus (Non-Patent Document 19).

(d) High DPP-IV activity is observed in patients with benign prostatic hypertrophy and in the homogenate of the prostatic tissue (Non-Patent Document 20). DPP-IV in the lung endothelium acts as an adhesive molecule for lung-metastatic breast cancer and prostatic cancer in rats (Non-Patent Document 21).

(e) The DPP-IV defective variant of F344 rats has lower blood pressure than the wild-type F344 rats. DPP-IV interacts with a protein that plays a crucial role in sodium reabsorption by the kidney (Patent Documents 1 and 2).

(f) The inhibition of DPP-IV activity offers an effective approach to the prevention and/or treatment of myelosuppressive diseases, while DPP-IV-activating agents are expected to serve as drugs to increase the white blood cell count and/or treat infectious diseases (Patent Document 3).

These observations indicate that DPP-IV inhibitors can be useful in the prevention and/or treatment of diabetes (in particular, type II diabetes) and/or diseases other than diabetic complications that involve DPP-IV. For example, DPP-IV inhibitors are expected to be useful in the prevention and/or treatment of AIDS following infection with HIV, rejection following organ/tissue transplantation, multiple sclerosis, rheumatoid arthritis, inflammation, allergies, osteoporosis, psoriasis and lichen planus, benign prostatic hypertrophy, lung metastasis of breast and prostatic cancers, hypertension and infectious diseases. DPP-IV inhibitors are also expected to be used to facilitate diuresis, decrease myelosuppression and increase white blood cell count.

Among existing DPP-IV inhibitors are pyrrolidine derivatives described in Patent Documents 4 through 11, heterocyclic derivatives described in Patent Documents 12 and 13, and β-amino acid derivatives described in Patent Documents 14 and 15.

Patent Document 16, a US patent, discloses a single bicycle [2.2.2]octane derivative that inhibits DPP-IV activity. This compound, however, is completely different from the compounds of the present invention in its structure and mechanism for DPP-IV inhibition. Patent Document 17 mentions a bicycle derivative structurally similar to the compounds of the present invention. However, there is no description in this literature concerning any of the compounds of the present invention, nor have any examples been presented of the compounds.

None of the previously described DDP-IV inhibitors are practical enough in terms of DDP-IV inhibitory activity, selectivity for DPP-IV, stability, toxicity and biological kinetics. Thus, a constant need exists for effective DDP-IV inhibitors.

[Non-Patent Document 1] American Journal of Physiology, Vol. 271 (1996): ppE458-E464.

[Non-Patent Document 2] European Journal of Pharmacology, Vol. 318 (1996): pp 429-435

[Non-Patent Document 3] European Journal Clinical Investigation, Vol. 22 (1992): p154

[Non-Patent Document 4] Lancet, Vol. 2 (1987): p1300

[Non-Patent Document 5] Endocrinology, Vol. 42 (1992): p856

[Non-Patent Document 6] Diabetologia, Vol. 42 (1999): p 856

[Non-Patent Document 7] Endocrinology, Vol. 135 (1994): p2070

[Non-Patent Document 8] Diabetologia, Vol. 37 (1994): p1163

[Non-Patent Document 9] Digestion, Vol. 54 (1993): p392

[Non-Patent Document 10] Dig. Dis. Sci., Vol. 43 (1998): p1113
[Non-Patent Document 11] Diabetes, Vol. 47 (1998): pp1663-1670
[Non-Patent Document 12] Diabetologia, Vol. 42 (1999): pp1324-1331
[Non-Patent Document 13] Journal of Immunology, Vol. 149 (1992): p3037
[Non-Patent Document 14] Journal of Immunology, Vol. 150 (1993): p2544
[Non-Patent Document 15] Biological Chemistry (1991): p305
[Non-Patent Document 16] Scandinavian Journal of Immunology, Vol. 33 (1991): p737
[Non-Patent Document 17] Scandinavian Journal of Immunology, Vol. 29 (1989): p127
[Non-Patent Document 18] Science, Vol. 261 (1993): p466
[Non-Patent Document 19] Journal of Cellular Physiology, Vol. 151 (1992): p378
[Non-Patent Document 20] European Journal of Clinical Chemistry and Clinical Biochemistry, Vol. 30 (1992): p333
[Non-Patent Document 21] Journal of Cellular Physiology, Vol. 121 (1993): p1423

| [Patent Document 1] | WO 03/015775 Pamphlet |
| [Patent Document 2] | WO 03/017936 Pamphlet |
| [Patent Document 3] | WO 03/080633 Pamphlet |
| [Patent Document 4] | WO 95/15309 Pamphlet |
| [Patent Document 5] | WO 98/19998 Pamphlet |
| [Patent Document 6] | WO 00/34241 Pamphlet |
| [Patent Document 7] | WO 02/14271 Pamphlet |
| [Patent Document 8] | WO 02/30890 Pamphlet |
| [Patent Document 9] | WO 02/38541 Pamphlet |
| [Patent Document 10] | WO 03/002553 Pamphlet |
| [Patent Document 11] | US 02/0193390 Publication |
| [Patent Document 12] | WO 02/062764 Pamphlet |
| [Patent Document 13] | WO 03/004496 Pamphlet |
| [Patent Document 14] | WO 03/000180 Pamphlet |
| [Patent Document 15] | WO 03/004498 Pamphlet |
| [Patent Document 16] | US 02/0193390 Publication |
| [Patent Document 17] | WO 02/38541 Pamphlet |

DISCLOSURE OF THE INVENTION

Problems to be Solved by the Invention

It is an object of the present invention to provide a novel compound that has high DPP-IV inhibitory activity, as well as pharmaceutically acceptable salts thereof. It is another object of the present invention to provide a pharmaceutical composition containing the novel compound that has high DPP-IV inhibitory activity or a pharmaceutically acceptable salt thereof. It is still another object of the present invention to provide a prophylactic and/or therapeutic agent for diabetes and associated complications, as well as a prophylactic and/or therapeutic agent for diseases involving DPP-IV.

Means to Solve the Problems

According to the present invention, there are provided a novel bicycloamide derivative that has high DPP-IV inhibitory activity, and pharmaceutically acceptable salts thereof. Also provided is a pharmaceutical composition containing the novel bicycloamide derivative that has high DPP-IV inhibitory activity, or a pharmaceutically acceptable salt thereof. Further provided are a prophylactic and/or therapeutic agent for diabetes and associated complications, and a prophylactic and/or therapeutic agent for diseases involving DPP-IV.

Thus, the present invention concerns the following:

1) A bicycloamide derivative represented by the following general formula (1):

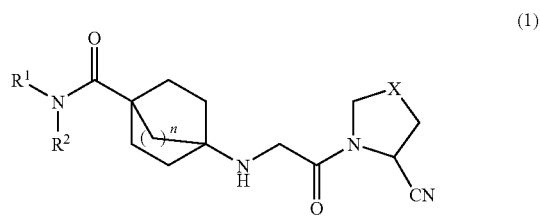

(1)

[wherein $R^1$ and $R^2$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^3R^4$ (wherein $R^3$ and $R^4$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^3$ and $R^4$ may together form a ring structure.), or $R^1$ and $R^2$ may together form a ring structure; X is $CH_2$, CHF, $CF_2$, CHOH, S or O; and n is 1, 2 or 3.], or a pharmaceutically acceptable salt thereof.

2) The bicycloamide derivative as set forth in 1) above, represented by the following general formula (2):

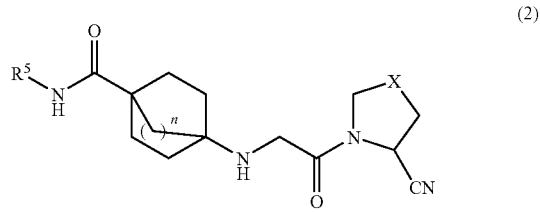

(2)

[wherein $R^5$ is a substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^3R^4$ (wherein $R^3$ and $R^4$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^3$ and $R^4$ may together form a ring structure.); X is $CH_2$, CHF, $CF_2$, CHOH, S or O; and n is 1, 2 or 3.], or a pharmaceutically acceptable salt thereof.

3) A bicycloamide derivative as set forth in 1) above, represented by the following general formula (3):

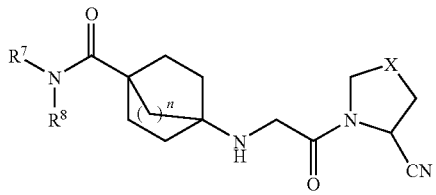

(3)

[wherein $R^7$ and $R^8$ may or may not be identical to one another and are each independently a substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^3R^4$ (wherein $R^3$ and $R^4$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^3$ and $R^4$ may together form a ring structure.), or $R^7$ and $R^8$ may together form a ring structure; X is $CH_2$, CHF, $CF_2$, CHOH, S or O; and n is 1, 2 or 3.], or a pharmaceutically acceptable salt thereof.

4) An intermediate in the production of the bicycloamide derivative of 1) above, represented by the following formula (4):

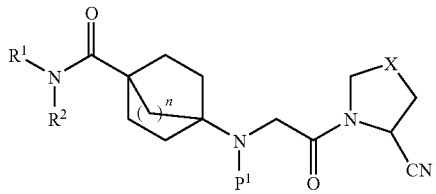

(4)

[wherein $R^1$ and $R^2$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^4R^5$ (wherein $R^4$ and $R^5$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^4$ and $R^5$ may together form a ring structure.), or $R^1$ and $R^2$ may together form a ring structure; X is $CH_2$, CHF, $CF_2$, CHOH, S or O; n is 1, 2 or 3; and $P^1$ is an amino-protecting group].

5) A pharmaceutical product, containing as an active ingredient the bicycloamide derivative as set forth in 1) above or a pharmaceutically acceptable salt thereof.

6) A DPP-IV inhibitor, containing as an active ingredient the bicycloamide derivative as set forth in 1) above or a pharmaceutically acceptable salt thereof.

7) A therapeutic agent for treating diseases involving DPP-IV, containing as an active ingredient the bicycloamide derivative as set forth in 1) above or a pharmaceutically acceptable salt thereof.

As used herein, the term "substituted or unsubstituted $C_1$ to $C_6$ alkyl group" refers to a $C_1$ to $C_6$ alkyl group (such as methyl group, cyclopropylmethyl group, ethyl group, propyl group, 1-methylethyl group, 1-methylpropyl group, 2-methylpropyl group, 1-ethylpropyl group, 2-ethylpropyl group, butyl group, t-butyl group and hexyl group) that may contain 1 to 5 substituents selected from halogen atom, hydroxy group, cyano group, $C_1$ to $C_6$ alkoxy group, substituted or unsubstituted aryloxy group, $C_1$ to $C_6$ alkylcarbonyl group, $C_1$ to $C_6$ alxoxycarbonyl group, $C_1$ to $C_6$ alkylthio group, amino group, mono- or di-substituted $C_1$ to $C_6$ alkylamino group, 4- to 9-membered cyclic amino group that may contain 1 to 3 hetero atoms, formylamino group, $C_1$ to $C_6$ alkylcarbonylamino group, $C_1$ to $C_6$ alkoxycarbonylamino group, $C_1$ to $C_6$ alkylsulfonylamino group, substituted or unsubstituted arylsulfonylamino group and other substituents.

As used herein, the term "substituted or unsubstituted $C_3$ to $C_6$ cycloalkyl group" refers to a $C_3$ to $C_6$ cycloalkyl group (such as cyclopropyl group, cyclobutyl group, cyclopentyl group and cyclohexyl group) that may contain 1 to 5 substituents selected from halogen atom, hydroxy group, cyano group, $C_1$ to $C_6$ alkoxy group, substituted or unsubstituted aryloxy group, $C_1$ to $C_6$ alkylcarbonyl group, $C_1$ to $C_6$ alxoxycarbonyl group, $C_1$ to $C_6$ alkylthio group, amino group, mono- or di-substituted $C_1$ to $C_6$ alkylamino group, 4- to 9-membered cyclic amino group that may contain 1 to 3 hetero atoms, formylamino group, $C_1$ to $C_6$ alkylcarbonylamino group, $C_1$ to $C_6$ alkoxycarbonylamino group, $C_1$ to $C_6$ alkylsulfonylamino group, substituted or unsubstituted arylsulfonylamino group and other substituents.

As used herein, the term "substituted or unsubstituted arylmethyl group" refers to an arylmethyl group (such as phenylmethyl group, naphthylmethyl group, pyridylmethyl group, quinolylmethyl group and indolylmethyl group) that may contain 1 to 5 substituents selected from halogen atom, substituted or unsubstituted $C_1$ to $C_6$ alkyl group, hydroxy group, cyano group, nitro group, substituted or unsubstituted $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted $C_1$ to $C_6$ alkylamino group, substituted or unsubstituted arylamino group, 4- to 9-membered cyclic amino group that may contain 1 to 3 hetero atoms, formylamino group, $C_1$ to $C_6$ alkylcarbonylamino group, $C_1$ to $C_6$ alkoxycarbonylamino group, $C_1$ to $C_6$ alkylsulfonylamino group, substituted or unsubstituted arylsulfonylamino group and other substituents.

As used herein, the term "substituted or unsubstituted arylethyl group" refers to an arylethyl group (such as 1-phenethyl group, 2-phenethyl group, 1-naphthylethyl group and 2-naphthylethyl group) that may contain 1 to 5 substituents selected from halogen atom, substituted or unsubstituted $C_1$ to $C_6$ alkyl group, hydroxy group, cyano group, nitro group, substituted or unsubstituted $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted $C_1$ to $C_6$ alkylamino group, substituted or unsubstituted arylamino group, 4- to 9-membered cyclic amino group that may contain 1 to 3 hetero atoms, formylamino group, $C_1$ to $C_6$ alkylcarbonylamino group, $C_1$ to $C_6$ alkoxycarbonylamino group, $C_1$ to $C_6$ alkylsulfonylamino group, substituted or unsubstituted arylsulfonylamino group and other substituents.

As used herein, the term "substituted or unsubstituted aromatic hydrocarbon group" refers to an aromatic hydrocarbon group (such as benzene ring, naphthalene ring and anthracene ring) that may contain 1 to 5 substituents selected from halogen atom, hydroxy group, cyano group, nitro group, $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 hetero atoms, formylamino group, $C_1$ to $C_6$ alkylcarbonylamino group, $C_1$ to $C_6$ alkylsulfonylamino group, substituted or unsubstituted arylsulfonylamino group and other substituents.

As used herein, the term "substituted or unsubstituted aromatic heterocyclic ring" refers to an aromatic heterocyclic ring (e.g., 5- or 6-membered aromatic monocyclic heterocyclic ring or 9- or 10-membered fused aromatic heterocyclic ring, such as pyridine ring, pyrimidine ring, pyridazine ring, triazine ring, quinoline ring, naphthyridine ring, quinazoline ring, acridine ring, pyrrole ring, furan ring, thiophene ring, imidazole ring, pyrazole ring, oxazole ring, isoxazole ring, thiazole ring, indole ring, benzofuran ring, benzothiazole ring, benzimidazole ring and benzoxazole ring. The heterocyclic ring contains 1 to 3 hetero atoms selected from nitrogen atom, oxygen atom and sulfur atom.) that may contain 1 to 5 substituents selected from halogen atom, hydroxy group, cyano group, nitro group, $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 hetero atoms, formylamino group, $C_1$ to $C_6$ alkylcarbonylamino group, $C_1$ to $C_6$ alkylsulfonylamino group, substituted or unsubstituted arylsulfonylamino group and other substituents.

As used herein, the term "substituted or unsubstituted aliphatic heterocyclic ring" refers to an aliphatic heterocyclic ring (e.g., 4- to 7-membered aliphatic monocyclic heterocyclic ring or 9- or 10-membered fused aliphatic heterocyclic ring, such as azetidine ring, pyrrolidine ring, tetrahydrofuran ring, piperidine ring, morpholine ring and piperazine ring. The heterocyclic ring contains 1 to 3 hetero atoms selected from nitrogen atom, oxygen atom and sulfur atom.) that may contain 1 to 5 substituents selected from halogen atom, substituted or unsubstituted $C_1$ to $C_6$ alkyl group, hydroxy group, cyano group, substituted or unsubstituted $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 hetero atoms, formylamino group, $C_1$ to $C_6$ alkylcarbonylamino group, $C_1$ to $C_6$ alkoxycarbonylamino group, $C_1$ to $C_6$ alkylsulfonylamino group, substituted or unsubstituted arylsulfonylamino group and other substituents.

As used herein, the term "substituted or unsubstituted alkoxy group" refers to a $C_1$ to $C_6$ alkoxy group (such as methoxy group, ethoxy group, butoxy group and hexyloxy group) that may contain 1 to 5 substituents selected from halogen atom, hydroxy group, cyano group, $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 hetero atoms, formylamino group, $C_1$ to $C_6$ alkylcarbonylamino group, $C_1$ to $C_6$ alkylsulfonylamino group, substituted or unsubstituted arylsulfonylamino group and other substituents. The term "amino-protecting group" as used herein refers to such substituents as t-butoxycarbonyl group, benzyloxycarbonyl group, allyloxycarbonyl group, methoxycarbonyl group, ethoxycarbonyl group, 2,2,2-trichloroethoxycarbonyl group, trifluoroacetyl group, acetyl group, benzyl group and 2,4,6-trimethoxybenzyl group. As used herein, the term "a ring that $R^1$ and $R^2$, $R^3$ and $R^4$, or $R^7$ and $R^8$ together form" refers to an aliphatic heterocyclic ring (e.g., 4- to 7-membered aliphatic monocyclic heterocyclic ring or 9- or 10-membered fused aliphatic heterocyclic ring, such as azetidine ring, pyrrolidine ring, piperidine ring, morpholine ring and piperazine ring. The heterocyclic ring contains 1 to 3 hetero atoms selected from nitrogen atom, oxygen atom and sulfur atom.), a benzoanalogue of aliphatic heterocyclic rings (e.g., 4- to 7-membered aliphatic monocyclic heterocyclic ring or 9- or 10-membered fused aliphatic heterocyclic ring, such as azetidine ring, pyrrolidine ring, piperidine ring, morpholine ring and piperazine ring. The heterocyclic ring contains 1 to 3 hetero atoms selected from nitrogen atom, oxygen atom and sulfur atom.), imidazole ring or benzimidazole ring. As used herein, the term "halogen atom" refers to fluorine atom, chlorine atom, bromine atom or iodine atom.

Among preferred examples of the compound of the present invention are (2S,4S)-1-[[N-(4-carbamoylbicyclo[2.2.2]oct-1-yl)amino]acetyl]-4-fluoropyrrolidine-2-carbonitrile and (2S)-1-[[N-(4-carbamoylbicyclo[2.2.2]oct-1-yl)amino]acetyl]pyrrolidine-2-carbonitrile.

ADVANTAGE OF THE INVENTION

The present invention provides novel DPP-IV inhibitors that are useful not only in the prevention and/or treatment of diabetes and associated complications, but also in the prevention and/or treatment of other diseases involving DPP-IV.

BEST MODE FOR CARRYING OUT THE INVENTION

Figure 1:
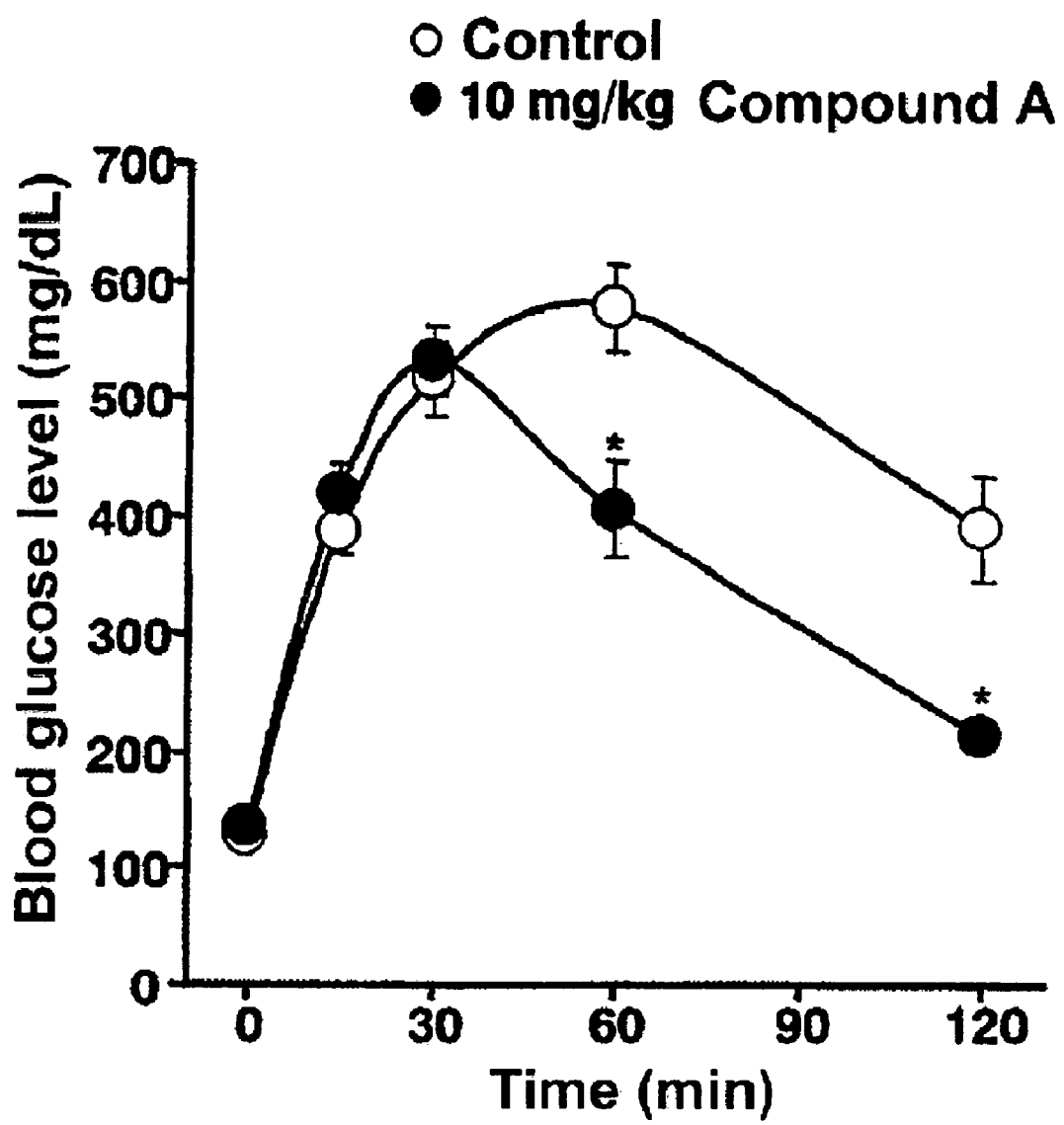
FIG. 1 is a graph showing the effect of Compound 1 on the plasma glucose level in normal mice, as determined in the oral glucose tolerance test. Each plot is given as the average of five examples± standard deviation (T-test with P<0.05 vs control).

When the compounds of the present invention form pharmaceutically acceptable salts, they may form salts with inorganic acids, such as hydrochloric acid, hydrobromic acid, sulfuric acid, nitric acid and phosphoric acid; organic acids, such as acetic acid, maleic acid, fumaric acid, succinic acid, lactic acid, malic acid, tartaric acid, citric acid, methanesulfonic acid, p-toluenesulfonic acid, benzenesulfonic acid, salicylic acid, stearic acid, palmitic acid and trifluoroacetic acid; metals, such as sodium, potassium, calcium, magnesium, aluminum and zinc; ammoniums, such as ammonium and tetramethylammonium; organic amines, such as morpholine and piperidine; and amino acids, such as glycine, lysine, arginine, phenylalanine, and proline.

The compounds of the present invention represented by the general formula (1) or salts thereof may contain a single or two or more chiral centers and thus have multiple optical isomers resulting from these chiral centers. Any of these optical isomers and diastereomers are encompassed by the present invention, as are any mixtures thereof in an arbitrary mixing ratio, including racemic mixtures. When the compounds of the present invention represented by the general formula (1) or salts thereof contain a double bond, they may have Z- or E-configuration and any of the mixtures of these compounds in an arbitrary mixing ratio are also encompassed by the present invention. Some of the compounds of the present invention represented by the general formula (1) or salts thereof may have tautomers or rotational isomers, all of which isomers are encompassed by the present invention, as are any of the mixtures thereof in an arbitrary mixing ratio.

The compounds of the present invention represented by the general formula (1) or salts thereof include intramolecular salts, addition products, solvates, and hydrates thereof.

The compounds of the present invention represented by the general formula (1) or salts thereof may be used as a pharmaceutical composition either individually or in conjunction with one or more pharmaceutically acceptable auxiliary agents: They may be formulated with pharmaceutically acceptable carriers or excipients (such as starch, lactose, calcium phosphate, and calcium carbonate), lubricants (such as magnesium stearate, calcium stearate talc, and stearic acid), binders (such as starch, crystalline cellulose, carboxy methyl cellulose, gum arabic, polyvinyl pyrrolidone, and alginic acid), disintegrating agents (such as talc and carboxy methyl cellulose calcium) or diluents (such as saline, aqueous solutions of glucose, mannitol or lactose). Using ordinary techniques, the compounds of the present invention represented by the general formula (1) or salts thereof may be formulated into tablets, capsules, granules, powders, subtle granules, ampoules, or injections for oral or parenteral administration. The compounds of the present invention represented by the general formula (1) or salts thereof are generally administered to humans and other mammals at a dose of 0.0001 to 1000 mg/kg/day while the dose may vary depending on the type of the compound or salt, route of administration, and the age, body weight, and symptoms of the subjects. The compounds of the present invention or salts thereof may be administered in a single daily dose or multiple doses per day.

When necessary, the compounds of the present invention represented by the general formula (1) or salts thereof may be used in conjunction with one or more diabetic therapeutic agents other than DPP-IV inhibitors. Among such diabetic therapeutic agents for use with the compounds of the present invention or salts thereof are insulin and its derivatives, GLP-1 and its derivatives, and other oral diabetic therapeutic agents. Examples of the oral diabetic therapeutic agents include sulfonyl urea diabetic therapeutic agents, non-sulfonylurea insulin secretagogues, biguanide diabetic therapeutic agents, α-glycosidase inhibitors, glucagon antagonists, GLP-1 agonists, PPAR agonists, β3 agonists, SGLT inhibitors, PKC inhibitors, glucagon synthase kinase 3 (GSK-3) inhibitors, protein tyrosine phosphatase 1B (PTP-1B) inhibitors, potassium channel openers, insulin sensitizers, glucose uptake modulators, compounds modifying lipid metabolism, and appetite suppressors.

Examples of GLP-1 and its derivatives include betatropin and NN-2211. Examples of sulfonylurea diabetic therapeutic agents include tolbutamide, glibenclamide, gliclazide, glimepiride, and glipizide. Examples of non-sulfonylurea insulin secretagogues include nateglinide, repaglinide, mitiglinide, and JTT-608. Examples of biguanide diabetic therapeutic agents include metformin. Examples of α-glycosidase inhibitors include voglibose and miglitol. Examples of PPAR agonists include troglitazone, rosiglitazone, pioglitazone, ciglitizone, KRP-297 (MK-767), isaglitazone, GI-262570, and JTT-501. Examples of β3 agonists include AJ-9677, YM-178, and N-5984.

The compounds (1) of the present invention can be produced by various synthetic techniques. The compounds (1) of the present invention can be isolated or purified by common separation means (such as extraction, recrystallization, distillation, and chromatography). The compounds may be obtained in the form of various salts by using common techniques or similar techniques (such as neutralization).

Representative processes for producing the compounds of the present invention and salts thereof will now be described.

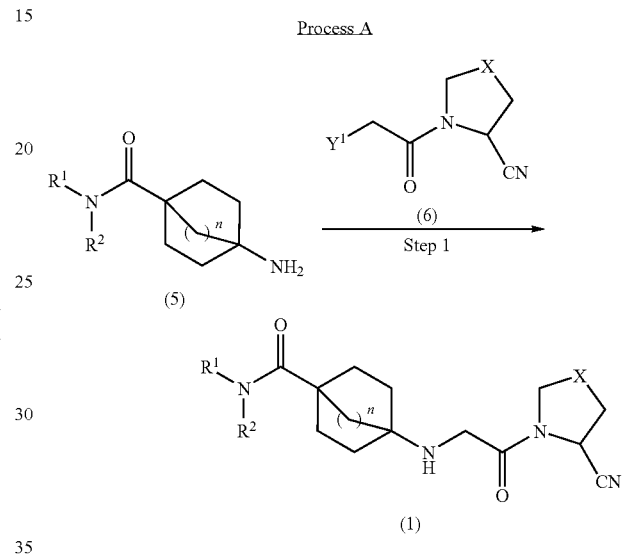

Step 1 (Process A)

In this step, a haloacetic acid derivative of the general formula (6) (where $Y^1$ is Cl or Br, and X is as defined above.) is reacted with a bicycloamine derivative of the general formula (5) (where $R^1$, $R^2$ and n are as defined above.) to obtain a bicycloamide derivative of claim 1 (where $R^1$, n and X are as defined above.). The reaction is carried out in the presence or absence of a base. Examples of the base for use in this reaction may include an inorganic base, such as sodium hydroxide, potassium hydroxide, sodium bicarbonate, potassium bicarbonate, sodium carbonate, potassium carbonate and cesium carbonate, or an organic base, such as triethylamine, diisopropyl ethylamine, N,N,N,N-tetramethyl ethylenediamine, diazabicyclo[5.4.0]-7-undecene, diazabicyclo[4.3.0]-5-nonene, phosphazene base and pentaisopropylguanidine. Examples of the catalyst for use in this reaction may include a phase transfer catalyst or an inorganic salt, such as tetrabutyl ammonium bromide, tetrabutyl ammonium iodide, benzyl triethyl ammonium bromide, lithium bromide, lithium iodide, sodium iodide, potassium bromide, potassium iodide, cesium bromide and cesium iodide. The solvent for use in the reaction may be an inert solvent that does not affect the reaction, including, for example, acetone, ethanol, toluene, acetonitrile, tetrahydrofuran, dioxane, ethylether, t-butyl methyl ether, dimethoxy ethane, ethyl acetate, dichloro methane, N,N-dimethyl formamide, dimethyl sulfoxide and N-methyl-2-pyrrolidone. This reaction proceeds smoothly at 0 to 150° C.

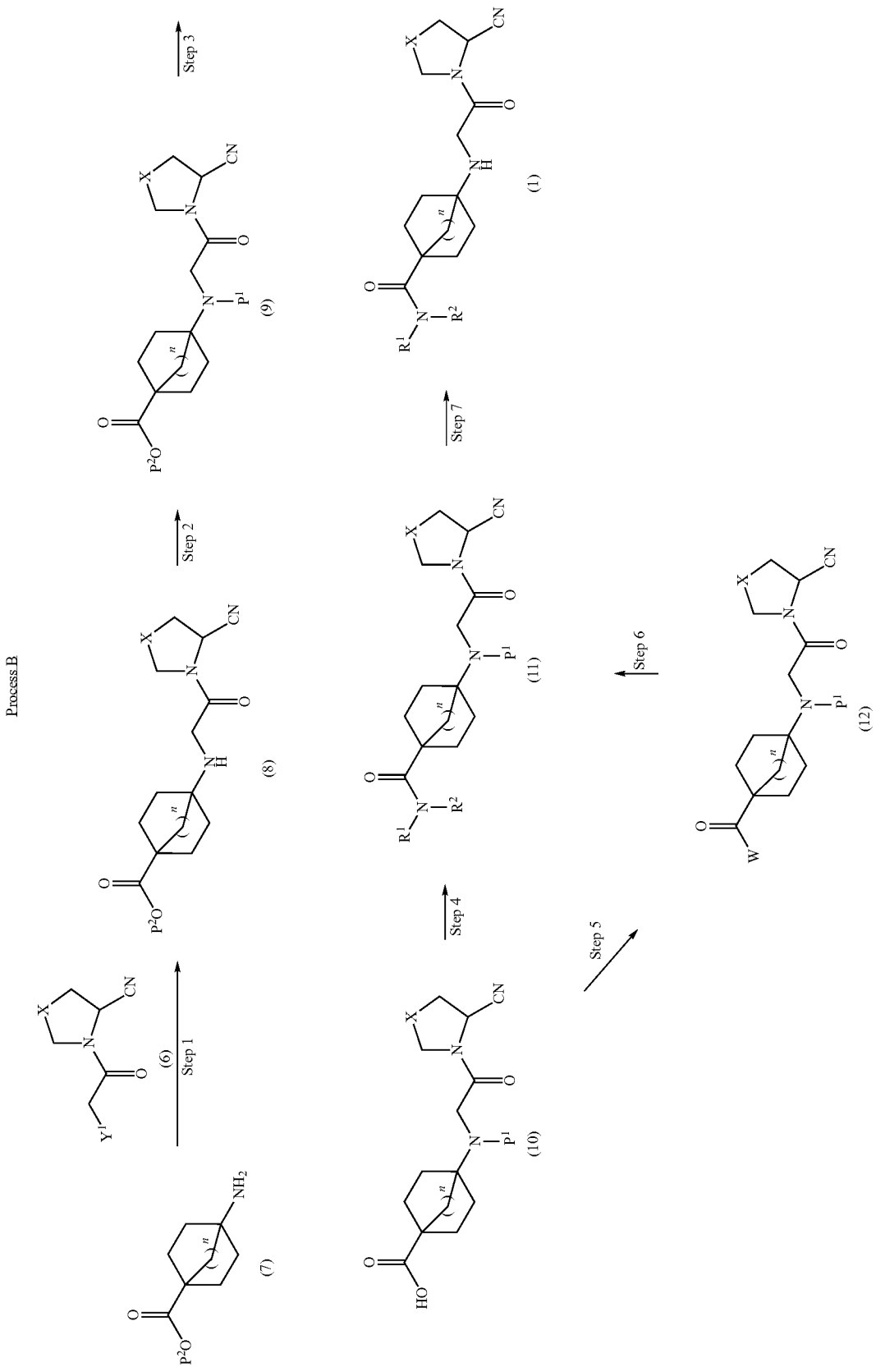

Step 1 (Process B)

In this step, a haloacetic acid derivative of the general formula (6) (where X and $Y^1$ are as defined above.) is reacted with a bicycloamine derivative of the general formula (7) (where $P^2$ is a protective group for a carboxyl group, and n is as defined above.) to obtain a bicycloamide derivative of the general formula (8) as set forth in claim 1 (where $P^2$, n, and X are as defined above.). The reaction is carried out in the presence or absence of a base. Examples of the base for use in this reaction may include an inorganic base, such as sodium hydroxide, potassium hydroxide, sodium bicarbonate, potassium bicarbonate, sodium carbonate, potassium carbonate and cesium carbonate, or an organic base, such as triethylamine, diisopropyl ethylamine, N,N,N,N-tetramethyl ethylenediamine, diazabicyclo[5.4.0]-7-undecene, diazabicyclo[4.3.0]-5-nonene, phosphazene base and pentaisopropylguanidine. Examples of the catalyst for use in the reaction may include a phase transfer catalyst or an inorganic salt, such as tetrabutyl ammonium bromide, tetrabutyl ammonium iodide, benzyl triethyl ammonium bromide, lithium bromide, lithium iodide, sodium iodide, potassium bromide, potassium iodide, cesium bromide and cesium iodide. The solvent for use in the reaction may be an inert solvent that does not affect the reaction, including, for example, as acetone, ethanol, toluene, acetonitrile, tetrahydrofuran, dioxane, ethylether, t-butyl methyl ether, dimethoxy ethane, ethyl acetate, dichloro methane, N,N-dimethyl formamide, dimethyl sulfoxide and N-methyl-2-pyrrolidone. This reaction proceeds smoothly at 0 to 150° C.

Step 2 (Process B)

In this step, the secondary amino group of the bicycloamide derivative of the general formula (8) (where $P^2$, n and X are as defined above.) is protected to give a bicycloamide derivative of the general formula (9) as set forth in claim 1 (where $P^1$ is a protective group for amino group, and $P^2$, n and x are as defined above.). The protective group $P^1$ for the secondary amine group may be t-butoxycarbonyl group, benzyloxycarbonyl group or trifluoroacetyl group. The protective groups can be introduced by known techniques. For example, when $P^1$ is t-butoxycarbonyl group, it can be readily introduced by reacting di-t-butyldicarbonate with the bicycloamide derivative of the general formula (8) (where $P^2$, n and X are as defined above.) in the presence or absence of triethylamine or N,N-dimethylaminopyridine. When $P^1$ is benzyloxycarbonyl group, it can be readily introduced by reacting benzyloxycarbonyl chloride with the bicycloamide derivative of the general formula (8) (where $P^2$, n and X are as defined above.) in the presence of triethylamine, diisopropyl ethylamine or potassium carbonate. When $P^1$ is trifluoroacetyl group, it can be readily introduced by reacting trifluoroacetic acid anhydride with the bicycloamide derivative of the general formula (8) (where $P^2$, n and X are as defined above.) in the presence of triethylamine or 4-dimethylaminopyridine.

Step 3 (Process B)

In this step, the $P^2$ group that protects the carboxyl group of the bicycloamide derivative of the general formula (9) (where $P^2$, $P^1$, n and X are as defined above.) is removed to give a bicycloamide derivative of the general formula (10) as set forth in claim 1 (where $P^1$, n and X are as defined above.) $P^2$ can be removed by known techniques. When $P^2$ is t-butyl group, it can be readily removed by using trifluoroacetic acid or a solution of hydrogen chloride/dioxane. When $P^2$ is benzyl group, it can be readily removed by using palladium carbon in combination with hydrogen or ammonium formate. When $P^2$ is tetrahydropyranyl group, it can be readily removed by using acetic acid, p-toluenesulfonic acid or hydrochloric acid.

Step 4 (Process B)

In this step, the bicycloamide derivative of the general formula (10) (where $P^1$, n and X are as defined above.) and an amine derivative of the formula $R^1R^2NH$ (where $R^1$ and $R^2$ are as defined above) are reacted in the presence of a condensation agent for amidation to give a bicycloamide derivative of the general formula (11) as set forth in claim 4 (where $R^1$, $R^2$, $P^1$, n and X are as defined above.). Examples of the condensation agents used in this step include dicyclohexylcarbodiimide (DCC), 1-(3-dimethylaminopropyl)-3-ethylcarbodiimide hydrochloride (EDCI), dimethylimidazolinium chloride (DMC), ethyl chloroformate, isobutyl chloroformate and pivaloyl chloride. These agents may be added in the form of solid, liquid or a solution in a proper solvent. Examples of the base for use in the condensation reaction may include an alkali carbonate, such as sodium bicarbonate and potassium carbonate, and a tertiary amine, such as triethylamine, diisopropyl ethylamine, N-methylmorpholine, diazabicyclo[5.4.0]-7-undecene, pyridine, 4-dimethylaminopyridine and 1,8-bis(dimethylamino)naphthalene. The solvent for use in the condensation reaction may be an inert solvent that does not affect the reaction, including, for example, N,N-dimethylformamide, N,N-dimethylacetamide, dimethyl sulfoxide, acetonitrile, tetrahydrofuran, dioxane, ethyl ether, dimethoxyethane, ethyl acetate, toluene and dichloromethane. This condensation reaction proceeds smoothly at −20 to 150° C.

Step 5 (Process B)

In this step, the bicycloamide derivative of the general formula (10) (where $P^1$, n and X are as defined above.) is converted to a bicyclic derivative of the general formula (12) [where W is a reaction residue (such as halogen atoms, and halides, imidazolides and active esters of carboxylic acids, such as 1-imidazolyl group, 4-nitrophenoxy group, pentafluorophenoxy group, imidoyloxy succinate group and 1-benzotriazolyloxy group (or 1-benzotriazolyl 3-oxide group), $P^1$, n and X are as described above.]. This step can be readily carried out by known techniques. When W is imidoyloxy succinate group, the bicycloamide derivative of the general formula (10) (where $P^1$, n and X are as defined above.) is reacted with N-hydroxysuccinic acid in the presence of a condensation agent to give the desired product. When W is benzotriazolyloxy group (or 1-benzotriazolyl 3-oxide group), the bicycloamide derivative of the general formula (10) (where $P^1$, n and X are as defined above.) is reacted with 1-hydroxybenzotriazole in the presence of a condensation agent to give the desired product. Examples of the condensation agent for use in this step include dicyclohexylcarbodiimide (DCC), 1-(3-dimethylaminopropyl)-3-ethylcarbodiimide hydrochloride (EDCI), dimethylimidazolinium chloride (DMC), ethyl chloroformate, isobutyl chloroformate and pivaloyl chloride. These agents may be added in the form of solid, liquid or a solution in a proper solvent. When it is desired to use a base in the condensation reaction, examples of the base include an alkali carbonate, such as sodium bicarbonate and potassium carbonate, and a tertiary amine, such as triethylamine, diisopropyl ethylamine, N-methylmorpholine, diazabicyclo[5.4.0]-7-undecene, pyridine, 4-dimethylaminopyridine and 1,8-bis(dimethylamino)naphthalene. The solvent for use in the condensation reaction may be an inert solvent that does not affect the condensation reaction, including, for example, N,N-dimethylformamide, N,N-dimethylacetamide, dimethylsulfoxide, acetonitrile, tetrahydrofuran, dioxane, ethyl ether, dimethoxyethane, ethyl acetate, toluene and dichloromethane. This condensation reaction proceeds smoothly at −20 to 150° C. The resulting bicyclic derivative of the general formula (12) (where W, $P^1$, n and X are as described above.) may be used in the subsequent step after purification or as the unpurified crude product.

Step 6 (Process B)

In this step, the bicycloamide derivative of the general formula (12) (where W, $P^1$, n and X are as described above.) is reacted with an amine derivative of the formula $R^1R^2NH$ (where $R^1$ and $R^2$ are as defined above.) to give a bicycloamide derivative of the general formula (11) as set forth in claim 4 (where $R^1$, $R^2$, $P^1$, n and X are as defined above.). When a base is used in the reaction, the base may be an inorganic salt, such as sodium hydroxide, potassium hydroxide, sodium bicarbonate, potassium bicarbonate, sodium carbonate, potassium carbonate and cesium carbonate, or an organic base, such as triethylamine, diisopropyl ethylamine, N,N,N,N-tetramethylethylenediamine, diazabicyclo[5.4.0]-7-undecene, diazabicyclo[4.3.0]-5-nonene, phosphazine base and pentaisopropylguanidine. The solvent for use in the reaction may be an inert solvent that does not affect the reaction, such as toluene, acetonitrile, tetrahydrofuran, dioxane, ethylether, t-butylmethylether, dimethoxyethane, ethyl acetate, dichloromethane, N,N-dimethylformamide, dimethylsulfoxide and N-methyl-2-pyrrolidone. This reaction proceeds smoothly at −30 to 150° C.

Step 7 (Process B)

In this step, the $P^1$ group that protects the secondary amino group in the bicycloamide derivative of the general formula (11) (where $R^1$, $R^2$, $P^1$, n and X are as defined above.) is removed to give a bicycloamide derivative of the general formula (1) as set forth in claim 1 (where $R^1$, $R^2$, n and X are as defined above). $P^1$ can be removed by known techniques. For example, when $P^1$ is t-butoxycarbonyl group, it can be readily removed by using trifluoroacetic acid or a solution of hydrogen chloride/dioxane. When $P^1$ is benzyloxycarbonyl group, it can be readily removed by using palladium carbon in combination with hydrogen or ammonium formate. When $P^1$ is trifluoroacetyl group, it can be readily removed by using an ammonia/methanol solution.

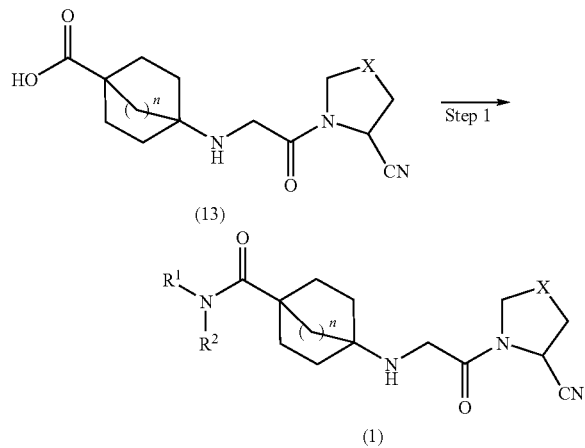

Step 1 (Process C)

In this step, the bicycloamide derivative of the general formula (13) (where n and X are as defined above.) and an amine derivative of the formula $R^1R^2NH$ (where $R^1$ and $R^2$ are as defined above) are reacted in the presence of a condensation agent for amidation to give a bicycloamide derivative of the general formula (1) as set forth in claim 1 (where $R^1$, $R^2$, $P^1$, n and X are as defined above.). Examples of the condensation agent used in this step include dicyclohexylcarbodiimide (DCC), 1-(3-dimethylaminopropyl)-3-ethylcarbodiimide hydrochloride (EDCI), dimethylimidazolinium chloride (DMC), ethyl chloroformate, isobutyl chloroformate and pivaloyl chloride. These agents may be added in the form of solid, liquid or a solution in a proper solvent. When it is desired to use a base in the condensation reaction, the base may be an alkali carbonate, such as sodium bicarbonate and potassium carbonate, or a tertiary amine, such as triethylamine, diisopropyl ethylamine, N-methylmorpholine, diazabicyclo[5.4.0]-7-undecene, pyridine, 4-dimethylaminopyridine and 1,8-bis(dimethylamino)naphthalene. The solvent for use in the condensation reaction may be an inert solvent that does not affect the reaction, such as N,N-dimethylformamide, N,N-dimethylacetamide, dimethylsulfoxide, acetonitrile, tetrahydrofuran, dioxane, ethyl ether, dimethoxyethane, ethyl acetate, toluene and dichloromethane. This condensation reaction proceeds smoothly at −20 to 150° C. Alternatively, the condensation reaction may be carried out via an active ester or acid chloride having 1-imidazolyl group, 4-nitrophenoxy group, pentafluorophenoxy group, imidoyloxy succinate group or 1-benzotriazolyloxy group (or 1-benzotriazolyl 3-oxide group). In such a case, the active ester or acid chloride may be used in the subsequent step after purification or as the unpurified crude product.

The advantageous features of the present invention will now be described with reference to experiments and examples, which are not intended to limit the scope of the invention in any way.

REFERENCE EXAMPLE 1

Synthesis of 2-tetrahydropyranyl 4-aminobicyclo[2.2.2]octane-1-carboxylate

Step 1:

Synthesis of methyl 4-benzyloxycarbonylaminobicyclo[2.2.2]octane-1-carboxylate

Methyl hydrogen bicyclo[2.2.2]octane-1,4-dicarboxylate (25.0 g), diphenylphosphoryl azide (32.5 g), triethylamine (17.3 mL) and toluene (500 mL) were mixed together. The mixture was stirred for 2 hours at room temperature and was refluxed for 2 hours. To the resulting mixture, benzylalcohol (122 mL) was added and the mixture was further refluxed for 17 hours. Subsequently, the mixture was allowed to cool and was sequentially washed with a 10% aqueous citric acid, saturated aqueous solution of sodium bicarbonate and saturated brine. The mixture was then dried over anhydrous sodium sulfate and concentrated under reduced pressure. The residue was purified by silica gel column chromatography (eluant:hexane:ethyl acetate=2:1) to give methyl 4-benzyloxycarbonylaminobicyclo[2.2.2]octane-1-carboxylate (32.2 g).

MS (FAB$^+$) m/z: 318 (MH$^+$).

Step 2:

Synthesis of 4-benzyloxycarbonylaminobicyclo[2.2.2]octane-1-carboxylic acid

Methyl 4-benzyloxycarbonylaminobicyclo[2.2.2]octane-1-carboxylate (64.3 g) was dissolved in ethanol (1100 mL). To this solution, a 1 mol/L aqueous solution of sodium hydroxide (1000 mL) was added and the mixture was stirred at 50° C. for 1 hour Ethanol in the mixture was evaporated under reduced pressure and the residue washed with diethylether (500 mL), followed by addition of concentrated hydrochloric acid to adjust the pH to 1. The resulting crystals were filtered, washed with water, dried under reduced pressure to give 4-benzyloxycarbonylaminobicyclo[2.2.2]octane-1-carboxylic acid (56.1 g).
MS (FAB$^+$) m/z: 304 (MH$^+$).

Step 3:

Synthesis of ethyl 4-benzyloxycarbonylaminobicyclo[2.2.2]octane-1-carboxylate

4-Benzyloxycarbonylaminobicyclo[2.2.2]octane-1-carboxylic acid (1.00 g) was dissolved in dichloromethane (10 mL). To this solution, 3,4-dihydro-2H-pyran (1.20 mL) and p-toluenesulfonic monohydrate (6.3 mg) were sequentially added and the mixture was stirred at room temperature for 30 minutes. The reaction mixture was sequentially washed with a saturated aqueous solution of sodium bicarbonate and saturated brine. The mixture was then dried over anhydrous sodium sulfate and concentrated under reduced pressure. The residue was purified by silica gel column chromatography (eluant:hexane:ethyl acetate=4:1) to give 2-tetrahydropyranyl 4-benzyloxycarbonylaminobicyclo[2.2.2]octane-1-carboxylate (1.18 g).
$^1$H NMR (CDCl$_3$) δ 1.53-1.95 (m, 18H), 3.67-3.71 (m, 1H), 3.82-3.89 (m, 1H), 4.59 (br, 1H), 5.03 (s, 2H), 5.95 (br, 1H), 7.29-7.38 (m, 5H).

Step 4:

Synthesis of 2-tetrahydropyranyl 4-aminobicyclo[2.2.2]octane-1-carboxylate

2-Tetrahydropyranyl 4-benzyloxycarbonylaminobicyclo[2.2.2]octane-1-carboxylate (548 mg) was dissolved in ethanol (6 mL). To this solution, 10% palladium-carbon (60 mg) was added and the mixture was stirred at room temperature for 2 hours in a stream of hydrogen. The catalyst in the reaction mixture was filtered through a Celite pad and the filtered catalyst, together with the Celite pad, washed with ethanol. The filtrate and the washings were combined and concentrated under reduced pressure. The resulting residue was dried under reduced pressure to give 2-tetrahydropyranyl 4-aminobicyclo[2.2.2]octane-1-carboxylate (357 mg).
MS (EI$^+$) m/z: 253 (M$^+$).

REFERENCE EXAMPLE 2

Synthesis of 4-aminobicyclo[2.2.2]octane-1-carboxamide

Step 1:

Synthesis of 4-benzyloxycarbonylaminobicyclo[2.2.2]octane-1-carboxamide

4-Benzyloxycarbonylaminobicyclo[2.2.2]octane-1-carboxylic acid (998 mg) was suspended in acetonitrile (20 mL). While the suspension was chilled in an ice bath, N-hydroxybenzotriazole (605 mg) and 1-ethyl-3-(3-dimethylaminopropyl)carbodiimide hydrochloride (757 mg) were sequentially added. The mixture was stirred at room temperature for 4 hours and was left overnight. Subsequently, 25% aqueous ammonia (1.80 mL) was added while the reaction vessel was chilled in an ice bath. The mixture was then stirred at room temperature for 1 hour. The insoluble material was filtered and washed sequentially with acetonitrile and dichloromethane. The filtrate and the washings were combined and concentrated under reduced pressure. The resulting residue was purified by silica gel chromatography (eluant:ethyl acetate) to give 4-benzyloxycarbonylaminobicyclo[2.2.2]octane-1-carboxamide (889 mg).
MS (EI$^+$) m/z: 302 (M$^+$).

Step 2:

Synthesis of 4-aminobicyclo[2.2.2]octane-1-carboxamide

Using 4-benzyloxycarbonylaminobicyclo[2.2.2]octane-1-carboxamide (367 mg), the same procedure was followed as in Step 4 of Reference Example 1 to give 4-aminobicyclo[2.2.2]octane-1-carboxamide (198 mg).
MS (EI$^+$) m/z: 168 (M$^+$).

REFERENCE EXAMPLE 3

Synthesis of (2S,4S)-1-[[N-benzyloxycarbonyl-N-(4-carboxybicyclo[2.2.2]oct-1-yl)amino]acetyl]-4-fluoropyrrolidine-2-carbonitrile Step 1:

Synthesis of (2S,4S)-1-[[N-[4-(2-tetrahydropyranyl)oxycarbonylbicyclo[2.2.2]oct-1-yl]amino]acetyl]-4-fluoropyrrolidine-2-carbonitrile 2-Tetrahydropyranyl 4-aminobicyclo[2.2.2]octane-1-carboxylate (62.9 mg) was suspended in acetonitrile (1 mL). To this solution, diisopropylethylamine (47 μL) was added and (2S,4S)-1-(2-bromoacetyl)-4-fluoropyrrolidine-2-carbonitrile (53.1 mg) in acetonitrile (0.8 mL) was added while the mixture was chilled in an ice bath. The mixture was stirred for 4 hours and concentrated. To the resulting residue, ethyl acetate and water were added, followed by an aqueous sodium bicarbonate solution to make the pH basic. The solution was extracted with ethyl acetate. The ethyl acetate layer was washed with saturated brine, dried over anhydrous sodium sulfate and concentrated under reduced pressure. The resulting residue was purified by silica gel chromatography (eluant:dichloromethane:methanol=10:1) to give (2S,4S)-1-[[N-[4-(2-tetrahydropyranyl)oxycarbonylbicyclo[2.2.2]oct-1-yl]amino]acetyl]-4-fluoropyrrolidine-2-carbonitrile (73.3 mg).
MS (FAB$^+$) m/z: 408 (MH$^+$). HRMS (FAB$^+$) for C$_{21}$H$_{31}$FN$_3$O$_4$ (MH$^+$): calcd, 408.2299; found, 408.2295.

Step 2:

Synthesis of (2S,4S)-1-[[N-benzyloxycarbonyl-N-(4-carboxybicyclo[2.2.2]oct-1-yl)amino]acetyl]-4-fluoropyrrolidine-2-carbonitrile Ethyldiisopropylamine (194 μL) and benzylchloroformate (137 μL) were added dropwise to (2S,4S)-1-[[N-[4-(2-tetrahydropyranyl)oxycarbonylbicyclo[2.2.2]oct-1-yl]amino]acetyl]-4-fluoropyrrolidine-2-carbonitrile (379 mg) in dioxane (5 mL) while the solution was cooled in water. The mixture was stirred at room temperature for 1 hour, followed by addition of 1N hydrochloric acid (0.1 mL) and stirring at room temperature for additional 1 hour. The solvent was evaporated under reduced pressure. The resulting crystal was then washed with diisopropylether and water and was dried under reduced pressure. The dried crystal was purified by silica gel chromatography (eluant:dichloromethane:methanol=10:1) to give (2S,4S)-1-[[N-benzyloxycarbonyl-N-(4-carboxybicyclo[2.2.2]oct-1-yl)amino]acetyl]-4-fluoropyrrolidine-2-carbonitrile (335 mg).

MS (FAB$^+$) m/z: 458 (MH$^+$). HRMS (FAB$^+$) for $C_{24}H_{29}FN_3O_5$ (MH$^+$): calcd, 458.2091; found, 458.2106.

REFERENCE EXAMPLE 4

Synthesis of (2S,4S)-1-(2-chloroacetyl)-4-fluoropyrrolidine-2-carbonitrile

According to the process for producing (2S,4S)-1-(2-bromoacetyl)-4-fluoropyrrolidine-2-carbonitrile described in the publication of WO 02/38541, (2S,4S)-4-fluoropyrrolidine-2-carboxamide hydrochloride (5.00 g) and chloroacetylchloride (2.60 mL) were used to give (2S,4S)-1-(2-chloroacetyl)-4-fluoropyrrolidine-2-carbonitrile (4.96 g).

MS (EI$^+$) m/z: 190 (M$^+$). HRMS (EI$^+$) for $C_7H_8ClFN_2O$ (M$^+$): calcd, 190.0309; found, 190.0283.

EXAMPLE 1

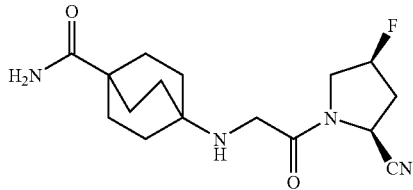

Synthesis of (2S,4S)-1-[[(4-carbamoylbicyclo[2.2.2]oct-1-yl)amino]acetyl]-4-fluoropyrrolidine-2-carbonitrile 4-Aminobicyclo[2.2.2]octane-1-carboxamide (50.0 mg) was dissolved in N,N-dimethylformamide (2 mL). To this solution, potassium carbonate (50.0 mg) was added, followed by dropwise addition of (2S,4S)-1-(2-bromoacetyl)-4-fluoropyrrolidine-2-carbonitrile (70.0 mg) in N,N-dimethylformamide (1 mL) at room temperature. The mixture was stirred at room temperature for 2.5 hours and was concentrated under reduced pressure. The resulting residue was purified by silica gel chromatography (eluant:chloroform:methanol=10:1) to give (2S,4S)-1-[[(4-carbamoylbicyclo[2.2.2]oct-1-yl)amino]acetyl]-4-fluoropyrrolidine-2-carbonitrile (94.1 mg).

MS (FAB$^+$) m/z: 323 (MH$^+$). HRMS (FAB$^+$) for $C_{16}H_{24}FN_4O_2$ (MH$^+$): calcd, 323.1883; found, 323.1903.

EXAMPLE 2

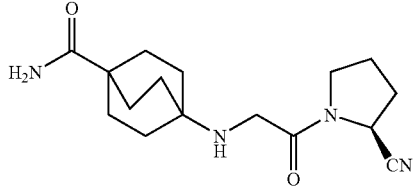

Synthesis of (2S)-1-[[(4-carbamoylbicyclo[2.2.2]oct-1-yl)amino]acetyl]pyrrolidine-2-carbonitrile Using 4-aminobicyclo[2.2.2]octane-1-carboxamide (50.0 mg) and (2S)-1-(2-bromoacetyl)pyrrolidine-2-carbonitrile (56.9 mg), the same procedure was followed as in Example 1 to give (2S)-1-[[(4-carbamoylbicyclo[2.2.2]oct-1-yl)amino]acetyl]pyrrolidine-2-carbonitrile (47.5 mg).

MS (FAB$^+$) m/z: 305 (MH$^+$). HRMS (FAB$^+$) for $C_{16}H_{25}N_4O_2$ (MH$^+$): calcd, 305.1798; found, 305.1999.

EXAMPLE 3

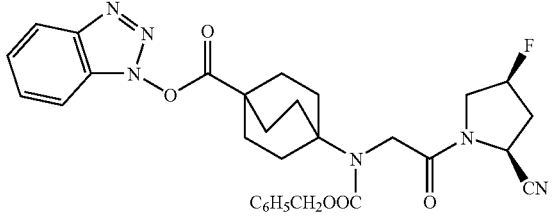

Synthesis of (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (2S,4S)-1-[[N-Benzyloxycarbonyl-N-(4-carboxybicyclo[2.2.2]oct-1-yl)amino]acetyl]-4-fluoropyrrolidine-2-carbonitrile (91.5 mg) and 1-hydroxybenzotriazole (45.9 mg) were dissolved in N,N-dimethylformamide (2.0 mL). While the solution was chilled in an ice bath, 1-(3-dimethylaminopropyl)-3-ethylcarbodiimide hydrochloride (95.9 mg) was added and the mixture was allowed to warm to room temperature and was stirred for 15 hours. The solvent was evaporated under reduced pressure and the residue was purified by silica gel chromatography (eluant:ethyl acetate) to give (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (92.0 mg).

$^1$H NMR (CDCl$_3$) δ 2.24-2.25 (m, 12H), 2.57 (t, J=15.3 Hz, 1H), 3.33-4.41 (m, 5H), 4.29-5.50 (m, 4H), 7.30-7.44 (m, 7H), 7.53 (t, J=8.0 Hz, 1H), 8.06 (d, J=8.6 Hz, 1H).

MS (FAB$^+$) m/z: 575 (MH$^+$). HRMS (FAB$^+$) for $C_{30}H_{32}FN_6O_5$ (MH$^+$): calcd, 575.2418; found, 575.2407.

EXAMPLE 4

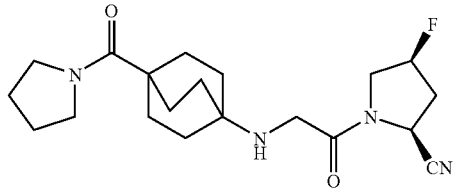

Synthesis of (2S,4S)-1-[[N-[4-(pyrrolidin-1-yl)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(pyrrolidin-1-yl)carbonylbicyclo[2.2.2]oct-1-yl]amino]acetyl]-4-fluoropyrrolidine-2-carbonitrile (2S,4S)-1-[[N-Benzyloxycarbonyl-N-[4-(benzotriazol-1-yl)oxycarbonylbicyclo[2.2.2]oct-1-yl]amino]acetyl]-4-fluoropyrrolidine-2-carbonitrile (20.0 mg) and pyrrolidine (4.4 μL) were dissolved in tetrahydrofuran (0.4 mL) and the mixture was stirred at room temperature for 25 minutes. The solvent was removed under reduced pressure and the residue was dissolved in dichloromethane. The organic layer washed sequentially with 0.1 N aqueous hydrochloric acid, saturated aqueous sodium bicarbonate solution and saturated brine. The organic layer was then dried over anhydrous sodium sulfate and was concentrated under reduced pressure. The resulting residue was purified by silica gel chromatography (eluant:ethyl acetate:methanol=20:1) to give (2S,4S)-1-[[N-benzyloxycarbonyl-N-[4-(piperidin-1-yl)carbonylbicyclo[2.2.2]oct-1-yl]amino]acetyl]-4-fluoropyrrolidine-2-carbonitrile (16.0 mg).

MS (FAB$^+$) m/z: 511 (MH$^+$). HRMS (FAB$^+$) for $C_{28}H_{36}FN_4O_4$ (MH$^+$): calcd, 511.2721; found, 511.2719.

Step 2:

Synthesis of (2S,4S)-1-[[N-[4-(pyrrolidin-1-yl)carbonylbicyclo[2.2.2]oct-1-yl]amino]acetyl]-4-fluoropyrrolidine-2-carbonitrile (2S,4S)-1-[[N-Benzyloxycarbonyl-N-[4-(piperidin-1-yl)carbonylbicyclo[2.2.2]oct-1-yl]amino]acetyl]-4-fluoropyrrolidine-2-carbonitrile (30.0 mg) and 10% palladium carbon (3.0 mg) were dissolved in ethanol (1.0 mL) and dichloromethane (0.5 mL). The mixture was stirred at room temperature for 8 hours in a hydrogen atmosphere. The mixture was then filtered through a Celite pad and the solvent was concentrated under reduced pressure. The resulting residue was purified by column chromatography (eluant:dichloromethane:methanol=10:1) to give (2S,4S)-1-[[N-[4-(pyrrolidin-1-yl)carbonylbicyclo[2.2.2]oct-1-yl]amino]acetyl]-4-fluoropyrrolidine-2-carbonitrile (15.2 mg).

MS (EI$^+$) m/z: 376 (M$^+$). HRMS (EI$^+$) for $C_{20}H_{29}FN_4O_2$ (M$^+$): calcd, 376.2275; found, 376.2285.

EXAMPLE 5

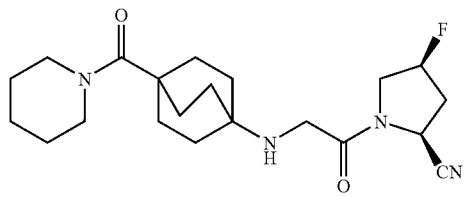

Synthesis of (2S,4S)-1-[[N-[4-(piperidin-1-yl)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(piperidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (100 mg) and piperidine (22.7 μL) were used to obtain (2S,4S)-1-[[N-benzyloxycarbonyl-N-[4-(piperidin-1-yl)carbonylbicyclo[2.2.2]oct-1-yl]amino]acetyl]-4-fluoropyrrolidine-2-carbonitrile (81.0 mg).

MS (FAB$^+$) m/z: 525 (MH$^+$). HRMS (FAB$^+$) for $C_{29}H_{38}FN_4O_4$ (MH$^+$): calcd, 525.2877; found, 525.2896.

Step 2:

Synthesis of (2S,4S)-1-[[N-[4-(piperidin-1-yl)carbonylbicyclo[2.2.2]oct-1-yl]amino]acetyl]-4-fluoropyrrolidine-2-carbonitrile (2S,4S)-1-[[N-Benzyloxycarbonyl-N-[4-(piperidin-1-yl)carbonylbicyclo[2.2.2]oct-1-yl]amino]acetyl]-4-fluoropyrrolidine-2-carbonitrile (20.0 mg) and 10% palladium carbon (12.0 mg) were dissolved in dimethylformamide (0.5 mL). While the solution was chilled in an ice bath, ammonium formate (43.1 mg) was added and the mixture was stirred for 40 minutes at the same temperature. Subsequently, the reaction mixture was filtered through a Celite pad and diluted with ethyl acetate. The organic layer washed sequentially with water and saturated brine, dried over anhydrous sodium sulfate, and concentrated under reduced pressure. The resulting residue was purified by column chromatography (eluant: dichloromethane:methanol=10:1) to give (2S,4S)-1-[[N-[4-(piperidin-1-yl)carbonylbicyclo[2.2.2]oct-1-yl]amino]acetyl]-4-fluoropyrrolidine-2-carbonitrile (13.2 mg).

MS (EI$^+$) m/z: 390 (M$^+$). HRMS (EI$^+$) for $C_{21}H_{31}FN_4O_2$ (M$^+$): calcd, 390.2431; found, 390.2446.

EXAMPLE 6

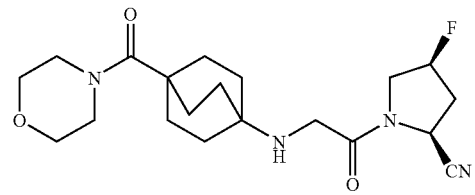

Synthesis of (2S,4S)-4-fluoro-1-[[N-[4-(morpholin-4-yl)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(morpholin-4-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and morpholine (9.9 μL) were used to obtain (2S,4S)-1-[[N-benzyloxycarbonyl-N-[4-(morpholin-4-yl)carbonylbicyclo[2.2.2]oct-1-yl]amino]acetyl]-4-fluoropyrrolidine-2-carbonitrile (43.6 mg).

MS (FAB$^+$) m/z: 527 (MH$^+$). HRMS (FAB$^+$) for $C_{28}H_{36}FN_4O_5$ (MH$^+$): calcd, 527.2670; found, 527.2651.

Step 2:

Synthesis of (2S,4S)-4-fluoro-1-[[N-[4-(morpholin-4-yl)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(morpholin-4-yl)carbonylbicyclo[2.2.2]oct-1-yl]amino]acetyl]-4-fluoropyrrolidine-2-carbonitrile (34.0 mg) was used to obtain (2S,4S)-4-fluoro-1-[[N-[4-(morpholin-4-yl)carbonylbicyclo[2.2.2]oct-1-yl]amino]acetyl]pyrrolidine-2-carbonitrile (13.2 mg).

MS (FAB$^+$) m/z: 393 (MH$^+$). HRMS (FAB$^+$) for C$_{20}$H$_{30}$FN$_4$O$_3$ (MH$^+$): calcd, 393.2302; found, 393.2304.

EXAMPLE 7

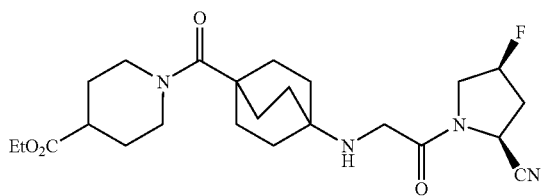

Synthesis of (2S,4S)-1-[[N-[4-(4-ethoxycarbonylpiperidin-1-yl)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(4-ethoxycarbonylpiperidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-ethoxycarbonylpiperidine (20.1 μL) were used to obtain (2S,4S)-1-[[N-benzyloxycarbonyl-N-[4-(4-ethoxycarbonylpiperidin-1-yl)carbonylbicyclo[2.2.2]oct-1-yl]amino]acetyl]-4-fluoropyrrolidine-2-carbonitrile (43.1 mg).

MS (FAB$^+$) m/z: 597 (MH$^+$). HRMS (FAB$^+$) for C$_{32}$H$_{42}$FN$_4$O$_6$ (MH$^+$): calcd, 597.3088; found, 597.3096.

Step 2:

Synthesis of (2S,4S)-1-[[N-[4-(4-ethoxycarbonylpiperidin-1-yl)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(4-ethoxycarbonylpiperidin-1-yl)carbonylbicyclo[2.2.2]oct-1-yl]amino]acetyl]-4-fluoropyrrolidine-2-carbonitrile (36.4 mg) was used to obtain (2S,4S)-1-[[N-[4-(4-ethoxycarbonylpiperidin-1-yl)carbonylbicyclo[2.2.2]oct-1-yl]amino]acetyl]-4-fluoropyrrolidine-2-carbonitrile (22.1 mg).

MS (FAB$^+$) m/z: 463 (MH$^+$). HRMS (FAB$^+$) for C$_{24}$H$_{36}$FN$_4$O$_4$ (MH$^+$): calcd, 463.2721; found, 463.2723.

EXAMPLE 8

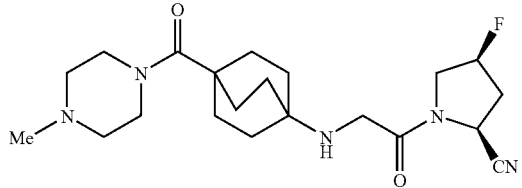

Synthesis of (2S,4S)-4-fluoro-1-[[N-[4-(4-methylpiperazin-1-yl)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(4-methylpiperazin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-methylpiperazine (14.5 μL) were used to obtain (2S,4S)-1-[[N-benzyloxycarbonyl-N-[4-(4-methylpiperazin-1-yl)carbonylbicyclo[2.2.2]oct-1-yl]amino]acetyl]-4-fluoropyrrolidine-2-carbonitrile (36.0 mg).

MS (FAB$^+$) m/z: 540 (MH$^+$). HRMS (FAB$^+$) for C$_{29}$H$_{39}$FN$_5$O$_4$ (MH$^+$): calcd, 540.2986; found, 540.2974.

Step 2:

Synthesis of (2S,4S)-4-fluoro-1-[[N-[4-(4-methylpiperazin-1-yl)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(4-methylpiperazin-1-yl)carbonylbicyclo[2.2.2]oct-1-yl]amino]acetyl]-4-fluoropyrrolidine-2-carbonitrile (31.0 mg) was used to obtain (2S,4S)-4-fluoro-1-[[N-[4-(4-methylpiperazin-1-yl)carbonylbicyclo[2.2.2]oct-1-yl]amino]acetyl]pyrrolidine-2-carbonitrile (15.7 mg).

MS (EI$^+$) m/z: 405 (M$^+$). HRMS (EI$^+$) for C$_{21}$H$_{32}$FN$_5$O$_2$ (M$^+$): calcd, 405.2540; found, 405.2562.

EXAMPLE 9

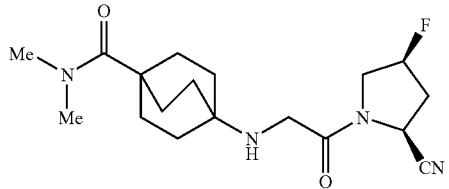

Synthesis of (2S,4S)-1-[[N-[4-(dimethylamino)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(dimethylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazole-1-yl)oxycarbonylbicyclo[2.2.2]oct-1-yl]amino]acetyl]-4-fluoropyrrolidine-2-carbonitrile (50.0 mg) and 2.0 M tetrahydrofuran solution of dimethylamine (65.0 μL) were used to obtain (2S,4S)-1-[[N-benzyloxycarbonyl-N-[4-(dimethylamino)carbonylbicyclo[2.2.2]oct-1-yl]amino]acetyl]-4-fluoropyrrolidine-2-carbonitrile (36.2 mg).

MS (FAB$^+$) m/z: 485 (MH$^+$). HRMS (FAB$^+$) for $C_{26}H_{34}FN_4O_4$ (MH$^+$): calcd, 485.2564; found, 485.2554.

Step 2:

Synthesis of (2S,4S)-1-[[N-[4-(dimethylamino)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(dimethylamino)carbonylbicyclo[2.2.2]oct-1-yl]amino]acetyl]-4-fluoropyrrolidine-2-carbonitrile (36.0 mg) was used to obtain (2S,4S)-1-[[N-[4-(dimethylamino)carbonylbicyclo[2.2.2]oct-1-yl]amino]acetyl]-4-fluoropyrrolidine-2-carbonitrile (16.7 mg).

MS (EI$^+$) m/z: 350 (M$^+$). HRMS (EI$^+$) for $C_{18}H_{27}FN_4O_2$ (M$^+$): calcd, 350.2118; found, 350.2156.

EXAMPLE 10

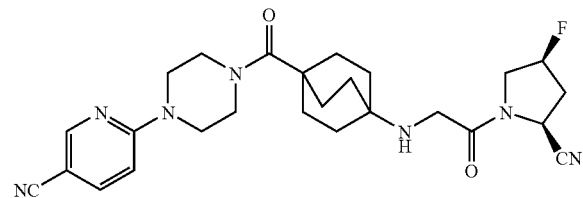

Synthesis of (2S,4S)-1-[[N-[4-[(5-cyanopyridin-2-yl)piperazin-1-yl]carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-[(5-cyanopyridin-2-yl)piperazin-1-yl]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and (5-cyanopyridin-2-yl)piperazine (24.6 mg) were used to obtain (2S,4S)-1-[[benzyloxycarbonyl-N-[4-[(5-cyanopyridin-2-yl)piperazin-1-yl]carbonylbicyclo[2.2.2]oct-1-yl]amino]acetyl]-4-fluoropyrrolidine-2-carbonitrile (45.0 mg).

MS (FAB$^+$) m/z: 628 (MH$^+$). HRMS (FAB$^+$) for $C_{34}H_{39}FN_7O_4$ (MH$^+$): calcd, 628.3048; found, 628.3035.

Step 2:

Synthesis of (2S,4S)-1-[[N-[4-[(5-cyanopyridin-2-yl)piperazin-1-yl]carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-[(5-cyanopyridin-2-yl)piperazin-1-yl]carbonylbicyclo[2.2.2]oct-1-yl]amino]acetyl]-4-fluoropyrrolidine-2-carbonitrile (45.0 mg) was used to obtain (2S,4S)-1-[[N-[4-[(5-cyanopyridin-2-yl)piperazin-1-yl]carbonylbicyclo[2.2.2]oct-1-yl]amino]acetyl]-4-fluoropyrrolidine-2-carbonitrile (26.1 mg).

MS (FAB$^+$) m/z: 494 (MH$^+$). HRMS (FAB$^+$) for $C_{26}H_{33}FN_7O_2$ (MH$^+$): calcd, 494.2680; found, 494.2684.

EXAMPLE 11

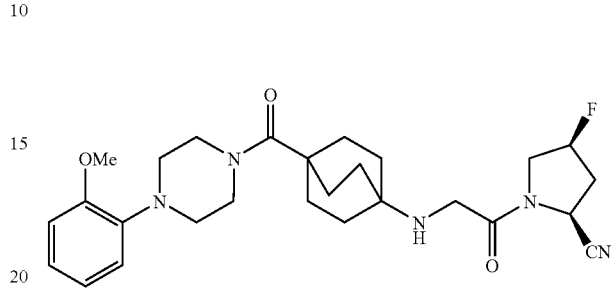

Synthesis of (2S,4S)-4-fluoro-1-[[N-[4-[(2-methoxyphenyl)piperazin-1-yl]carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-[(2-methoxyphenyl)piperazin-1-yl]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and (2-methoxyphenyl)piperazine (22.9 μL) were used to obtain (2S,4S)-1-[[N-benzyloxycarbonyl-N-[4-[(2-methoxyphenyl)piperazin-1-yl]carbonylbicyclo[2.2.2]oct-1-yl]amino]acetyl]-4-fluoropyrrolidine-2-carbonitrile (43.2 mg).

MS (FAB$^+$) m/z: 632 (MH$^+$). HRMS (FAB$^+$) for $C_{35}H_{43}FN_5O_5$ (MH$^+$): calcd, 632.3248; found, 632.3273.

Step 2:

Synthesis of (2S,4S)-4-fluoro-1-[[N-[4-[(2-methoxyphenyl)piperazin-1-yl]carbonylbicyclo[2.2.2]oct-1-yl]amino]acetyl]pyrrolidine-2-carbonitril In a similar manner to Example 5, (2S,4S)-1-[[N-benzyloxycarbonyl-N-[4-[(2-methoxyphenyl)piperazin-1-yl]carbonylbicyclo[2.2.2]oct-1-yl]amino]acetyl]-4-fluoropyrrolidine-2-carbonitrile (43.0 mg) was used to obtain (2S,4S)-4-fluoro-1-[[N-[4-[(2-methoxyphenyl)piperazin-1-yl]carbonylbicyclo[2.2.2]oct-1-yl]amino]acetyl]pyrrolidine-2-carbonitrile (24.0 mg).

MS (FAB$^+$) m/z: 498 (MH$^+$). HRMS (FAB$^+$) for $C_{27}H_{37}FN_5O_3$ (MH$^+$): calcd, 498.2880; found, 498.2905.

EXAMPLE 12

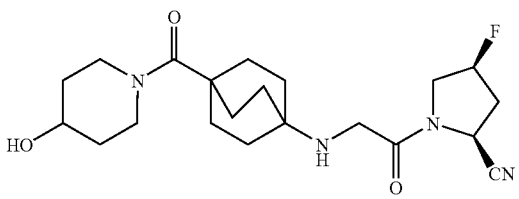

Synthesis of (2S,4S)-4-fluoro-1-[[N-[4-(4-hydroxypiperidin-1-yl)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(4-hydroxypiperidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-hydroxypiperidine (11.7 mg) were used to obtain (2S,4S)-1-[[N-benzyloxycarbonyl-N-[4-(4-hydroxypiperidin-1-yl)carbonylbicyclo[2.2.2]oct-1-yl]amino]acetyl]-4-fluoropyrrolidine-2-carbonitrile (39.0 mg).

MS (FAB$^+$) m/z: 541 (MH$^+$). HRMS (FAB$^+$) for $C_{29}H_{38}FN_4O_5$ (MH$^+$): calcd, 541.2826; found, 541.2836.

Step 2:

Synthesis of (2S,4S)-4-fluoro-1-[[N-[4-(4-hydroxypiperidin-1-yl)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(4-hydroxypiperidin-1-yl)carbonylbicyclo[2.2.2]oct-1-yl]amino]acetyl]-4-fluoropyrrolidine-2-carbonitrile (39.0 mg) was used to obtain (2S,4S)-4-fluoro-1-[[N-[4-(4-hydroxypiperidin-1-yl)carbonylbicyclo[2.2.2]oct-1-yl]amino]acetyl]pyrrolidine-2-carbonitrile (7.0 mg).

MS (EI$^+$) m/z: 406 (M$^+$). HRMS (EI$^+$) for $C_{21}H_{31}FN_4O_3$ (M$^+$): calcd, 406.2380; found, 406.2399.

EXAMPLE 13

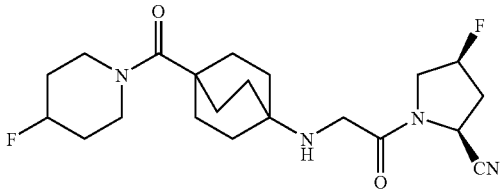

Synthesis of (2S,4S)-4-fluoro-1-[[N-[4-(4-fluoropiperidin-1-yl)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(4-fluoropiperidin-1-yl)carbonylbicyclo[2.2.2]oct-1-yl]amino]acetyl]-4-fluoropyrrolidine-2-carbonitrile 4-Fluoropiperidine hydrochloride (18.2 mg) was suspended in tetrahydrofuran (0.87 mL). While this suspension was chilled in an ice bath, triethylamine (18.2 μL) was added and the mixture was stirred at the same temperature for 35 minutes. Subsequently, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) was added and the mixture was stirred at room temperature overnight. The reaction mixture was diluted with dichloromethane and washed sequentially with 0.1 N aqueous hydrochloric acid, saturated aqueous sodium bicarbonate solution and saturated brine. The organic layer was dried over anhydrous sodium sulfate and was concentrated under reduced pressure. The resulting residue was purified by column chromatography (eluant:ethyl acetate:methanol=20:1) to give (2S,4S)-1-[[N-benzyloxycarbonyl-[4-(4-fluoropiperidin-1-yl)carbonylbicyclo[2.2.2]oct-1-yl]amino]acetyl]-4-fluoropyrrolidine-2-carbonitrile (37.0 mg).

MS (FAB$^+$) m/z: 543 (MH$^+$). HRMS (FAB$^+$) for $C_{29}H_{37}F_2N_4O_4$ (MH$^+$): calcd, 543.2783; found, 543.2794.

Step 2:

Synthesis of (2S,4S)-4-fluoro-1-[[N-[4-(4-fluoropiperidin-1-yl)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(4-fluoropiperidin-1-yl)carbonylbicyclo[2.2.2]oct-1-yl]amino]acetyl]-4-fluoropyrrolidine-2-carbonitrile (37.0 mg) was used to obtain (2S,4S)-4-fluoro-1-[[N-[4-(4-fluoropiperidin-1-yl)carbonylbicyclo[2.2.2]oct-1-yl]amino]acetyl]pyrrolidine-2-carbonitrile (16.4 mg).

MS (FAB$^+$) m/z: 409 (MH$^+$). HRMS (FAB$^+$) for $C_{21}H_{31}F_2N_4O_2$ (MH$^+$): calcd, 409.2415; found, 409.2392.

EXAMPLE 14

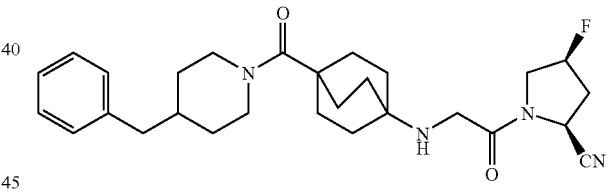

Synthesis of (2S,4S)-1-[[N-[4-(4-benzylpiperidin-1-yl)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(4-benzylpiperidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-benzylpiperidine (22.9 μL) were used to obtain (2S,4S)-1-[[N-benzyloxycarbonyl-N-[4-(4-benzylpiperidin-1-yl)carbonylbicyclo[2.2.2]oct-1-yl]amino]acetyl]-4-fluoropyrrolidine-2-carbonitrile (45.9 mg).

MS (FAB$^+$) m/z: 615 (MH$^+$). HRMS (FAB$^+$) for $C_{36}H_{44}FN_4O_4$ (MH$^+$): calcd, 615.3347; found, 615.3388.

Step 2:

Synthesis of (2S,4S)-1-[[N-[4-(4-benzylpiperidin-1-yl)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(4-benzylpiperidin-1-yl)carbonylbicyclo[2.2.2]oct-1-yl]amino]acetyl]-4-fluoropyrrolidine-2-carbonitrile (45.9 mg) was used to obtain (2S,4S)-1-[[N-[4-(4-benzylpiperidin-1-yl)carbonylbicyclo[2.2.2]oct-1-yl]amino]acetyl]-4-fluoropyrrolidine-2-carbonitrile (23.0 mg).

MS (FAB$^+$) m/z: 481 (MH$^+$). HRMS (FAB$^+$) for C$_{28}$H$_{38}$FN$_4$O$_2$ (MH$^+$): calcd, 481.2979; found, 481.2935.

EXAMPLE 15

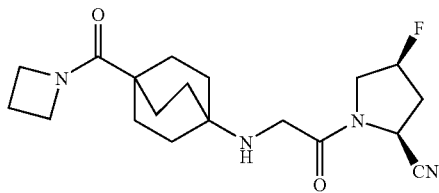

Synthesis of (2S,4S)-1-[[[4-(azetidin-1-yl)carbonylbicyclo[2.2.2]oct-1-yl]amino]acetyl]-4-fluoropyrrolidine-2-carbonitrile Step 1:

Synthesis of (2S,4S)-1-[[N-[4-(azetidin-1-yl)carbonylbicyclo[2.2.2]oct-1-yl-N-benzyloxycarbonyl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and azetidine hydrochloride (12.2 mg) were used to obtain (2S,4S)-1-[[N-[4-(azetidin-1-yl)carbonylbicyclo[2.2.2]oct-1-yl-N-benzyloxycarbonyl]amino]acetyl]-4-fluoropyrrolidine-2-carbonitrile (32.0 mg).

MS (FAB$^+$) m/z: 497 (MH$^+$). HRMS (FAB$^+$) for C$_{27}$H$_{34}$FN$_4$O$_4$ (MH$^+$): calcd, 497.2564; found, 497.2567.

Step 2:

Synthesis of (2S,4S)-1-[[N-[4-(azetidin-1-yl)carbonylbicyclo[2.2.2]oct-1-yl]amino]acetyl]-4-fluoropyrrolidine-2-carbonitrile In a similar manner to Example 5, (2S,4S)-1-[[N-[4-(azetidin-1-yl)carbonylbicyclo[2.2.2]oct-1-yl-N-benzyloxycarbonyl]amino]acetyl]-4-fluoropyrrolidine-2-carbonitrile (27.0 mg) was used to obtain (2S,4S)-1-[[N-[4-(azetidin-1-yl)carbonylbicyclo[2.2.2]oct-1-yl]amino]acetyl]-4-fluoropyrrolidine-2-carbonitrile (10.0 mg).

MS (FAB$^+$) m/z: 363 (MH$^+$). HRMS (FAB$^+$) for C$_{19}$H$_{28}$FN$_4$O$_2$ (MH$^+$): calcd, 363.2196; found, 363.2221.

EXAMPLE 16

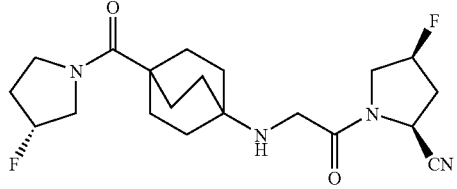

Synthesis of (2S,4S,3' R)-4-fluoro-1-[[N-[4-(3-fluoropyrrolidin-1-yl)carbonylbicyclo[2.2.2]oct-1-yl]amino]acetyl]pyrrolidine-2-carbonitrile Step 1:

Synthesis of (2S,4S,3' R)-1-[[N-benzyloxycarbonyl-N-[4-(3-fluoropyrrolidin-1-yl)carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and (3R)-3-fluoropyrrolidine hydrochloride (16.4 mg) were used to obtain (2S,4S,3' R)-1-[[N-benzyloxycarbonyl-N-[4-(3-fluoropyrrolidin-1-yl)carbonylbicyclo[2.2.2]oct-1-yl]amino]acetyl]-4-fluoropyrrolidine-2-carbonitrile (39.7 mg).

MS (FAB$^+$) m/z: 529 (MH$^+$). HRMS (FAB$^+$) for C$_{28}$H$_{35}$F$_2$N$_4$O$_4$ (MH$^+$): calcd, 529.2626; found, 529.2642.

Step 2:

Synthesis of (2S,4S,3' R)-4-fluoro-1-[[N-[4-(3-fluoropyrrolidin-1-yl)carbonylbicyclo[2.2.2]oct-1-yl]amino]acetyl]pyrrolidine-2-carbonitrile In a similar manner to Example 5, (2S,4S,3' R)-1-[[N-benzyloxycarbonyl-N-[4-(3-fluoropyrrolidin-1-yl)carbonylbicyclo[2.2.2]oct-1-yl]amino]acetyl]-4-fluoropyrrolidine-2-carbonitrile (39.7 mg) was used to obtain (2S,4S,3' R)-4-fluoro-1-[[N-[4-(3-fluoropyrrolidin-1-yl)carbonylbicyclo[2.2.2]oct-1-yl]amino]acetyl]pyrrolidine-2-carbonitrile (15.8 mg).

MS (FAB$^+$) m/z: 395 (MH$^+$). HRMS (FAB$^+$) for C$_{20}$H$_{29}$F$_2$N$_4$O$_2$ (MH$^+$): calcd, 395.2259; found, 395.2216.

EXAMPLE 17

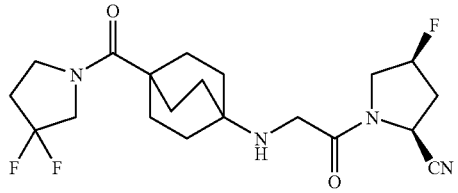

Synthesis of (2S,4S)-4-fluoro-1-[[N-[4-(3,3-difluoropyrrolidin-1-yl)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(3,3-difluoropyrrolidin-1-yl)carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo

[2.2.2]oct-1-yl]amino]acetyl]-4-fluoropyrrolidine-2-carbonitrile (50.0 mg) and 3,3-difluoropyrrolidine hydrochloride (18.7 mg) were used to obtain (2S,4S)-1-[[N-benzyloxycarbonyl-N-[4-(3,3-difluoropyrrolidin-1-yl)carbonylbicyclo[2.2.2]oct-1-yl]amino]acetyl]-4-fluoropyrrolidine-2-carbonitrile (40.8 mg).

MS (FAB⁺) m/z: 547 (MH⁺). HRMS (FAB⁺) for $C_{28}H_{34}F_3N_4O_4$ (MH⁺): calcd, 547.2532; found, 547.2549.

Step 2:

Synthesis of (2S,4S)-4-fluoro-1-[[N-[4-(3,3-difluoropyrrolidin-1-yl)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(3,3-difluoropyrrolidin-1-yl)carbonylbicyclo[2.2.2]oct-1-yl]amino]acetyl]-4-fluoropyrrolidine-2-carbonitrile (40.8 mg) was used to obtain (2S,4S)-4-fluoro-1-[[N-[4-(3,3-difluoropyrrolidin-1-yl)carbonylbicyclo[2.2.2]oct-1-yl]amino]acetyl]pyrrolidine-2-carbonitrile (26.6 mg).

MS (FAB⁺) m/z: 413 (MH⁺). HRMS (FAB⁺) for $C_{20}H_{28}F_3N_4O_2$ (MH⁺): calcd, 413.2164; found, 413.2126.

EXAMPLE 18

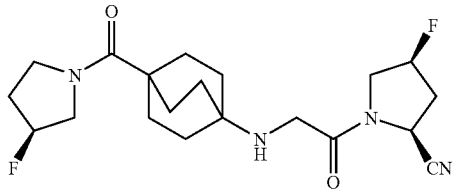

Synthesis of (2S,4S,3' S)-4-fluoro-1-[[N-[4-(3-fluoropyrrolidin-1-yl)carbonylbicyclo[2.2.2]oct-1-yl]amino]acetyl]pyrrolidine-2-carbonitrile Step 1:

Synthesis of (2S,4S,3' S)-1-[[N-benzyloxycarbonyl-N-[4-(3-fluoropyrrolidin-1-yl)carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and (3S)-3-fluoropyrrolidine hydrochloride (16.4 mg) were used to obtain (2S,4S,3' S)-1-[[N-benzyloxycarbonyl-N-[4-(3-fluoropyrrolidin-1-yl)carbonylbicyclo[2.2.2]oct-1-yl]amino]acetyl]-4-fluoropyrrolidine-2-carbonitrile (35.3 mg).

MS (FAB⁺) m/z: 529 (MH⁺). HRMS (FAB⁺) for $C_{28}H_{35}F_2N_4O_4$ (MH⁺): calcd, 529.2626; found, 529.2642.

Step 2:

Synthesis of (2S,4S,3' S)-4-fluoro-1-[[N-[4-(3-fluoropyrrolidin-1-yl)carbonylbicyclo[2.2.2]oct-1-yl]amino]acetyl]pyrrolidine-2-carbonitrile In a similar manner to Example 5, (2S,4S,3' S)-1-[[N-benzyloxycarbonyl-N-[4-(3-fluoropyrrolidin-1-yl)carbonylbicyclo[2.2.2]oct-1-yl]amino]acetyl]-4-fluoropyrrolidine-2-carbonitrile (35.3 mg) was used to obtain (2S,4S,3' S)-4-fluoro-1-[[N-[4-(3-fluoropyrrolidin-1-yl)carbonylbicyclo[2.2.2]oct-1-yl]amino]acetyl]pyrrolidine-2-carbonitrile (19.9 mg).

MS (FAB⁺) m/z: 395 (MH⁺). HRMS (FAB⁺) for $C_{20}H_{29}F_2N_4O_2$ (MH⁺): calcd, 395.2259; found, 395.2266.

EXAMPLE 19

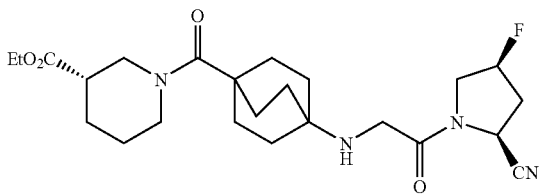

Synthesis of (2S,4S,3' S)-1-[[N-[4-(3-ethoxycarbonylpiperidin-1-yl)carbonylbicyclo[2.2.2]oct-1-yl]amino]acetyl]-4-fluoropyrrolidine-2-carbonitrile Step 1:

(2S,4S,3' S)-1-[[N-Benzyloxycarbonyl-N-[4-(3-ethoxycarbonylpiperidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (70.0 mg) and (S)-(+)-nipecotic acid ethyl ester (28.0 μL) were used to obtain (2S,4S,3' S)-1-[[N-benzyloxycarbonyl-N-[4-(3-ethoxycarbonylpiperidin-1-yl)carbonylbicyclo[2.2.2]oct-1-yl]amino]acetyl]-4-fluoropyrrolidine-2-carbonitrile (53.8 mg).

MS (FAB⁺) m/z: 597 (MH⁺). HRMS (FAB⁺) for $C_{32}H_{42}FN_4O_6$ (MH⁺): calcd, 597.3088; found, 597.3108.

Step 2:

Synthesis of (2S,4S,3' S)-1-[[N-[4-(3-ethoxycarbonylpiperidin-1-yl)carbonylbicyclo[2.2.2]oct-1-yl]amino]acetyl]-4-fluoropyrrolidine-2-carbonitrile In a similar manner to Example 5, (2S,4S,3' S)-1-[[N-benzyloxycarbonyl-N-[4-(3-ethoxycarbonylpiperidin-1-yl)carbonylbicyclo[2.2.2]oct-1-yl]amino]acetyl]-4-fluoropyrrolidine-2-carbonitrile (53.8 mg) was used to obtain (2S,4S,3' S)-1-[[N-[4-(3-ethoxycarbonylpiperidin-1-yl)carbonylbicyclo[2.2.2]oct-1-yl]amino]acetyl]-4-fluoropyrrolidine-2-carbonitrile (25.2 mg).

MS (FAB⁺) m/z: 463 (MH⁺). HRMS (FAB⁺) for $C_{24}H_{36}FN_4O_4$ (MH⁺): calcd, 463.2721; found, 463.2690.

EXAMPLE 20

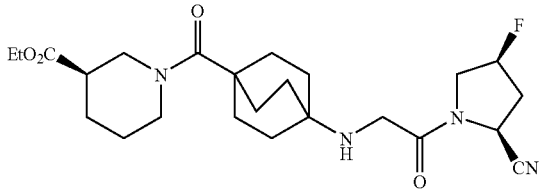

Synthesis of (2S,4S,3' R)-1-[[N-[4-(3-ethoxycarbonylpiperidin-1-yl)carbonylbicyclo[2.2.2]oct-1-yl]amino]acetyl]-4-fluoropyrrolidine-2-carbonitrile Step 1:

Synthesis of (2S,4S,3' R)-1-[[N-benzyloxycarbonyl-N-[4-(3-ethoxycarbonylpiperidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo

[2.2.2]oct-1-yl]amino]acetyl]-4-fluoropyrrolidine-2-carbonitrile (80.0 mg) and (R)-(−)-nipecotic acid ethyl ester (32.2 μL) were used to obtain (2S,4S,3' R)-1-[[N-benzyloxycarbonyl-N-[4-(3-ethoxycarbonylpiperidin-1-yl)carbonylbicyclo[2.2.2]oct-1-yl]amino]acetyl]-4-fluoropyrrolidine-2-carbonitrile (78.3 mg).

MS (FAB$^+$) m/z: 597 (MH$^+$). HRMS (FAB$^+$) for $C_{32}H_{42}FN_4O_6$ (MH$^+$): calcd, 597.3088; found, 597.3096.

Step 2:

Synthesis of (2S,4S,3' R)-1-[[N-[4-(3-ethoxycarbonylpiperidin-1-yl)carbonylbicyclo[2.2.2]oct-1-yl]amino]acetyl]-4-fluoropyrrolidine-2-carbonitrile In a similar manner to Exampler 5, (2S,4S,3' R)-1-[[N-benzyloxycarbonyl-N-[4-(3-ethoxycarbonylpiperidin-1-yl)carbonylbicyclo[2.2.2]oct-1-yl]amino]acetyl]-4-fluoropyrrolidine-2-carbonitrile (78.3 mg) was used to obtain (2S,4S,3' R)-1-[[N-[4-(3-ethoxycarbonylpiperidin-1-yl)carbonylbicyclo[2.2.2]oct-1-yl]amino]acetyl]-4-fluoropyrrolidine-2-carbonitrile (47.2 mg).

MS (FAB$^+$) m/z: 463 (MH$^+$). HRMS (FAB$^+$) for $C_{24}H_{36}FN_4O_4$ (MH$^+$): calcd, 463.2721; found, 463.2711.

EXAMPLE 21

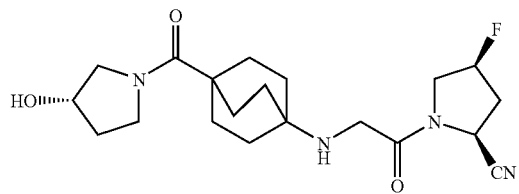

Synthesis of (2S,4S,3' S)-1-[[N-[4-(3-hydroxypyrrolidin-1-yl)carbonylbicyclo[2.2.2]oct-1-yl]amino]acetyl]-4-fluoropyrrolidine-2-carbonitrile Step 1:

Synthesis of (2S,4S,3' S)-1-[[N-benzyloxycarbonyl-N-[4-(3-hydroxypyrrolidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and (3S)-3-hydroxypyrrolidine (9.1 μL) were used to obtain (2S,4S,3' S)-1-[[N-benzyloxycarbonyl-N-[4-(3-hydroxypyrrolidin-1-yl)carbonylbicyclo[2.2.2]oct-1-yl]amino]acetyl]-4-fluoropyrrolidine-2-carbonitrile (35.0 mg).

MS (FAB$^+$) m/z: 527 (MH$^+$). HRMS (FAB$^+$) for $C_{28}H_{36}FN_4O_5$ (MH$^+$): calcd, 527.2670; found, 527.2679

Step 2:

Synthesis of (2S,4S,3' S)-1-[[N-[4-(3-hydroxypyrrolidin-1-yl)carbonylbicyclo[2.2.2]oct-1-yl]amino]acetyl]-4-fluoropyrrolidine-2-carbonitrile In a similar manner to Example 5, (2S,4S,3' S)-1-[[N-benzyloxycarbonyl-N-[4-(3-hydroxypyrrolidin-1-yl)carbonylbicyclo[2.2.2]oct-1-yl]amino]acetyl]-4-fluoropyrrolidine-2-carbonitrile (35.0 mg) was used to obtain (2S,4S,3' S)-1-[[N-[4-(3-hydroxypyrrolidin-1-yl)carbonylbicyclo[2.2.2]oct-1-yl]amino]acetyl]-4-fluoropyrrolidine-2-carbonitrile (15.2 mg).

MS (FAB$^+$) m/z: 393 (MH$^+$). HRMS (FAB$^+$) for $C_{20}H_{30}FN_4O_3$ (MH$^+$): calcd, 393.2302; found, 393.2300.

EXAMPLE 22

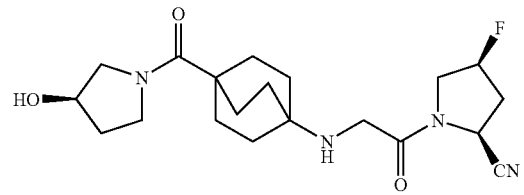

Synthesis of (2S,4S,3' R)-1-[[N-[4-(3-hydroxypyrrolidin-1-yl)carbonylbicyclo[2.2.2]oct-1-yl]amino]acetyl]-4-fluoropyrrolidine-2-carbonitrile Step 1:

Synthesis of (2S,4S,3' R)-1-[[N-benzyloxycarbonyl-N-[4-(3-hydroxypyrrolidin-1-yl)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (80.0 mg) and (3R)-3-hydroxypyrrolidine (16.9 μL) were used to obtain (2S,4S,3' R)-1-[[N-benzyloxycarbonyl-N-[4-(3-hydroxypyrrolidin-1-yl)carbonylbicyclo[2.2.2]oct-1-yl]amino]acetyl]-4-fluoropyrrolidine-2-carbonitrile (75.0 mg).

MS (FAB$^+$) m/z: 527 (MH$^+$). HRMS (FAB$^+$) for $C_{28}H_{36}FN_4O_5$ (MH$^+$): calcd, 527.2670; found, 527.2679

Step 2:

Synthesis of (2S,4S,3' R)-1-[[N-[4-(3-hydroxypyrrolidin-1-yl)carbonylbicyclo[2.2.2]oct-1-yl]amino]acetyl]-4-fluoropyrrolidine-2-carbonitrile In a similar manner to Example 5, (2S,4S,3' R)-1-[[N-benzyloxycarbonyl-N-[4-(3-hydroxypyrrolidin-1-yl)carbonylbicyclo[2.2.2]oct-1-yl]amino]acetyl]-4-fluoropyrrolidine-2-carbonitrile (75.0 mg) was used to obtain (2S,4S,3' R)-1-[[N-[4-(3-hydroxypyrrolidin-1-yl)carbonylbicyclo[2.2.2]oct-1-yl]amino]acetyl]-4-fluoropyrrolidine-2-carbonitrile (38.9 mg).

MS (FAB$^+$) m/z: 393 (MH$^+$). HRMS (FAB$^+$) for $C_{20}H_{30}FN_4O_3$ (MH$^+$): calcd, 393.2302; found, 393.2274.

EXAMPLE 23

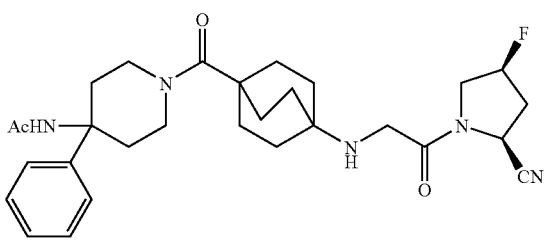

Synthesis of (2S,4S)-1-[[[4-(4-acetylamino-4-phenylpiperidin-1-yl)carbonylbicyclo[2.2.2]oct-1-yl]amino]acetyl]-4-fluoropyrrolidine-2-carbonitrile Step 1:

Synthesis of (2S,4S)-1-[[N-[4-(4-acetylamino-4-phenylpiperidin-1-yl)carbonylbicyclo[2.2.2]oct-1-yl-N-benzyloxycarbonyl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (80.0 mg) and 4-acetylamino-4-phenylpiperidine hydrochloride (53.2 mg) were used to obtain (2S,4S)-1-[[N-[4-(4-acetylamino-4-phenylpiperidin-1-yl)carbonylbicyclo[2.2.2]oct-1-yl-N-benzyloxycarbonyl]amino]acetyl]-4-fluoropyrrolidine-2-carbonitrile (64.5 mg).

MS (FAB$^+$) m/z: 658 (MH$^+$). HRMS (FAB$^+$) for $C_{37}H_{45}FN_5O_5$ (MH$^+$): calcd, 658.3405; found, 658.3414.

Step 2:

Synthesis of (2S,4S)-1-[[N-[4-(4-acetylamino-4-phenylpiperidin-1-yl)carbonylbicyclo[2.2.2]oct-1-yl]amino]acetyl]-4-fluoropyrrolidine-2-carbonitrile In a similar manner to Example 5, (2S,4S)-1-[[N-[4-(4-acetylamino-4-phenylpiperidin-1-yl)carbonylbicyclo[2.2.2]oct-1-yl-N-benzyloxycarbonyl]amino]acetyl]-4-fluoropyrrolidine-2-carbonitrile (64.5 mg) was used to obtain (2S,4S)-1-[[N-[4-(4-acetylamino-4-phenylpiperidin-1-yl)carbonylbicyclo[2.2.2]oct-1-yl]amino]acetyl]-4-fluoropyrrolidine-2-carbonitrile (31.2 mg).

MS (FAB$^+$) m/z: 524 (MH$^+$). HRMS (FAB$^+$) for $C_{29}H_{39}FN_5O_3$ (MH$^+$): calcd, 524.3037; found, 524.3047.

EXAMPLE 24

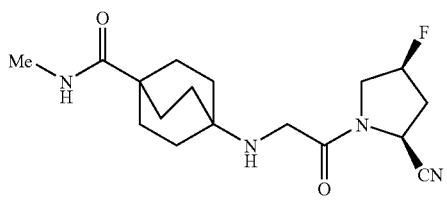

Synthesis of (2S,4S)-4-fluoro-1-[[N-[4-(N-methylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-methylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and methylamine (2.0 mol/l THF solution, 60.0 μL) were used to obtain (2S,4S)-1-[[N-benzyloxycarbonyl-N-[4-(N-methylamino)carbonylbicyclo[2.2.2]oct-1-yl]amino]acetyl]-4-fluoropyrrolidine-2-carbonitrile (28.9 mg).

MS (FAB$^+$) m/z: 471 (MH$^+$).
Rf 0.25 (ethyl acetate:methanol=9:1).

Step 2:

Synthesis of (2S,4S)-4-fluoro-1-[[N-[4-(N-methylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-methylamino)carbonylbicyclo[2.2.2]oct-1-yl]amino]acetyl]-4-fluoropyrrolidine-2-carbonitrile (27.0 mg) was used to obtain (2S,4S)-4-fluoro-1-[[N-[4-(N-methylamino)carbonylbicyclo[2.2.2]oct-1-yl]amino]acetyl]pyrrolidine-2-carbonitrile (10.8 mg).

MS (FAB$^+$) m/z: 337 (MH$^+$). HRMS (FAB$^+$) for $C_{17}H_{25}FN_4O_2$ (MH$^+$): calcd, 337.2040; found, 337.2040.

EXAMPLE 25

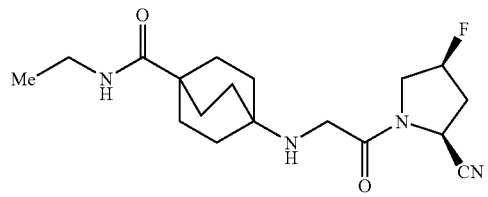

Synthesis of (2S,4S)-1-[[N-[4-(N-ethylamino)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(N-ethylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and ethylamine (2.0 mol/L THF solution, 60.0 μL) were used to obtain (2S,4S)-1-[[N-benzyloxycarbonyl-N-[4-(N-ethylamino)carbonylbicyclo[2.2.2]oct-1-yl]amino]acetyl]-4-fluoropyrrolidine-2-carbonitrile (24.6 mg).

MS (FAB$^+$) m/z: 485 (MH$^+$).
Rf 0.33 (ethyl acetate:methanol=15:1).

Step 2:

Synthesis of (2S,4S)-1-[[N-[4-(N-ethylamino)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(N-ethylamino)carbonylbicyclo[2.2.2]oct-1-yl]amino]acetyl]-4-fluoropyrrolidine-2-carbonitrile (22.6 mg) was used to obtain (2S,4S)-4-fluoro-1-[[N-[4-(N-ethylamino)carbonylbicyclo[2.2.2]oct-1-yl]amino]acetyl]pyrrolidine-2-carbonitrile (11.4 mg).

MS (FAB$^+$) m/z: 351 (MH$^+$). HRMS (FAB$^+$) for $C_{18}H_{28}FN_4O_2$ (MH$^+$): calcd, 351.2196; found, 351.2181.

EXAMPLE 26

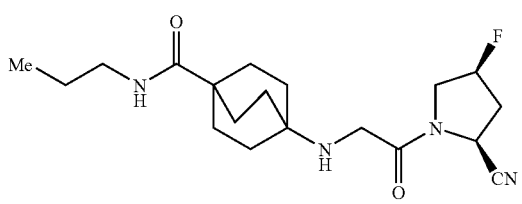

Synthesis of (2S,4S)-4-fluoro-1-[[N-[4-(N-propylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-propylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and propylamine (10.0 μL) were used to obtain (2S,4S)-1-[[N-benzyloxycarbonyl-N-[4-(N-propylamino)carbonylbicyclo[2.2.2]oct-1-yl]amino]acetyl]-4-fluoropyrrolidine-2-carbonitrile (28.7 mg).

MS (FAB$^+$) m/z: 499 (MH$^+$).
Rf 0.38 (ethyl acetate:methanol=15:1).

Step 2:

Synthesis of (2S,4S)-4-fluoro-1-[[N-[4-(N-propylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-propylamino)carbonylbicyclo[2.2.2]oct-1-yl]amino]acetyl]-4-fluoropyrrolidine-2-carbonitrile (25.8 mg) was used to obtain (2S,4S)-4-fluoro-1-[[N-[4-(N-propylamino)carbonylbicyclo[2.2.2]oct-1-yl]amino]acetyl]pyrrolidine-2-carbonitrile (14.9 mg).

MS (FAB$^+$) m/z: 365 (MH$^+$). HRMS (FAB$^+$) for $C_{19}H_{30}FN_4O_2$ (MH$^+$) calcd, 365.2353; found, 365.2382.

EXAMPLE 27

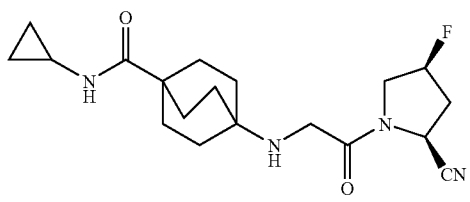

Synthesis of (2S,4S)-1-[[N-[4-(N-cyclopropylamino)carbonylbicyclo[2.2.2]oct-1-yl]amino]acetyl]-A4-fluoropyrrolidine-2-carbonitrile Step 1:

Synthesis of (2S,4S)-1-[[N-benzyloxycarbonyl-N-[4-(N-cyclopropylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and cyclopropylamine (8.0 μL) were used to obtain (2S,4S)-1-[[N-benzyloxycarbonyl-N-[4-(N-cyclopropylamino)carbonylbicyclo[2.2.2]oct-1-yl]amino]acetyl]-4-fluoropyrrolidine-2-carbonitrile (31.6 mg).

MS (FAB$^+$) m/z: 497 (MH$^+$).
Rf 0.35 (ethyl acetate:methanol=15:1).

Step 2:

Synthesis of (2S,4S)-1-[[N-[4-(N-cyclopropylamino)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(N-cyclopropylamino)carbonylbicyclo[2.2.2]oct-1-yl]amino]acetyl]-4-fluoropyrrolidine-2-carbonitrile (30.1 mg) was used to obtain (2S,4S)-1-[[N-[4-(N-cyclopropylamino)carbonylbicyclo[2.2.2]oct-1-yl]amino]acetyl]-4-fluoropyrrolidine-2-carbonitrile (16.7 mg).

MS (FAB$^+$) m/z: 363 (MH$^+$). HRMS (FAB$^+$) for $C_{19}H_{28}FN_4O_2$ (MH$^+$): calcd, 363.2196; found, 363.2217.

EXAMPLE 28

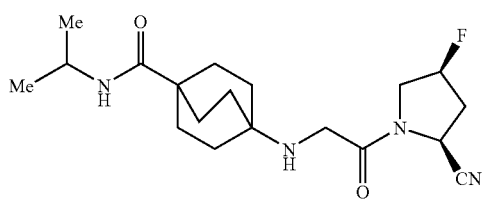

Synthesis of (2S,4S)-4-fluoro-1-[[N-[4-(N-1-methylethylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-1-methylethylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 1-methylethylamine (10.0 μL) were used to obtain (2S,4S)-1-[[N-benzyloxycarbonyl-N-[4-(N-1-methylethylamino)carbonylbicyclo[2.2.2]oct-1-yl]amino]acetyl]-4-fluoropyrrolidine-2-carbonitrile (33.6 mg).

MS (FAB$^+$) m/z: 499 (MH$^+$).
Rf 0.25 (ethyl acetate:methanol=20:1).

Step 2:

Synthesis of (2S,4S)-4-fluoro-1-[[N-[4-(N-1-methylethylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-1-methylethylamino)carbonylbicyclo[2.2.2]oct-1-yl]amino]acetyl]-4-fluoropyrrolidine-2-carbonitrile (31.2 mg) was used to obtain (2S,4S)-4-fluoro-1-[[N-[4-(N-1-methylethylamino)carbonylbicyclo[2.2.2]oct-1-yl]amino]acetyl]pyrrolidine-2-carbonitrile (15.7 mg).

MS (FAB$^+$) m/z: 365 (MH$^+$). HRMS (FAB$^+$) for $C_{19}H_{30}FN_4O_2$ (MH$^+$): calcd, 365.2353; found, 365.2345.

EXAMPLE 29

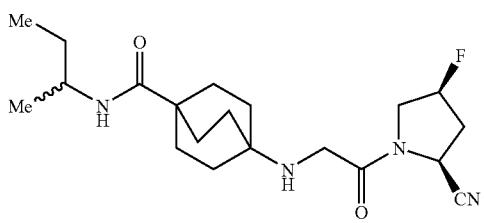

Synthesis of (2S,4S,1' RS)-4-fluoro-1-[[N-[4-(N-1-methylpropylamino)carbonylbicyclo[2.2.2]oct-1-yl]amino]acetyl]pyrrolidine-2-carbonitrile Step 1:

Synthesis of (2S,4S,1' RS)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 1-methylpropylamine (12.0 μL) were used to obtain (2S,4S,1'RS)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile (32.0 mg).
MS (FAB⁺) m/z: 513 (MH⁺).
Rf 0.33 (ethyl acetate).

Step 2:

Synthesis of (2S,4S,1' RS)-4-fluoro-1-[[N-[4-(N-1-methylpropylamino)carbonylbicyclo[2.2.2]oct-1-yl]amino]acetyl]pyrrolidine-2-carbonitrile In a similar manner to Example 5, (2S,4S,1' RS)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile (29.0 mg) was used to obtain (2S,4S,1' RS)-4-fluoro-1-[[N-[4-(N-1-methylpropylamino)carbonylbicyclo[2.2.2]oct-1-yl]amino]acetyl]pyrrolidine-2-carbonitrile (14.9 mg).
MS (FAB⁺) m/z: 379 (MH⁺). HRMS (FAB⁺) for $C_{20}H_{32}FN_4O_2$ (MH⁺): calcd, 379.2509; found, 379.2497.

EXAMPLE 30

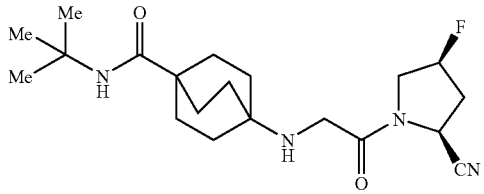

Synthesis of (2S,4S)-1-[[N-[4-(N-2,2-dimethylethylamino)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(N-2,2-dimethylethylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 2,2-dimethylethylamine (12.0 μL) were used to obtain (2S,4S)-1-[[N-benzyloxycarbonyl-N-[4-(N-2,2-dimethylethylamino)carbonylbicyclo[2.2.2]oct-1-yl]amino]acetyl]-4-fluoropyrrolidine-2-carbonitrile (31.5 mg).
MS (FAB⁺) m/z: 513 (MH⁺).
Rf 0.45 (ethyl acetate).

Step 2:

Synthesis of (2S,4S)-1-[[N-[4-(N-2,2-dimethylethylamino)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(N-2,2-dimethylethylamino)carbonylbicyclo[2.2.2]oct-1-yl]amino]acetyl]-4-fluoropyrrolidine-2-carbonitrile (28.9 mg) was used to obtain (2S,4S)-4-fluoro-1-[[N-[4-(N-2,2-dimethylethylamino)carbonylbicyclo[2.2.2]oct-1-yl]amino]acetyl]pyrrolidine-2-carbonitrile (17.3 mg).
MS (FAB⁺) m/z: 379 (MH⁺). HRMS (FAB⁺) for $C_{20}H_{32}FN_4O_2$ (MH⁺): calcd, 379.2509; found, 379.2518.

EXAMPLE 31

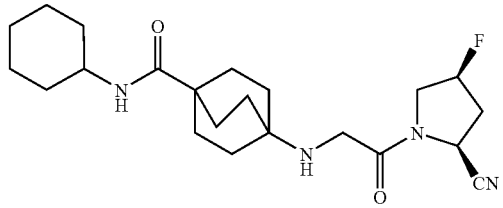

Synthesis of (2S,4S)-1-[[N-[4-(N-cyclohexylamino)carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-(N-cyclohexylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and cyclohexylamine (13.0 μL) were used to obtain (2S,4S)-1-[[N-benzyloxycarbonyl-N-[4-(N-cyclohexylamino)carbonylbicyclo[2.2.2]oct-1-yl]amino]acetyl]-4-fluoropyrrolidine-2-carbonitrile (35.0 mg).
MS (FAB⁺) m/z: 539 (MH⁺).
Rf 0.35 (ethyl acetate).

Step 2:

Synthesis of (2S,4S)-1-[[N-[4-(N-cyclohexylamino)carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-(N-cyclohexylamino)carbonylbicyclo[2.2.2]oct-1-yl]amino]acetyl]-4-fluoropyrrolidine-2-carbonitrile (31.6 mg) was used to obtain (2S,4S)-1-[[N-[4-(N-cyclohexylamino)carbonylbicyclo[2.2.2]oct-1-yl]amino]acetyl]-4-fluoropyrrolidine-2-carbonitrile (17.5 mg).
MS (FAB⁺) m/z: 405 (MH⁺). HRMS (FAB⁺) for $C_{22}H_{34}FN_4O_2$ (MH⁺): calcd, 405.2666; found, 405.2628.

EXAMPLE 32

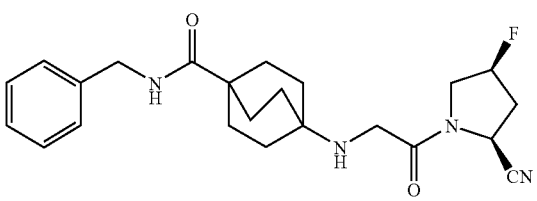

Synthesis of (2S,4S)-1-[[N-[4-(N-benzylamino)carbonylbicyclo[2.2.2]oct-1-yl]amino]acetyl]-4-fluoropyrrolidine-2-carbonitrile Step 1:

Synthesis of (2S,4S)-1-[[N-[4-(N-benzylamino)carbonylbicyclo[2.2.2]oct-1-yl]-N-benzyloxycarbonylamino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and benzylamine (13.0 μL) were used to obtain (2S,4S)-1-[[N-[4-(N-benzylamino)carbonylbicyclo[2.2.2]oct-1-yl-N-benzyloxycarbonyl]amino]acetyl]-4-fluoropyrrolidine-2-carbonitrile (32.1 mg).

MS (FAB$^+$) m/z: 547 (MH$^+$).
Rf 0.30 (ethyl acetate).

Step 2:

Synthesis of (2S,4S)-1-[[N-[4-(N-benzylamino)carbonylbicyclo[2.2.2]oct-1-yl]amino]acetyl]-4-fluoropyrrolidine-2-carbonitrile In a similar manner to Example 5, (2S,4S)-1-[[N-[4-(N-benzylamino)carbonylbicyclo[2.2.2]oct-1-yl-N-benzyloxycarbonyl]amino]acetyl]-4-fluoropyrrolidine-2-carbonitrile (30.0 mg) was used to obtain (2S,4S)-1-[[N-[4-(N-benzylamino)carbonylbicyclo[2.2.2]oct-1-yl]amino]acetyl]-4-fluoropyrrolidine-2-carbonitrile (13.7 mg).

MS (FAB$^+$) m/z: 413 (MH$^+$). HRMS (FAB$^+$) for $C_{23}H_{30}FN_4O_2$ (MH$^+$): calcd, 413.2353; found, 413.2345.

EXAMPLE 33

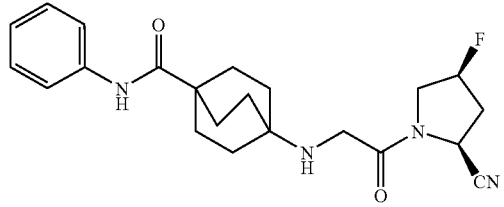

Synthesis of (2S,4S)-4-fluoro-1-[[N-[4-(N-phenylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-phenylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and aniline (10.0 μL) were used to obtain (2S,4S)-1-[[N-benzyloxycarbonyl-N-[4-(N-phenylamino)carbonylbicyclo[2.2.2]oct-1-yl]amino]acetyl]-4-fluoropyrrolidine-2-carbonitrile (35.4 mg).

MS (FAB$^+$) m/z: 533 (MH$^+$).
Rf 0.33 (ethyl acetate:hexane=4:1).

Step 2:

Synthesis of (2S,4S)-4-fluoro-1-[[N-[4-(N-phenylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-phenylamino)carbonylbicyclo[2.2.2]oct-1-yl]amino]acetyl]-4-fluoropyrrolidine-2-carbonitrile (31.2 mg) was used to obtain (2S,4S)-4-fluoro-1-[[N-[4-(N-phenylamino)carbonylbicyclo[2.2.2]oct-1-yl]amino]acetyl]pyrrolidine-2-carbonitrile (16.6 mg).

MS (FAB$^+$) m/z: 399 (MH$^+$). HRMS (FAB$^+$) for $C_{22}H_{28}FN_4O_2$ (MH$^+$) calcd, 399.2196; found, 399.2220.

EXAMPLE 34

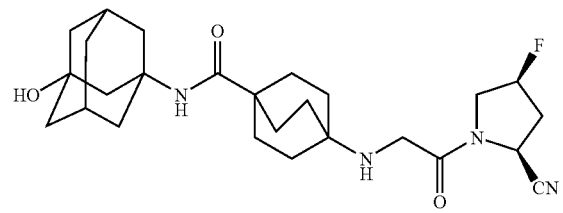

Synthesis of (2S,4S)-4-fluoro-1-[[N-[4-(N-3-hydroxyadamantylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-3-hydroxyadamantylamino)carbonylbicyclo[2.2.2]oct-1-yl]amino]acetyl]-4-fluoropyrrolidine-2-carbonitrile In a similar manner to Example 4, (2S,4S)-1-[[N-20 benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 3-aminoadamantanol (18.9 mg) were used to obtain (2S,4S)-1-[[N-benzyloxycarbonyl-N-[4-(N-3-hydroxyadamantylamino)carbonylbicyclo[2.2.2]oct-1-yl]amino]acetyl]-4-fluoropyrrolidine-2-carbonitrile (40.0 mg).

MS (FAB$^+$) m/z: 607 (MH$^+$).
Rf 0.33 (ethyl acetate:methanol=9:1).

Step 2:

Synthesis of (2S,4S)-4-fluoro-1-[[N-[4-(N-3-hydroxyadamantylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-3-hydroxyadamantylamino)carbonylbicyclo[2.2.2]oct-1-yl]amino]acetyl]-4-fluoropyrrolidine-2-carbonitrile (37.4 mg) was used to obtain (2S,4S)-4-fluoro-1-[[N-[4-(N-3-hydroxyadamantylamino)carbonylbicyclo[2.2.2]oct-1-yl]amino]acetyl]pyrrolidine-2-carbonitrile (21.9 mg).

MS (FAB$^+$) m/z: 473 (MH$^+$). HRMS (FAB$^+$) for $C_{26}H_{38}FN_4O_3$ (MH$^+$): calcd, 473.2928; found, 473.2952.

EXAMPLE 35

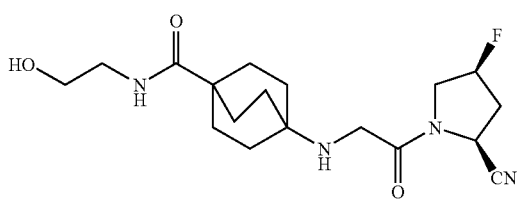

Synthesis of (2S,4S)-4-fluoro-1-[[N-[4-(N-2-hydroxyethylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-2-hydroxyethylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 2-aminoethanol (6.9 mg) were used to obtain (2S,4S)-1-[[N-benzyloxycarbonyl-N-[4-(N-2-hydroxyethylamino)carbonylbicyclo[2.2.2]oct-1-yl]amino]acetyl]-4-fluoropyrrolidine-2-carbonitrile (27.2 mg).

MS (FAB$^+$) m/z: 501 (MH$^+$).
Rf 0.31 (dichloromethane:methanol=15:1).

Step 2:

Synthesis of (2S,4S)-4-fluoro-1-[[N-[4-(N-2-hydroxyethylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-2-hydroxyethylamino)carbonylbicyclo[2.2.2]oct-1-yl]amino]acetyl]-4-fluoropyrrolidine-2-carbonitrile (25.0 mg) was used to obtain (2S,4S)-4-fluoro-1-[[N-[4-(N-2-hydroxyethylamino)carbonylbicyclo[2.2.2]oct-1-yl]amino]acetyl]pyrrolidine-2-carbonitrile (12.2 mg).

MS (FAB$^+$) m/z: 367 (MH$^+$). HRMS (FAB$^+$) for $C_{18}H_{28}FN_4O_3$ (MH$^+$): calcd, 367.2145; found, 367.2150.

EXAMPLE 36

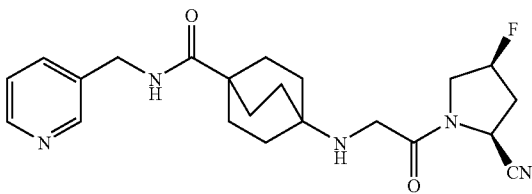

Synthesis of (2S,4S)-4-fluoro-1-[[N-[4-(N-3-pyridylmethylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-3-pyridylmethylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 3-pyridylmethylamine (12.0 µL) were used to obtain (2S,4S)-1-[[N-benzyloxycarbonyl-N-[4-(N-3-pyridylmethylamino)carbonylbicyclo[2.2.2]oct-1-yl]amino]acetyl]-4-fluoropyrrolidine-2-carbonitrile (36.2 mg).

MS (FAB$^+$) m/z: 548 (MH$^+$).
Rf 0.33 (dichloromethane:methanol=15:1).

Step 2:

Synthesis of (2S,4S)-4-fluoro-1-[[N-[4-(N-3-pyridylmethylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-3-pyridylmethylamino)carbonylbicyclo[2.2.2]oct-1-yl]amino]acetyl]-4-fluoropyrrolidine-2-carbonitrile (34.6 mg) was used to obtain (2S,4S)-4-fluoro-1-[[N-[4-(N-3-pyridylmethylamino)carbonylbicyclo[2.2.2]oct-1-yl]amino]acetyl]pyrrolidine-2-carbonitrile (14.0 mg).

MS (FAB$^+$) m/z: 414 (MH$^+$). HRMS (FAB$^+$) for $C_{22}H_{29}FN_5O_2$ (MH$^+$): calcd, 414.2305; found, 414.2311.

EXAMPLE 37

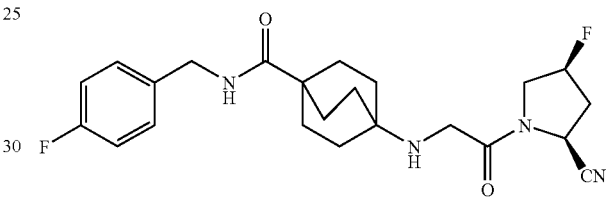

Synthesis of (2S,4S)-4-fluoro-1-[[N-[4-(N-4-fluorobenzylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-4-fluorobenzylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-fluorobenzylamine (13.0 µL) were used to obtain (2S,4S)-1-[[N-benzyloxycarbonyl-N-[4-(N-4-fluorobenzylamino)carbonylbicyclo[2.2.2]oct-1-yl]amino]acetyl]-4-fluoropyrrolidine-2-carbonitrile (38.3 mg).

MS (FAB$^+$) m/z: 565 (MH$^+$).
Rf 0.48 (ethyl acetate:methanol=20:1).

Step 2:

Synthesis of (2S,4S)-4-fluoro-1-[[N-[4-(N-4-fluorobenzylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-4-fluorobenzylamino)carbonylbicyclo[2.2.2]oct-1-yl]amino]acetyl]-4-fluoropyrrolidine-2-carbonitrile (35.3 mg) was used to obtain (2S,4S)-4-fluoro-1-[[N-[4-(N-4-fluorobenzylamino)carbonylbicyclo[2.2.2]oct-1-yl]amino]acetyl]pyrrolidine-2-carbonitrile (17.3 mg).

MS (FAB$^+$) m/z: 431 (MH$^+$). HRMS (FAB$^+$) for $C_{23}H_{29}F_2N_4O_2$ (MH$^+$): calcd, 431.2259; found, 431.2246.

EXAMPLE 38

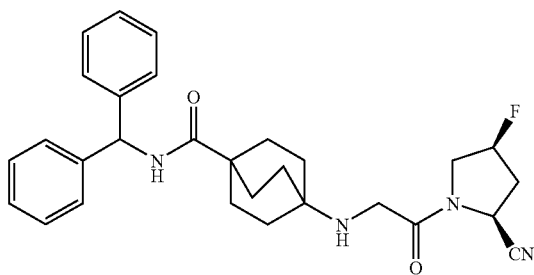

Synthesis of (2S,4S)-1-[[N-[4-(N-diphenylmethylamino)carbonylbicyclo[2.2.2]oct-1-yl]amino]acetyl]-4-fluoropyrrolidine-2-carbonitrile Step 1:

Synthesis of (2S,4S)-1-[[N-[4-(N-diphenylmethylamino)carbonylbicyclo[2.2.2]oct-1-yl]-N-benzyloxycarbonylamino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and diphenylmethylamine (20.0 μL) were used to obtain (2S,4S)-1-[[N-[4-(N-diphenylmethylamino)carbonylbicyclo[2.2.2]oct-1-yl-N-benzyloxycarbonyl]amino]acetyl]-4-fluoropyrrolidine-2-carbonitrile (40.0 mg).

MS (FAB⁺) m/z: 623 (MH⁺). Rf 0.63 (ethyl acetate).

Step 2:

Synthesis of (2S,4S)-1-[[N-[4-(N-diphenylmethylamino)carbonylbicyclo[2.2.2]oct-1-yl]amino]acetyl]-4-fluoropyrrolidine-2-carbonitrile In a similar manner to Example 5, (2S,4S)-1-[[N-[4-(N-diphenylmethylamino)carbonylbicyclo[2.2.2]oct-1-yl-N-benzyloxycarbonyl]amino]acetyl]-4-fluoropyrrolidine-2-carbonitrile (37.4 mg) was used to obtain (2S,4S)-1-[[N-[4-(N-diphenylmethylamino)carbonylbicyclo[2.2.2]oct-1-yl]amino]acetyl]-4-fluoropyrrolidine-2-carbonitrile (20.3 mg).

MS (FAB⁺) m/z: 489 (MH⁺). HRMS (FAB⁺) for $C_{29}H_{34}FN_4O_2$ (MH⁺): calcd, 489.2666; found, 489.2675.

EXAMPLE 39

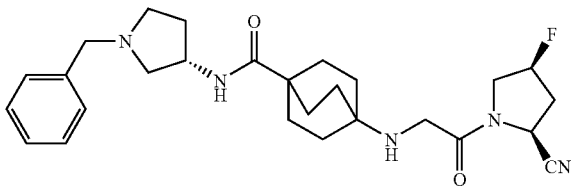

Synthesis of (2S,4S,3' S)-1-[[N-[4-[N-(1-benzylpyrrolidin-3-yl)amino]carbonylbicyclo[2.2.2]oct-1-yl]amino]acetyl]-4-fluoropyrrolidine-2-carbonitrile Step 1:

Synthesis of (2S,4S,3' S)-1-[[N-benzyloxycarbonyl-N-[4-[N-(1-benzylpyrrolidin-3-yl)amino]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 3(S)-amino-1-benzylpyrrolidine (20.0 μL) were used to obtain (2S,4S,3' S)-1-[[N-benzyloxycarbonyl-N-[4-[N-(1-benzylpyrrolidin-3-yl)amino]carbonylbicyclo[2.2.2]oct-1-yl]amino]acetyl]-4-fluoropyrrolidine-2-carbonitrile (36.9 mg).

MS (FAB⁺) m/z: 616 (MH⁺). Rf 0.25 (dichloromethane:methanol=20:1).

Step 2:

Synthesis of (2S,4S,3' S)-1-[[N-[4-[N-(1-benzylpyrrolidin-3-yl)amino]carbonylbicyclo[2.2.2]oct-1-yl]amino]acetyl]-4-fluoropyrrolidine-2-carbonitrile In a similar manner to Example 5, ((2S,4S,3' S)-1-[[N-benzyloxycarbonyl-N-[4-[N-(1-benzylpyrrolidin-3-yl)amino]carbonylbicyclo[2.2.2]oct-1-yl]amino]acetyl]-4-fluoropyrrolidine-2-carbonitrile (34.5 mg) was used to obtain (2S,4S,3' S)-1-[[N-[4-[N-(1-benzylpyrrolidin-3-yl)amino]carbonylbicyclo[2.2.2]oct-1-yl]amino]acetyl]-4-fluoropyrrolidine-2-carbonitrile (11.7 mg).

MS (FAB⁺) m/z: 482 (MH⁺). HRMS (FAB⁺) for $C_{27}H_{37}FN_5O_2$ (MH⁺): calcd, 482.2931; found, 482.2926.

EXAMPLE 40

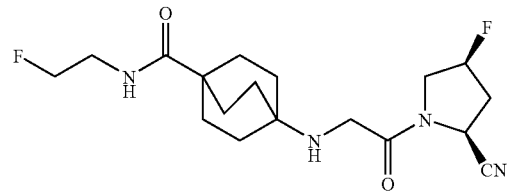

Synthesis of (2S,4S)-4-fluoro-1-[[N-[4-(N-2-fluoroethylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-2-fluoroethylamino)carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 2-fluoroethylamine hydrochloride (11.2 mg) were used to obtain (2S,4S)-1-[[N-benzyloxycarbonyl-N-[4-(N-2-fluoroethylamino)carbonylbicyclo[2.2.2]oct-1-yl]amino]acetyl]-4-fluoropyrrolidine-2-carbonitrile (33.9 mg).

MS (FAB⁺) m/z: 503 (MH⁺). Rf 0.33 (ethyl acetate:methanol=15:1).

Step 2:

Synthesis of (2S,4S)-4-fluoro-1-[[N-[4-(N-2-fluoroethylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-4-fluorobenzylamino)carbonylbicyclo[2.2.2]oct-1-yl]amino]acetyl]-4-fluoropyrrolidine-2-carbonitrile (32.0 mg) was used to obtain (2S,4S)-4-fluoro-1-[[N-[4-(N-2-fluoroethylamino)carbonylbicyclo[2.2.2]oct-1-yl]amino]acetyl]pyrrolidine-2-carbonitrile (14.2 mg).

MS (FAB⁺) m/z: 369 (MH⁺). HRMS (FAB⁺) for $C_{18}H_{27}F_2N_4O_2$ (MH⁺): calcd, 369.2102; found, 369.2103.

EXAMPLE 41

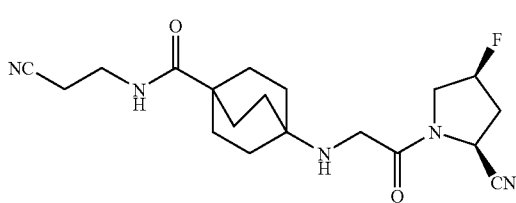

Synthesis of (2S,4S)-1-[[N-[4-(N-2-cyanoethylamino)carbonylbicyclo[2.2.2]oct-1-yl]amino]acetyl]-4-fluoropyrrolidine-2-carbonitrile Step 1:

Synthesis of (2S,4S)-1-[[N-[4-(N-2-cyanoethylamino)carbonylbicyclo[2.2.2]oct-1-yl]-N-benzyloxycarbonylamino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 2-cyanoethylamine (9.0 μL) were used to obtain (2S,4S)-1-[[N-[4-(N-2-cyanoethylamino)carbonylbicyclo[2.2.2]oct-1-yl-N-benzyloxycarbonyl]amino]acetyl]-4-fluoropyrrolidine-2-carbonitrile (29.1 mg).

MS (FAB$^+$) m/z: 510 (MH$^+$). Rf 0.40 (ethyl acetate:methanol=9:1).

Step 2:

Synthesis of (2S,4S)-1-[[N-[4-(N-2-cyanoethylamino)carbonylbicyclo[2.2.2]oct-1-yl]amino]acetyl]-4-fluoropyrrolidine-2-carbonitrile In a similar manner to Example 5, (2S,4S)-1-[[N-[4-(N-2-cyanoethylamino)carbonylbicyclo[2.2.2]oct-1-yl-N-benzyloxycarbonyl]amino]acetyl]-4-fluoropyrrolidine-2-carbonitrile (25.2 mg) was used to obtain (2S,4S)-1-[[N-[4-(N-2-cyanoethylamino)carbonylbicyclo[2.2.2]oct-1-yl]amino]acetyl]-4-fluoropyrrolidine-2-carbonitrile (14.5 mg).

MS (FAB$^+$) m/z: 376 (MH$^+$). HRMS (FAB$^+$) for $C_{19}H_{27}FN_5O_2$ (MH$^+$): calcd, 376.2149; found, 376.2161.

EXAMPLE 42

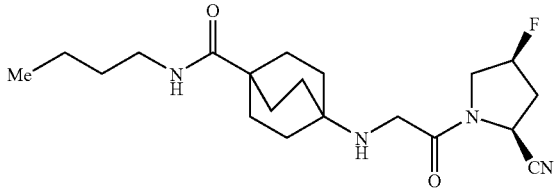

Synthesis of (2S,4S)-4-fluoro-1-[[N-[4-(N-butylamino)carbonylbicyclo[2.2.2]oct-1-yl]amino]acetyl]pyrrolidine-2-carbonitrile Step 1:

Synthesis of (2S,4S)-1-([N-benzyloxycarbonyl-N-[4-(N-butylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and butylamine (11.5 μL) were used to obtain (2S,4S)-1-[[N-benzyloxycarbonyl-N-[4-(N-butylamino)carbonylbicyclo[2.2.2]oct-1-yl]amino]acetyl]-4-fluoropyrrolidine-2-carbonitrile (44.0 mg).

MS (FAB$^+$) m/z: 513 (MH$^+$). Rf 0.25 (ethyl acetate).

Step 2:

Synthesis of (2S,4S)-4-fluoro-1-[[N-[4-(N-butylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-butylamino)carbonylbicyclo[2.2.2]oct-1-yl]amino]acetyl]-4-fluoropyrrolidine-2-carbonitrile (37.0 mg) was used to obtain (2S,4S)-4-fluoro-1-[[N-[4-(N-butylamino)carbonylbicyclo[2.2.2]oct-1-yl]amino]acetyl]pyrrolidine-2-carbonitrile (22.8 mg).

MS (FAB$^+$) m/z: 379 (MH$^+$). HRMS (FAB$^+$) for $C_{20}H_{32}FN_4O_2$ (MH$^+$): calcd, 379.2509; found, 379.2504.

EXAMPLE 43

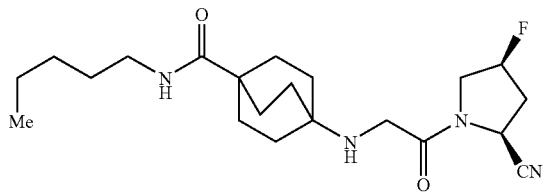

Synthesis of (2S,4S)-4-fluoro-1-[[N-[4-(N-pentylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-pentylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and pentylamine (15.0 μL) were used to obtain (2S,4S)-1-[[N-benzyloxycarbonyl-N-[4-(N-pentylamino)carbonylbicyclo[2.2.2]oct-1-yl]amino]acetyl]-4-fluoropyrrolidine-2-carbonitrile (39.6 mg).

MS (FAB$^+$) m/z: 527 (MH$^+$). Rf 0.43 (ethyl acetate:methanol=20:1).

Step 2:

Synthesis of (2S,4S)-4-fluoro-1-[[N-[4-(N-pentylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-pentylamino)carbonylbicyclo[2.2.2]oct-1-yl]amino]acetyl]-4-fluoropyrrolidine-2-carbonitrile (37.6 mg) was used to obtain (2S,4S)-4-fluoro-1-[[N-[4-(N-pentylamino)carbonylbicyclo[2.2.2]oct-1-yl]amino]acetyl]pyrrolidine-2-carbonitrile (21.4 mg).

MS (FAB$^+$) m/z: 393 (MH$^+$). HRMS (FAB$^+$) for $C_{21}H_{34}FN_4O_2$ (MH$^+$): calcd, 393.2666; found, 393.2633.

EXAMPLE 44

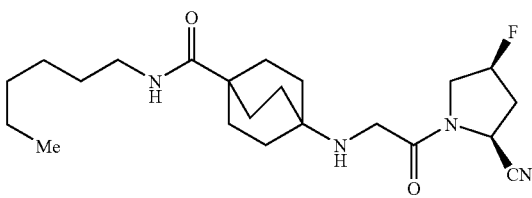

Synthesis of (2S,4S)-4-fluoro-1-[[N-[4-(N-hexylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-hexylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and hexylamine (15.0 µL) were used to obtain (2S,4S)-1-[[N-benzyloxycarbonyl-N-[4-(N-hexylamino)carbonylbicyclo[2.2.2]oct-1-yl]amino]acetyl]-4-fluoropyrrolidine-2-carbonitrile (42.7 mg).

MS (FAB$^+$) m/z: 541 (MH$^+$). Rf 0.45 (ethyl acetate:methanol=20:1).

Step 2:

Synthesis of (2S,4S)-4-fluoro-1-[[N-[4-(N-hexylamino)carbonylbicyclo[2.2.2]oct-1-yl]amino]acetyl]pyrrolidine-2-carbonitrile In a similar manner to Example 5, (2S,4s)-1-[[N-benzyloxycarbonyl-N-[4-(N-hexylamino)carbonylbicyclo[2.2.2]oct-1-yl]amino]acetyl]-4-fluoropyrrolidine-2-carbonitrile (41.0 mg) was used to obtain (2S,4S)-4-fluoro-1-[[N-[4-(N-hexylamino)carbonylbicyclo[2.2.2]oct-1-yl]amino]acetyl]pyrrolidine-2-carbonitrile (24.5 mg).

MS (FAB$^+$) m/z: 407 (MH$^+$). HRMS (FAB$^+$) for $C_{22}H_{36}FN_4O_2$ (MH$^+$): calcd, 407.2822; found, 407.2794.

EXAMPLE 45

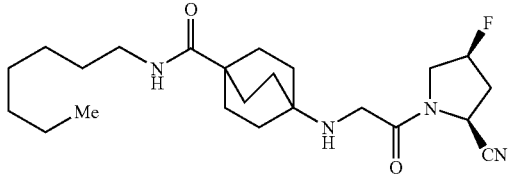

Synthesis of (2S,4S)-4-fluoro-1-[[N-[4-(N-heptylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-heptylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and heptylamine (20.0 µL) were used to obtain (2S,4S)-1-[[N-benzyloxycarbonyl-N-[4-(N-heptylamino)carbonylbicyclo[2.2.2]oct-1-yl]amino]acetyl]-4-fluoropyrrolidine-2-carbonitrile (42.9 mg).

MS (FAB$^+$) m/z: 555 (MH$^+$). Rf 0.45 (ethyl acetate).

Step 2:

Synthesis of (2S,4S)-4-fluoro-1-[[N-[4-(N-heptylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-heptylamino)carbonylbicyclo[2.2.2]oct-1-yl]amino]acetyl]-4-fluoropyrrolidine-2-carbonitrile (39.7 mg) was used to obtain (2S,4S)-4-fluoro-1-[[N-[4-(N-heptylamino)carbonylbicyclo[2.2.2]oct-1-yl]amino]acetyl]pyrrolidine-2-carbonitrile (22.2 mg).

MS (FAB$^+$) m/z: 421 (MH$^+$). HRMS (FAB$^+$) for $C_{23}H_{38}FN_4O_2$ (MH$^+$): calcd, 421.2979; found, 421.3002.

EXAMPLE 46

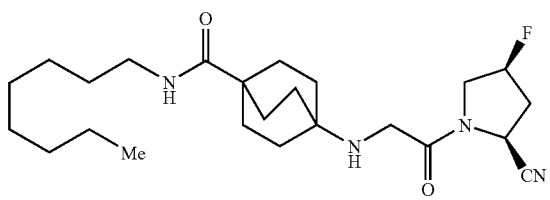

Synthesis of (2S,4S)-4-fluoro-1-[[N-[4-(N-octylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-octylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and octylamine (15.0 µL) were used to obtain (2S,4S)-1-[[N-benzyloxycarbonyl-N-[4-(N-octylamino)carbonylbicyclo[2.2.2]oct-1-yl]amino]acetyl]-4-fluoropyrrolidine-2-carbonitrile (42.4 mg).

MS (FAB$^+$) m/z: 569 (MH$^+$). Rf 0.50 (ethyl acetate:methanol=20:1).

Step 2:

Synthesis of (2S,4S)-4-fluoro-1-[[N-[4-(N-octylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-octylamino)carbonylbicyclo[2.2.2]oct-1-yl]amino]acetyl]-4-fluoropyrrolidine-2-carbonitrile (41.1 mg) was used to obtain (2S,4S)-4-fluoro-1-[[N-[4-(N-octylamino)carbonylbicyclo[2.2.2]oct-1-yl]amino]acetyl]pyrrolidine-2-carbonitrile (17.2 mg).

MS (FAB$^+$) m/z: 435 (MH$^+$). HRMS (FAB$^+$) for $C_{24}H_{40}FN_4O_2$ (MH$^+$): calcd, 435.3135; found, 435.3160.

EXAMPLE 47

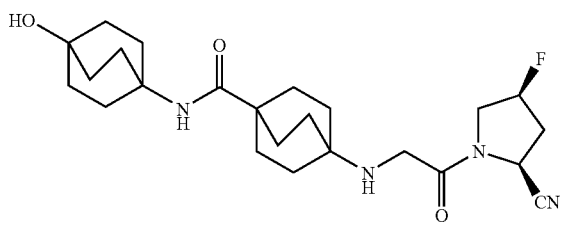

Synthesis of (2S,4S)-4-fluoro-1-[[N-[4-[N-(4-hydroxybicyclo[2.2.2]oct-1-yl)amino]carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-[N-(4-hydroxybicyclo[2.2.2]oct-1-yl)amino]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-aminobicyclo[2.2.2]octane-1-ol (13.5 mg) were used to obtain (2S,4S)-1-[[N-benzyloxycarbonyl-N-[4-[N-(4-hydroxybicyclo[2.2.2]oct-1-yl)amino]carbonylbicyclo[2.2.2]oct-1-yl]amino]acetyl]-4-fluoropyrrolidine-2-carbonitrile (31.2 mg).

MS (FAB$^+$) m/z: 581 (MH$^+$). Rf 0.38 (ethyl acetate:methanol=9:1).

Step 2:

Synthesis of (2S,4S)-4-fluoro-1-[[N-[4-[N-(4-hydroxybicyclo[2.2.2]oct-1-yl)amino]carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-[N-(4-hydroxybicyclo[2.2.2]oct-1-yl)amino]carbonylbicyclo[2.2.2]oct-1-yl]amino]acetyl]-4-fluoropyrrolidine-2-carbonitrile (28.0 mg) was used to obtain (2S,4S)-4-fluoro-1-[[N-[4-[N-(4-hydroxybicyclo[2.2.2]oct-1-yl)amino]carbonylbicyclo[2.2.2]oct-1-yl]amino]acetyl]pyrrolidine-2-carbonitrile (11.9 mg).

MS (FAB$^+$) m/z: 447 (MH$^+$). HRMS (FAB$^+$) for $C_{24}H_{36}FN_4O_3$ (MH$^+$): calcd, 447.2771; found, 447.2798.

EXAMPLE 48

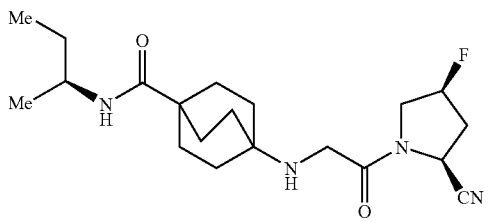

Synthesis of (2S,4S,1' S)-4-fluoro-1-[[N-[4-(N-1-methylpropylamino)carbonylbicyclo[2.2.2]oct-1-yl]amino]acetyl]pyrrolidine-2-carbonitrile Step 1:

Synthesis of (2S,4S,1' S)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (350.0 mg) and 1(S)-methylpropylamine (80.0 μL) were used to obtain (2S,4S,1' S)-1-[(N-benzyloxycarbonyl-N-[4-(N-1-methylpropylamino)carbonylbicyclo[2.2.2]oct-1-yl]amino]acetyl]-4-fluoropyrrolidine-2-carbonitrile (296.9 mg)

MS (FAB$^+$) m/z: 513 (MH$^+$). Rf 0.38 (ethyl acetate:methanol=20:1).

Step 2:

Synthesis of (2S,4S,1' S)-4-fluoro-1-[[N-[4-(N-1-methylpropylamino)carbonylbicyclo[2.2.2]oct-1-yl]amino]acetyl]pyrrolidine-2-carbonitrile In a similar manner to Example 5, (2S,4S,1' S)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile (294.0 mg) was used to obtain (2S,4S,1' S)-4-fluoro-1-[[N-[4-(N-1-methylpropylamino)carbonylbicyclo[2.2.2]oct-1-yl]amino]acetyl]pyrrolidine-2-carbonitrile (172.4 mg).

MS (FAB$^+$) m/z: 379 (MH$^+$). HRMS (FAB$^+$) for $C_{20}H_{32}FN_4O_2$ (MH$^+$): calcd, 379.2509; found, 379.2469.

EXAMPLE 49

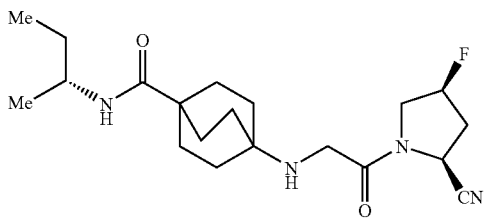

Synthesis of (2S,4S,1' R)-4-fluoro-1-[[N-[4-(N-1-methylpropylamino)carbonylbicyclo[2.2.2]oct-1-yl]amino]acetyl]pyrrolidine-2-carbonitrile Step 1:

Synthesis of (2S,4S,1' R)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (350.0 mg) and 1(R)-methylpropylamine (80.0 μL) were used to obtain (2S,4S,1' R)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile (292.4 mg)

MS (FAB$^+$) m/z: 513 (MH$^+$). Rf 0.38 (ethyl acetate:methanol=20:1).

Step 2:

Synthesis of (2S,4S,1' R)-4-fluoro-1-[[N-[4-(N-1-methylpropylamino)carbonylbicyclo[2.2.2]oct-1-yl]amino]acetyl]pyrrolidine-2-carbonitrile In a similar manner to Example 5, (2S,4S,1' R)-1-[[N-benzyloxycarbonyl-N-[4-(N-1-methylpropylamino)carbonylbicyclo[2.2.2]oct-1-yl]amino]acetyl]-4-fluoropyrrolidine-2-carbonitrile (290.0 mg) was used to obtain (2S,4S,1' R)-4-fluoro-1-[[N-[4-(N-1-methylpropylamino)carbonylbicyclo[2.2.2]oct-1-yl]amino]acetyl]pyrrolidine-2-carbonitrile (158.3 mg).

MS (FAB⁺) m/z: 379 (MH⁺). HRMS (FAB⁺) for $C_{20}H_{32}FN_4O_2$ (MH⁺): calcd, 379.2509; found, 379.2477.

EXAMPLE 50

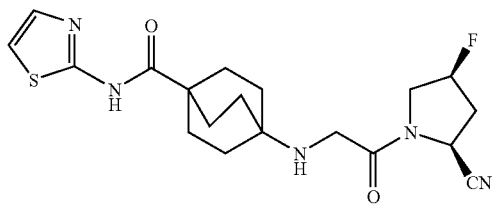

Synthesis of (2S,4S)-4-fluoro-1-[[N-[4-[N-(thiazol-2-yl)amino]carbonylbicyclo[2.2.2]oct-1-yl]amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (30.0 mg), along with 1-hydroxybenzotriazole, was dissolved in N,N-dimethylformamide (1.0 mL). To this solution, 2-aminothiazole (18.6 mg) and 1-(3-dimethylaminopropyl)-3-ethylcarbodiimide hydrochloride (53.4 mg) were added, and the mixture was stirred at room temperature for 15 hours. The solvent was evaporated under reduced pressure and the resulting residue was purified by preparative thin-layer chromatography (solvent:dichloromethane:methanol=9:1) to give (2S,4S)-4-fluoro-1-[[N-[4-[N-(thiazol-2-yl)amino]carbonylbicyclo[2.2.2]oct-1-yl]amino]acetyl]pyrrolidine-2-carbonitrile (17.4 mg).

MS (FAB⁺) m/z: 406 (MH⁺). HRMS (FAB⁺) for $C_{19}H_{25}FN_5O_2S$ (MH⁺): calcd, 406.1713; found, 406.1695.

EXAMPLE 51

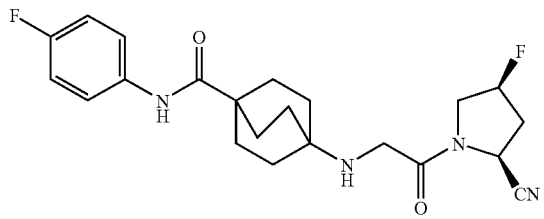

Synthesis of (2S,4S)-4-fluoro-1-[[N-[4-[N-(4-fluorophenyl)amino]carbonylbicyclo[2.2.2]oct-1-yl]amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (30.0 mg), along with 1-hydroxybenzotriazole, was dissolved in N,N-dimethylformamide (1.0 mL). While the solution was chilled in an ice bath, 1-(3-dimethylaminopropyl)-3-ethylcarbodiimide hydrochloride (53.4 mg) was added and the mixture was allowed to warm to room temperature and was stirred for 1 hour. Subsequently, 4-fluoroaniline (17.8 μL) was added and the mixture was stirred for additional 2 hours. The solvent was evaporated under reduced pressure and the resulting residue was purified by preparative thin-layer chromatography (solvent:dichloromethane:methanol=4:1) to give (2S,4S)-4-fluoro-1-[[N-[4-[N-(4-fluorophenyl)amino]carbonylbicyclo[2.2.2]oct-1-yl]amino]acetyl]pyrrolidine-2-carbonitrile (14.6 mg).

MS (FAB⁺) m/z: 417 (MH⁺). HRMS (FAB⁺) for $C_{22}H_{27}F_2N_4O_2$ (MH⁺): calcd, 417.2102; found, 417.2078.

EXAMPLE 52

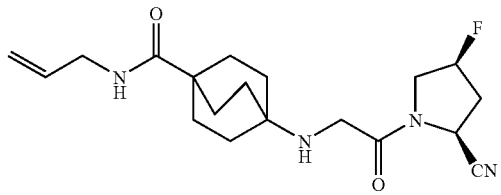

Synthesis of (2S,4S)-4-fluoro-1-[[N-[4-[N-(2-propenyl)amino]carbonylbicyclo[2.2.2]oct-1-yl]amino]acetyl]pyrrolidine-2-carbonitrile In a similar manner to Example 51, (2S,4S)-1-[[N-(4-carboxybicyclo[2.2.2]oct-1-yl)amino]acetyl]-4-fluoropyrrolidine-2-carbonitrile (30.0 mg) and allylamine (14.0 μL) were used to obtain (2S,4S)-4-fluoro-1-[[N-[4-[N-(2-propenyl)amino]carbonylbicyclo[2.2.2]oct-1-yl]amino]acetyl]pyrrolidine-2-carbonitrile (15.7 mg).

MS (FAB⁺) m/z: 363 (MH⁺). HRMS (FAB⁺) for $C_{19}H_{28}FN_4O_2$ (MH⁺): calcd, 363.2196; found, 363.2172.

EXAMPLE 53

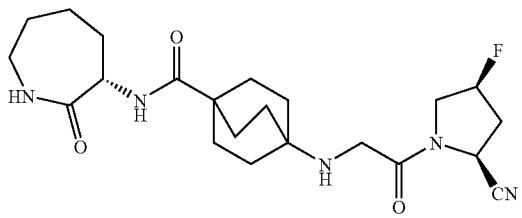

Synthesis of (2S,4S,3' S)-4-fluoro-1-[[N-[4-[N-(2-oxo-1-azacyclohept-3-yl)amino]carbonylbicyclo[2.2.2]oct-1-yl]amino]acetyl]pyrrolidine-2-carbonitrile Step 1:

Synthesis of (2S,4S,3' S)-1-[[N-benzyloxycarbonyl-[4-[N-(2-oxo-1-azacyclohept-3-yl)amino]carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and (S)-5-amino-ε-caprolactam hydrochloride (18.6 mg) were used to obtain (2S,4S,3' S)-1-[[N-benzyloxycarbonyl-[4-[N-(2-oxo-1-azacyclohept-3-yl)

amino]carbonylbicyclo[2.2.2]oct-1-yl]amino]acetyl]-4-fluoropyrrolidine-2-carbonitrile (30.3 mg).

MS (FAB$^+$) m/z: 568 (MH$^+$). Rf 0.38 (ethyl acetate:methanol=5:1).

Step 2:

Synthesis of (2S,4S,3' S)-4-fluoro-1-[[N-[4-[N-(2-oxo-1-azacyclohept-3-yl)amino]carbonylbicyclo[2.2.2]oct-1-yl]amino]acetyl]pyrrolidine-2-carbonitrile In a similar manner to Example 5, (2S,4S,3' S)-1-[[N-benzyloxycarbonyl-[4-[N-(2-oxo-1-azacyclohept-3-yl)amino]carbonylbicyclo[2.2.2]oct-1-yl]amino]acetyl]-4-fluoropyrrolidine-2-carbonitrile (28.2 mg) was used to obtain (2S,4S,3' S)-4-fluoro-1-[[N-[4-[N-(2-oxo-1-azacyclohept-3-yl)amino]carbonylbicyclo[2.2.2]oct-1-yl]amino]acetyl]pyrrolidine-2-carbonitrile (13.0 mg).

MS (FAB$^+$) m/z: 434 (MH$^+$). HRMS (FAB$^+$) for $C_{22}H_{33}FN_5O_3$ (MH$^+$): calcd, 434.2567; found, 434.2566.

EXAMPLE 54

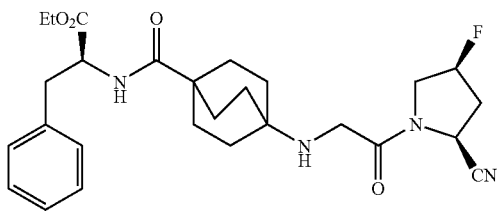

Synthesis of (2S,4S,1' S)-4-fluoro-1-[[N-[4-[N-(1-ethoxycarbonyl-2-phenylethyl)amino]carbonylbicyclo[2.2.2]oct-1-yl]amino]acetyl]pyrrolidine-2-carbonitrile Step 1:

Synthesis of (2S,4S,1' S)-1-([N-benzyloxycarbonyl-[4-[N-(1-ethoxycarbonyl-2-phenylethyl)amino]carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and L-phenylalanine ethyl ester hydrochloride (26.0 mg) were used to obtain (2S,4S,1' S)-1-[[N-benzyloxycarbonyl-[4-[N-(1-ethoxycarbonyl-2-phenylethyl)amino]carbonylbicyclo[2.2.2]oct-1-yl]amino]acetyl]-4-fluoropyrrolidine-2-carbonitrile (55.0 mg).

MS (FAB$^+$) m/z: 633 (MH$^+$). Rf 0.48 (ethyl acetate).

Step 2:

Synthesis of (2S,4S,1' S)-1-[[N-[4-[N-(1-ethoxycarbonyl-2-phenylethyl)amino]carbonylbicyclo[2.2.2]oct-1-yl]amino]acetyl]-4-fluoropyrrolidine-2-carbonitrile In a similar manner to Example 5, (2S,4S,3' S)-1-[[N-benzyloxycarbonyl-[4-[N-(1-ethoxycarbonyl-2-phenyl-ethyl)amino]carbonylbicyclo[2.2.2]oct-1-yl]amino]acetyl]-4-fluoropyrrolidine-2-carbonitrile (53.0 mg) was used to obtain (2S,4S,3' S)-1-[[N-[4-[N-(1-ethoxycarbonyl-2-phenylethyl)amino]carbonylbicyclo[2.2.2]oct-1-yl]amino]acetyl]-4-fluoropyrrolidine-2-carbonitrile (16.0 mg).

MS (FAB$^+$) m/z: 499 (MH$^+$). HRMS (FAB$^+$) for $C_{27}H_{36}FN_4O_4$ (MH$^+$): calcd, 499.2721; found, 499.2729.

EXAMPLE 55

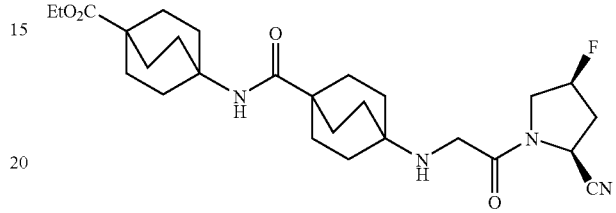

Synthesis of (2S,4S)-4-fluoro-1-[[N-[4-[N-(4-ethoxycarbonylbicyclo[2.2.2]oct-1-yl)amino]carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-[N-(4-ethoxycarbonylbicyclo[2.2.2]oct-1-yl)amino]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and ethyl 4-aminobicyclo[2.2.2]octane-1-carboxylate (22.3 mg) were used to obtain (2S,4S)-1-[[N-benzyloxycarbonyl-N-[4-[N-(4-ethoxycarbonylbicyclo[2.2.2]oct-1-yl)amino]carbonylbicyclo[2.2.2]oct-1-yl]amino]acetyl]-4-fluoropyrrolidine-2-carbonitrile (40.7 mg).

MS (FAB$^+$) m/z: 637 (MH$^+$). Rf 0.40 (ethyl acetate).

Step 2:

Synthesis of (2S,4S)-4-fluoro-1-[[N-[4-[N-(4-ethoxycarbonylbicyclo[2.2.2]oct-1-yl)amino]carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-[N-(4-ethoxycarbonylbicyclo[2.2.2]oct-1-yl)amino]carbonylbicyclo[2.2.2]oct-1-yl]amino]acetyl]-4-fluoropyrrolidine-2-carbonitrile (38.7 mg) was used to obtain (2S,4S)-4-fluoro-1-[[N-[4-[N-(4-ethoxycarbonylbicyclo[2.2.2]oct-1-yl)amino]carbonylbicyclo[2.2.2]oct-1-yl]amino]acetyl]pyrrolidine-2-carbonitrile (22.3 mg).

MS (FAB$^+$) m/z: 503 (MH$^+$). HRMS (FAB$^+$) for $C_{27}H_{40}FN_4O_4$ (MH$^+$): calcd, 503.3034; found, 503.3080.

EXAMPLE 56

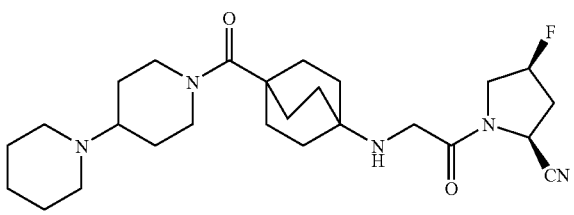

Synthesis of (2S,4S)-4-fluoro-1-[[N-[4-[4-(piperidin-1-yl)piperidin-1-yl]carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-[4-(piperidin-1-yl)piperidin-1-yl]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-(piperidin-1-yl)piperidine (22.0 mg) were used to obtain (2S,4S)-1-[[N-benzyloxycarbonyl-N-[4-[4-(piperidin-1-yl)piperidin-1-yl]carbonylbicyclo[2.2.2]oct-1-yl]amino]acetyl]-4-fluoropyrrolidine-2-carbonitrile (44.9 mg).

MS (FAB$^+$) m/z: 608 (MH$^+$). HRMS (FAB$^+$) for $C_{34}H_{47}FN_5O_4$ (MH$^+$): calcd, 608.3612; found, 608.3583.

Step 2:

Synthesis of (2S,4S)-4-fluoro-1-[[N-[4-[4-(piperidin-1-yl)piperidin-1-yl]carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-[4-(piperidin-1-yl)piperidin-1-yl]carbonylbicyclo[2.2.2]oct-1-yl]amino]acetyl]-4-fluoropyrrolidine-2-carbonitrile (44.9 mg) was used to obtain (2S,4S)-4-fluoro-1-[[N-[4-[4-(piperidin-1-yl)piperidin-1-yl]carbonylbicyclo[2.2.2]oct-1-yl]amino]acetyl]pyrrolidine-2-carbonitrile (15.5 mg).

MS (FAB$^+$) m/z: 474 (MH$^+$). HRMS (FAB$^+$) for $C_{26}H_{41}FN_5O_2$ (MH$^+$): calcd, 474.3244; found, 474.3234.

EXAMPLE 57

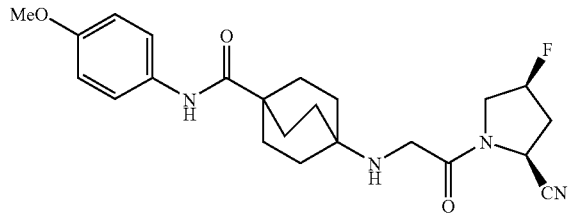

Synthesis of (2S,4S)-4-fluoro-1-[[N-[4-[N-(4-methoxyphenyl)amino]carbonylbicyclo[2.2.2]oct-1-yl]amino]acetyl]pyrrolidine-2-carbonitrile In a similar manner to Example 51, (2S,4S)-1-[[N-(4-carboxybicyclo[2.2.2]oct-1-yl)amino]acetyl]-4-fluoropyrrolidine-2-carbonitrile (30.0 mg) and 4-methoxyphenylaniline (22.9 mg) were used to obtain (2S,4S)-4-fluoro-1-[[N-[4-[N-(4-methoxyphenyl)amino]carbonylbicyclo[2.2.2]oct-1-yl]amino]acetyl]pyrrolidine-2-carbonitrile (19.7 mg).

MS (FAB$^+$) m/z: 429 (MH$^+$). HRMS (FAB$^+$) for $C_{23}H_{30}FN_4O_3$ (MH$^+$): calcd, 429.2302; found, 429.2330.

EXAMPLE 58

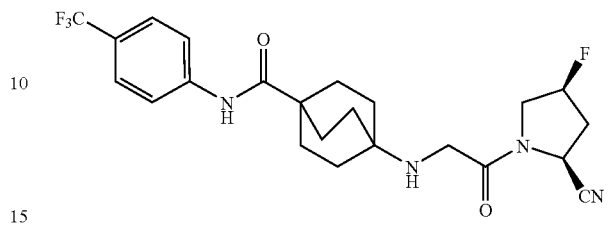

Synthesis of (2S,4S)-4-fluoro-1-[[N-[4-[N-(4-trifluoromethylphenyl)amino]carbonylbicyclo[2.2.2]oct-1-yl]amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (30.0 mg), along with 1-hydroxybenzotriazole, was dissolved in N,N-dimethylformamide (1.0 mL). While the solution was chilled in an ice bath, 1-(3-dimethylaminopropyl)-3-ethylcarbodiimide hydrochloride (53.4 mg) was added and the mixture was allowed to warm to room temperature and was stirred for 1 hour. Subsequently, 4-trifluoromethylaniline (23.0 µL) was added and the mixture was stirred for additional 12 hours, followed by addition of dimethylaminopyridine (11.3 mg) and stirring for additional 24 hours. The solvent was then evaporated under reduced pressure and the resulting residue was purified by preparative thin-layer chromatography (solvent:dichloromethane:methanol=4:1) to give (2S,4S)-4-fluoro-1-[[N-[4-[N-(4-trifluoromethylphenyl)amino]carbonylbicyclo[2.2.2]oct-1-yl]amino]acetyl]pyrrolidine-2-carbonitrile (10.1 mg).

MS (FAB$^+$) m/z: 467 (MH$^+$). HRMS (FAB$^+$) for $C_{23}H_{27}F_4N_4O_2$ (MH$^+$): calcd, 467.2070; found, 467.2051.

EXAMPLE 59

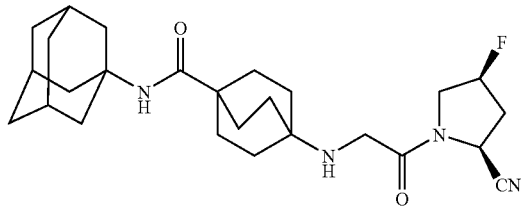

Synthesis of (2S,4S)-4-fluoro-1-[[N-[4-(N-adamantylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-adamantylamino)carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo

[2.2.2]oct-1-yl]amino]acetyl]-4-fluoropyrrolidine-2-carbonitrile (50.0 mg) and adamantanamine (17.1 mg) were used to obtain (2S,4S)-1-[[N-benzyloxycarbonyl-N-[4-(N-adamantylamino)carbonylbicyclo[2.2.2]oct-1-yl]amino]acetyl]-4-fluoropyrrolidine-2-carbonitrile (38.2 mg).

MS (FAB⁺) m/z: 591 (MH⁺). Rf 0.30 (ethyl acetate:hexane=4:1).

Step 2:

Synthesis of (2S,4S)-4-fluoro-1-[[N-[4-(N-adamantylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-adamantylamino)carbonylbicyclo[2.2.2]oct-1-yl]amino]acetyl]-4-fluoropyrrolidine-2-carbonitrile (36.2 mg) was used to obtain (2S,4S)-4-fluoro-1-[[N-[4-(N-adamantylamino)carbonylbicyclo[2.2.2]oct-1-yl]amino]acetyl]pyrrolidine-2-carbonitrile (17.4 mg).

MS (FAB⁺) m/z: 457 (MH⁺). HRMS (FAB⁺) for $C_{26}H_{38}FN_4O_2$ (MH⁺): calcd, 457.2979; found, 457.2990.

EXAMPLE 60

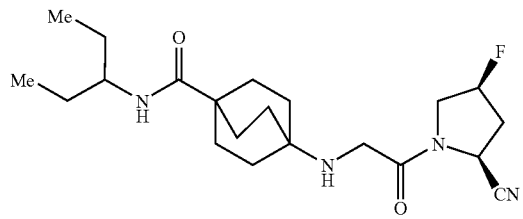

Synthesis of (2S,4S)-4-fluoro-1-[[N-[4-(N-1-ethylpropylamino)carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-(N-1-ethylpropylamino)carbonylbicyclo[2.2.2]oct-1-yl]amino]acetyl]-4-fluoropyrrolidine-2-carbonitrile (2S,4S)-1-[[N-Benzyloxycarbonyl-N-[4-carboxybicyclo[2.2.2]oct-1-yl]amino]acetyl]-4-fluoropyrrolidine-2-carbonitrile (40.0 mg), along with 1-hydroxybenzotriazole, was dissolved in N,N-dimethylformamide (0.8 mL). While the solution was chilled in an ice bath, 1-(3-dimethylaminopropyl)-3-ethylcarbodiimide hydrochloride (41.9 mg) was added and the mixture was allowed to warm to room temperature and was stirred for 2 hours. Subsequently, 1-ethylpropylamine (13.2 μL) was added and the mixture was stirred for additional 17 hours. The solvent was evaporated under reduced pressure and the resulting residue was dissolved in dichloromethane. The organic layer washed sequentially with 0.1 N aqueous hydrochloric acid, saturated aqueous sodium bicarbonate solution and saturated brine. The organic layer was then dried over sodium sulfate and was concentrated under reduced pressure. The residue was purified by column chromatography (eluant:ethyl acetate) to give (2S,4S)-1-[[N-benzyloxycarbonyl-N-[4-(N-1-ethylpropylamino)carbonylbicyclo[2.2.2]oct-1-yl]amino]acetyl]-4-fluoropyrrolidine-2-carbonitrile (46.0 mg).

MS (FAB⁺) m/z: 527 (MH⁺). Rf 0.33 (ethyl acetate).

Step 2:

Synthesis of (2S,4S)-4-fluoro-1-[[N-[4-(N-1-ethylpropylamino)carbonylbicyclo[2.2.2]oct-1-yl]amino]acetyl]pyrrolidine-2-carbonitrile In a similar manner to Example 5, (2S,4S)-1-[[N-benzyloxycarbonyl-N-[4-(N-1-ethylpropylamino)carbonylbicyclo[2.2.2]oct-1-yl]amino]acetyl]-4-fluoropyrrolidine-2-carbonitrile (46.0 mg) was used to obtain (2S,4S)-4-fluoro-1-[[N-[4-(N-1-ethylpropylamino)carbonylbicyclo[2.2.2]oct-1-yl]amino]acetyl]pyrrolidine-2-carbonitrile (22.5 mg).

MS (FAB⁺) m/z: 393 (MH⁺). HRMS (FAB⁺) for $C_{21}H_{34}FN_4O_2$ (MH⁺): calcd, 393.2666; found, 393.2670.

EXAMPLE 61

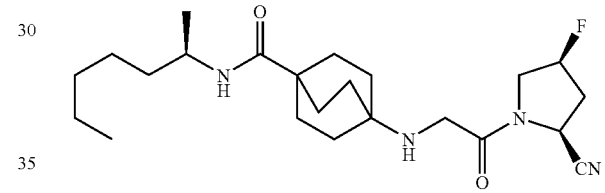

Synthesis of (2S,4S)-4-fluoro-1-[[N-[4-[(2R)—N-(2-heptyl)amino]carbonylbicyclo[2.2.2]oct-1-yl]amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (50.0 mg), 1-hydroxybenzotriazole (23.7 mg), JANDAJEL-1-(3-dimethylaminopropyl)-3-ethylcarbodiimide (289 mg) and N,N-dimethylformamide (1 mL) were mixed together and the mixture was stirred at room temperature for 3 hours. Subsequently, (2R)-2-aminoheptane (46.6 μL) was added and the mixture was stirred at room temperature for 17 hours and 40 minutes. This was followed by addition of dichloromethane (0.5 mL) and (2R)-2-aminoheptane (11.6 μL), stirring at room temperature for 4.5 hours, addition of JANDAJEL-1-(3-dimethylaminopropyl)-3-ethylcarbodiimide (96.6 mg) and additional stirring at room temperature for 17 hours. Subsequently, (isocyanatomethyl)polystyrene (232 mg) was added and the mixture was stirred at room temperature for 2 hours. The insoluble material was filtered and the filtrate was concentrated under reduced pressure. The resulting residue was then purified by silica gel column (eluant:ethyl acetate: methanol=10:1) to give (2S,4S)-4-fluoro-1-[[N-[4-[(2R)—N-(2-heptyl)amino]carbonylbicyclo[2.2.2]oct-1-yl]amino]acetyl]pyrrolidine-2-carbonitrile (9.0 mg).

MS (FAB⁺) m/z: 421 (MH⁺). HRMS (FAB⁺) for $C_{23}H_{38}FN_4O_2$ (MH⁺): calcd, 421.2979; found, 421.2983.

EXAMPLE 62

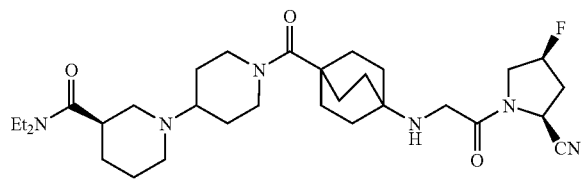

Synthesis of (2S,4S)-1-[[N-[4-[4-[(3R)-3-(N,N-diethylcarbamoyl)piperidin-1-yl]piperidin-1-yl]carbonylbicyclo[2.2.2]oct-1-yl]amino]acetyl]-4-fluoropyrrolidine-2-carbonitrile Step 1:

Synthesis of (2S,4S)-1-[[N-benzyloxycarbonyl-N-[4-[4-[(3R)-3-N,N-diethylcarbamoylpiperidin-1-yl]piperidin-1-yl]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (74.9 mg) and (3R)—N,N-diethyl-1-(piperidin-4-yl)piperidine-3-carboxamide (61.0 mg) were used to obtain (2S,4S)-1-[[N-benzyloxycarbonyl-N-[4-[4-[(3R)-3-(N,N-diethylcarbamoyl)piperidin-1-yl]piperidin-1-yl]carbonylbicyclo[2.2.2]oct-1-yl]amino]acetyl]-4-fluoropyrrolidine-2-carbonitrile (71.7 mg).

MS (FAB$^+$) m/z: 707 (MH$^+$). HRMS (FAB$^+$) for $C_{39}H_{56}FN_6O_5$ (MH$^+$): calcd, 707.4296; found, 707.4294.

Step 2:

Synthesis of (2S,4S)-1-[[N-[4-[4-[(3R)-3-(N,N-diethylcarbamoyl)piperidin-1-yl]piperidin-1-yl]carbonylbicyclo[2.2.2]oct-1-yl]amino]acetyl]-4-fluoropyrrolidine-2-carbonitrile In a similar manner to Example 5, (2S,4S)-4-fluoro-1-[[N-benzyloxycarbonyl-N-[4-[4-[(3R)-3-(N,N-diethylcarbamoyl)piperidin-1-yl]piperidin-1-yl]carbonylbicyclo[2.2.2]oct-1-yl]amino]acetyl]pyrrolidine-2-carbonitrile (66.7 mg) was used to obtain (2S,4S)-1-[[N-[4-[4-[(3R)-3-(N,N-diethylcarbamoyl)piperidin-1-yl]piperidin-1-yl]carbonylbicyclo[2.2.2]oct-1-yl]amino]acetyl]-4-fluoropyrrolidine-2-carbonitrile (31.4 mg).

MS (FAB$^+$) m/z: 573 (MH$^+$). HRMS (FAB$^+$) for $C_{31}H_{50}FN_6O_3$ (MH$^+$): calcd, 573.3928; found, 573.3905.

EXAMPLE 63

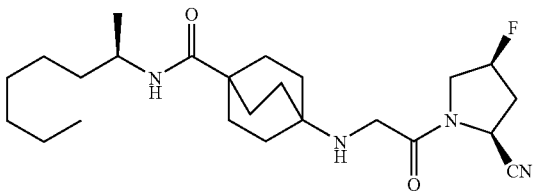

Synthesis of (2S,4S)-4-fluoro-1-[[N-[4-[(2R)—N-(2-octyl)amino]carbonylbicyclo[2.2.2]oct-1-yl]amino]acetyl]pyrrolidine-2-carbonitrile (2S,4S)-1-[[N-(4-carboxybicyclo[2.2.2]oct-1-yl)amino]acetyl]-4-fluoropyrrolidine-2-carbonitrile (50.0 mg) was suspended in dichloromethane (1 mL). To the suspension, trichloroacetonitrile (31.0 μL) and triphenylphosphine (81.1 mg) in dichloromethane (0.5 mL) were added and the mixture was stirred at room temperature for 2 hours. Subsequently, (piperidinomethyl)polystyrene (150 mg) and (2R)-2-aminooctane (57.1 μL) were sequentially added at 0° C. and the mixture was stirred at room temperature for 21 hours. This was followed by addition of (isocyanatomethyl)polystyrene (232 mg), stirring at room temperature for 1 hour, addition of water (3 mL) and dichloromethane (2 mL), and further stirring at room temperature for 50 minutes. The reaction mixture was then loaded onto an Isolute HM-N column and was extracted 5 times with 2 ml dichloromethane. The dichloromethane extracts were combined and concentrated under reduced pressure. The resulting residue was purified by silica gel column (eluant:dichloromethane:methanol=50:1) to give (2S,4S)-4-fluoro-1-[[N-[4-[(2R)—N-(2-octyl)amino]carbonylbicyclo[2.2.2]oct-1-yl]amino]acetyl]pyrrolidine-2-carbonitrile (30.3 mg).

MS (FAB$^+$) m/z: 435 (MH$^+$). HRMS (FAB$^+$) for $C_{24}H_{40}FN_4O_2$ (MH$^+$): calcd, 435.3135; found, 435.3103.

EXAMPLE 64

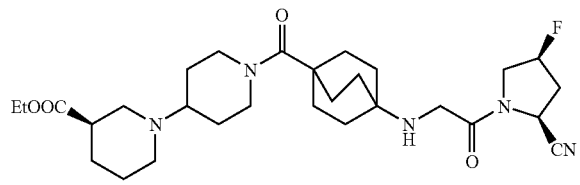

Synthesis of (2S,4S)-1-[[N-[4-[4-[(3R)-3-ethoxycarbonylpiperidin-1-yl]piperidin-1-yl]carbonylbicyclo[2.2.2]oct-1-yl]amino]acetyl]-4-fluoropyrrolidine-2-carbonitrile Step 1:

Synthesis of (2S,4S)-1-([N-benzyloxycarbonyl-N-[4-[4-[(3R)-3-ethoxycarbonylpiperidin-1-yl]piperidin-1-yl]carbonylbicyclo[2.2.2]oct-1-yl]amino]acetyl]-4-fluoropyrrolidine-2-carbonitrile In a similar manner to Example 4, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (101 mg) and ethyl (3R)-1-(piperidin-4-yl)piperidine-3-carboxylate (84.3 mg) were used to obtain (2S,4S)-1-[[N-benzyloxycarbonyl-N-[4-[4-[(3R)-3-ethoxycarbonylpiperidin-1-yl]piperidin-1-yl]carbonylbicyclo[2.2.2]oct-1-yl]amino]acetyl]-4-fluoropyrrolidine-2-carbonitrile (115 mg).

MS (FAB$^+$) m/z: 680 (MH$^+$). HRMS (FAB$^+$) for $C_{37}H_{51}FN_5O_6$ (MH$^+$): calcd, 680.3823; found, 680.3824.

Step 2:

Synthesis of (2S,4S)-1-[[N-[4-[4-[(3R)-3-ethoxycarbonylpiperidin-1-yl]piperidin-1-yl]carbonylbicyclo[2.2.2]oct-1-yl]amino]acetyl]-4-fluoropyrrolidine-2-carbonitrile In a similar manner to Example 5, (2S,4S)-1-[[N-benzyloxycarbonyl-N-[4-[4-[(3R)-3-ethoxycarbonylpiperidin-1-yl]piperidin-1-yl]carbonylbicyclo[2.2.2]oct-1-yl]amino]acetyl]-4-fluoropyrrolidine-2-carbonitrile (110 mg) was used to obtain (2S,4S)-1-[[N-[4-[4-[(3R)-3-ethoxycarbonylpiperidin-1-yl]piperidin-1-yl]carbonylbicyclo[2.2.2]oct-1-yl]amino]acetyl]-4-fluoropyrrolidine-2-carbonitrile (36.0 mg).

MS (FAB$^+$) m/z: 546 (MH$^+$). HRMS (FAB$^+$) for $C_{29}H_{45}FN_5O_4$ (MH$^+$): calcd, 546.3456; found, 546.3452.

EXAMPLE 65

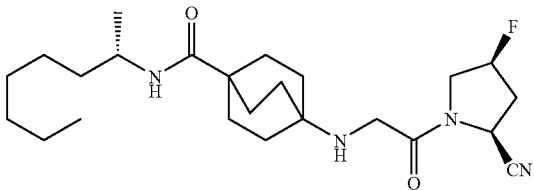

Synthesis of (2S,4S)-4-fluoro-1-[[N-[4-[N-[(2S)-2-octyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)]amino]acetyl]-4-fluoropyrrolidine-2-carbonitrile (50.0 mg) and (2S)-aminooctane (57.1 µL) were used to obtain (2S,4S)-4-fluoro-1-[[N-[4-[N-[(2S)-2-octyl]amino]carbonylbicyclo[2.2.2]oct-1-yl]amino]acetyl]pyrrolidine-2-carbonitrile (13.4 mg).

MS (FAB$^+$) m/z: 435 (MH$^+$). HRMS (FAB$^+$) for $C_{24}H_{40}FN_4O_2$ (MH$^+$): calcd, 435.3135; found, 435.3163.

EXAMPLE 66

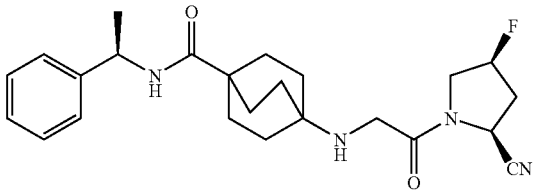

Synthesis of (2S,4S)-4-fluoro-1-[[N-[4-[N-[(1R)-1-phenyl-1-ethyl]amino]carbonylbicyclo[2.2.2]oct-1-yl)amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and (1R)-1-phenylethylamine (43.4 µL) were used to obtain (2S,4S)-4-fluoro-1-[[N-[4-[N-[(1R)-1-phenyl-1-ethyl]amino]carbonylbicyclo[2.2.2]oct-1-yl]amino]acetyl]pyrrolidine-2-carbonitrile (22.8 mg).

MS (FAB$^+$) m/z: 427 (MH$^+$). HRMS (FAB$^+$) for $C_{24}H_{32}FN_4O_2$ (MH$^+$): calcd, 427.2509; found, 427.2511.

EXAMPLE 67

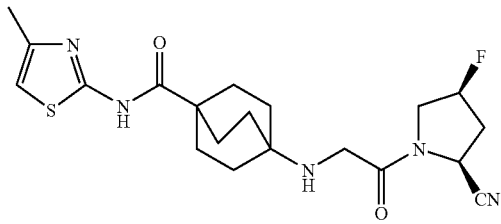

Synthesis of (2S,4S)-4-fluoro-1-[[N-[4-[N-(4-methylthiazol-2-yl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-amino-4-methylthiazole (38.8 mg) were used to obtain (2S,4S)-4-fluoro-1-[[N-[4-[N-(4-methylthiazol-2-yl)amino]carbonylbicyclo[2.2.2]oct-1-yl]amino]acetyl]pyrrolidine-2-carbonitrile (11.5 mg).

MS (FAB$^+$) m/z: 420 (MH$^+$). HRMS (FAB$^+$) for $C_{20}H_{27}FN_5O_2S$ (MH$^+$): calcd, 420.1870; found, 420.1837.

EXAMPLE 68

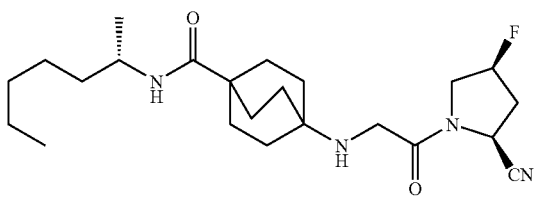

Synthesis of (2S,4S)-4-fluoro-1-[[N-[4-[N-[(2S)-2-heptyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and (2S)-aminoheptane (51.1 µL) were used to obtain (2S,4S)-4-fluoro-1-[[N-[4-[N-[(2S)-2-heptyl]amino]carbonylbicyclo[2.2.2]oct-1-yl]amino]acetyl]pyrrolidine-2-carbonitrile (22.5 mg).

MS (FAB$^+$) m/z: 421 (MH$^+$). HRMS (FAB$^+$) for $C_{23}H_{38}FN_4O_2$ (MH$^+$): calcd, 421.2979; found, 421.2983.

EXAMPLE 69

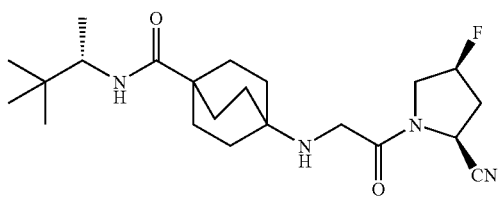

Synthesis of (2S,4S)-4-fluoro-1-[[N-[4-[N-[(2S)-3,3-dimethyl-2-butyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and (2S)-3,3-dimethyl-2-butylamine (41.4 µL) were used to obtain (2S,4S)-4-fluoro-1-[[N-[4-[N-[(2S)-3,3-dimethyl-2-butyl]amino]carbonylbicyclo[2.2.2]oct-1-yl]amino]acetyl]pyrrolidine-2-carbonitrile (20.5 mg).

EXAMPLE 70

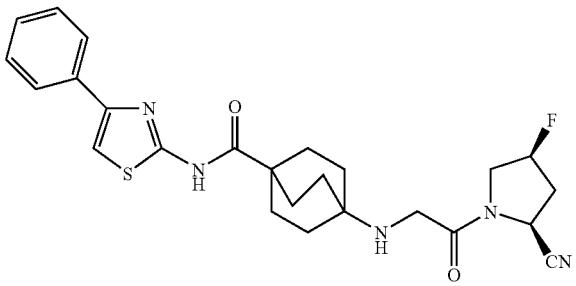

Synthesis of (2S,4S)-4-fluoro-1-[[N-[4-[N-(4-phenylthiazol-2-yl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and (2S,4S)-4-fluoro-1-[[N-[4-[N-(4-phenylthiazol-2-yl)amino]carbonylbicyclo[2.2.2]oct-1-yl]amino]acetyl]pyrrolidine-2-carbonitrile (32.7 mg) were obtained.

MS (FAB$^+$) m/z: 482 (MH$^+$). HRMS (FAB$^+$) for $C_{25}H_{29}FN_5O_2S$ (MH$^+$): calcd, 482.2026; found, 482.2018.

EXAMPLE 71

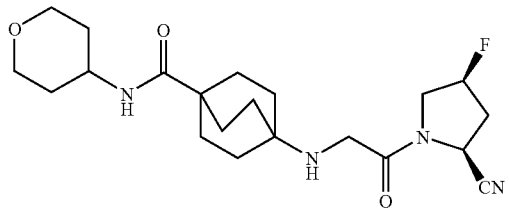

Synthesis of (2S,4S)-4-fluoro-1-[[N-[(tetrahydropyran-4-yl)amino]carbonylbicyclo[2.2.2]oct-1-yl]amino]acetyl]pyrrolidine-2-carbonitrile Step 1:

Synthesis of (2S,4S)-1-[[N-benzyloxycarbonyl-N-[(tetrahydropyran-4-yl)amino]carbonylbicyclo[2.2.2]oct-1-yl]amino]acetyl]-4-fluoropyrrolidine-2-carbonitrile In a similar manner to Example 13, (2S,4S)-1-[[N-benzyloxycarbonyl-N-[4-(benzotriazol-1-yl)oxycarbonylbicyclo[2.2.2]oct-1-yl]amino]acetyl]-4-fluoropyrrolidine-2-carbonitrile (50.0 mg) and 4-aminotetrahydrofuran hydrochloride (15.5 mg) were used to obtain (2S,4S)-1-[[N-benzyloxycarbonyl-N-[(tetrahydropyran-4-yl)amino]carbonylbicyclo[2.2.2]oct-1-yl]amino]acetyl]-4-fluoropyrrolidine-2-carbonitrile (46.4 mg).

MS (FAB$^+$) m/z: 541 (MH$^+$).

Step 2:

Synthesis of (2S,4S)-4-fluoro-1-[[N-[(tetrahydropyran-4-yl)amino]carbonylbicyclo[2.2.2]oct-1-yl]amino]acetyl]pyrrolidine-2-carbonitrile In a similar manner to Example 5, (2S,4S)-1-[[N-benzyloxycarbonyl-N-[(tetrahydropyran-4-yl)amino]carbonylbicyclo[2.2.2]oct-1-yl]amino]acetyl]-4-fluoropyrrolidine-2-carbonitrile (44.4 mg) was used to obtain (2S,4S)-4-fluoro-1-[[N-[(tetrahydropyran-4-yl)amino]carbonylbicyclo[2.2.2]oct-1-yl]amino]acetyl]pyrrolidine-2-carbonitrile (13.5 mg).

MS (FAB$^+$) m/z: 407 (MH$^+$). HRMS (FAB$^+$) for $C_{21}H_{32}FN_4O_3$ (MH$^+$): calcd, 407.2458; found, 407.2410.

EXAMPLE 72

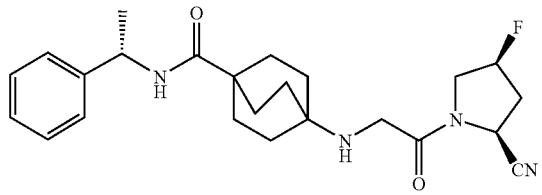

Synthesis of (2S,4S)-4-fluoro-1-[[N-[4-[N-[(1S)-1-phenyl-1-ethyl]amino]carbonylbicyclo[2.2.2]oct-1-yl]amino]acetyl]pyrrolidine-2-carbonitrile Step 1:

Synthesis of (2S,4S)-1-[[N-benzyloxycarbonyl-N-[4-[N-[(1S)-1-phenyl-1-ethyl]amino]carbonylbicyclo[2.2.2]oct-1-yl]amino]acetyl]-4-fluoropyrrolidine-2-carbonitrile (2S,4S)-1-[[N-Benzyloxycarbonyl-N-(4-carboxybicyclo[2.2.2]oct-1-yl)amino]acetyl]-4-fluoropyrrolidine-2-carbonitrile (40.0 mg) and 1-hydroxybenzotriazole (20.1 mg) were dissolved in N,N-dimethylformamide (0.8 mL). While the solution was chilled in an ice bath, 1-(3-dimethylaminopropyl)-3-ethylcarbodiimide hydrochloride (41.9 mg) was added and the mixture was stirred at room temperature for 2 hours. Subsequently, (1S)-1-phenylethylamine (14.5 μL) was added and the mixture was further stirred at room temperature for 16.5 hours. The reaction mixture was concentrated under reduced pressure and the resulting residue was dissolved in dichloromethane (2 mL). The dichloromethane solution washed sequentially with 0.1 mol/L hydrochloric acid, saturated aqueous sodium bicarbonate solution and saturated brine. The solution then was dried over anhydrous sodium sulfate and was concentrated under reduced pressure. The resulting residue was purified by a silica gel column (eluant: ethyl acetate) to give ((2S,4S)-1-[[N-benzyloxycarbonyl-N-[4-[N-[(1S)-1-phenyl-1-ethyl]amino]carbonylbicyclo[2.2.2]oct-1-yl]amino]acetyl]-4-fluoropyrrolidine-2-carbonitrile (51.5 mg).

MS (FAB$^+$) m/z: 561 (MH$^+$). HRMS (FAB$^+$) for $C_{32}H_{38}FN_4O_4$ (MH$^+$): calcd, 561.2877; found, 561.2860.

Step 2:

Synthesis of (2S,4S)-4-fluoro-1-[[N-[4-[N-[(1S)-1-phenyl-1-ethyl]amino]carbonylbicyclo[2.2.2]oct-1-yl]amino]acetyl]pyrrolidine-2-carbonitrile In a similar manner to Example 5, (2S,4S)-1-[[N-benzyloxycarbonyl-N-(4-[(1S)—N-(1-phenyl-1-ethyl)amino]carbonylbicyclo[2.2.2]oct-1-yl)amino]acetyl]-4-fluoropyrrolidine-2-carbonitrile (49.0 mg) was used to obtain (2S,4S)-4-fluoro-1-[[N-[4-[N-[(1S)-1-phenyl-1-ethyl]amino]carbonylbicyclo[2.2.2]oct-1-yl]amino]acetyl]pyrrolidine-2-carbonitrile (24.2 mg).

MS (FAB$^+$) m/z: 407 (MH$^+$). HRMS (FAB$^+$) for $C_{22}H_{36}FN_4O_2$ (MH$^+$): calcd, 407.2822; found, 407.2809.

MS (FAB+) m/z: 427 (MH+). HRMS (FAB+) for $C_{24}H_{32}FN_4O_2$ (MH+): calcd, 427.2509; found, 427.2502.

EXAMPLE 73

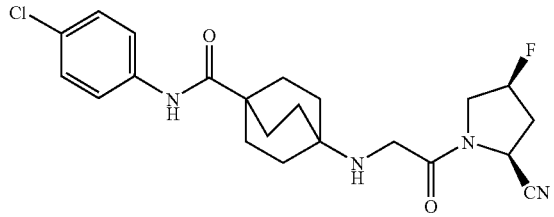

Synthesis of (2S,4S)-1-[[N-[4-[N-(4-chlorophenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-chloroaniline (43.0 mg) were used to obtain (2S,4S)-1-[[N-[4-[N-(4-chlorophenyl)amino]carbonylbicyclo[2.2.2]oct-1-yl]amino]acetyl]-4-fluoropyrrolidine-2-carbonitrile (25.6 mg).

MS (FAB+) m/z: 433 (MH+). HRMS (FAB+) for $C_{22}H_{27}ClFN_4O_2$ (MH+): calcd, 433.1807; found, 433.1816.

EXAMPLE 74

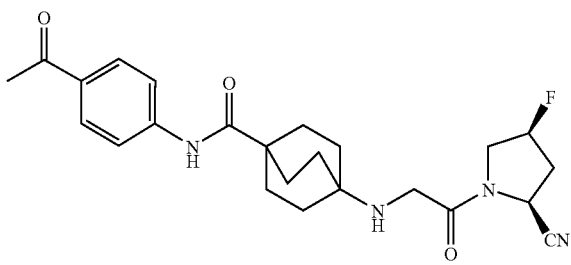

Synthesis of (2S,4S)-1-[[N-[4-[N-(4-acetylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminoacetophenone (46.0 mg) were used to obtain (2S,4S)-1-[[N-[4-[N-(4-acetylphenyl)amino]carbonylbicyclo[2.2.2]oct-1-yl]amino]acetyl]-4-fluoropyrrolidine-2-carbonitrile (24.4 mg).

MS (FAB+) m/z: 441 (MH+). HRMS (FAB+) for $C_{24}H_{30}FN_4O_3$ (MH+): calcd, 441.2302; found, 441.2291.

EXAMPLE 75

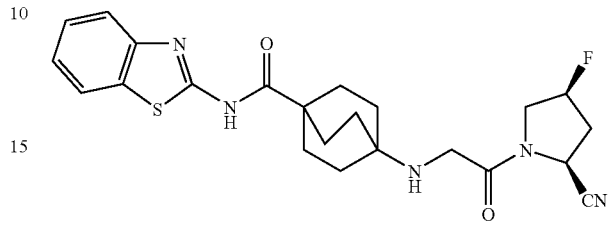

Synthesis of (2S,4S)-1-[[N-[4-[N-(benzathiazol-2-yl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-aminobenzothiazole (51.1 mg) was used to obtain (2S,4S)-1-[[N-[4-[N-(benzathiazol-2-yl)amino]carbonylbicyclo[2.2.2]oct-1-yl]amino]acetyl]-4-fluoropyrrolidine-2-carbonitrile (28.0 mg).

MS (FAB+) m/z: 456 (MH+). HRMS (FAB+) for $C_{23}H_{27}FN_5O_2S$ (MH+): calcd, 456.1870; found, 456.1881.

EXAMPLE 76

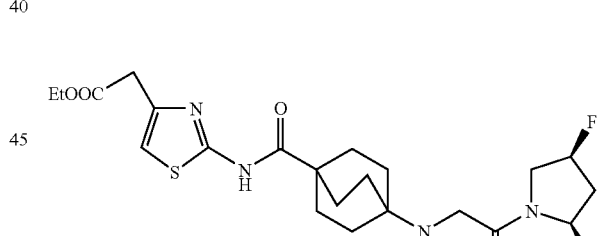

Synthesis of (2S,4S)-1-[[N-[4-[N-(4-ethoxycarbonylmethylthiazol-2-yl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and ethy 2-aminothiazole-4-acetate (63.3 mg) were used to obtain (2S,4S)-1-[[N-[4-[N-(4-ethoxycarbonylmethylthiazol-2-yl)amino]carbonylbicyclo[2.2.2]oct-1-yl]amino]acetyl]-4-fluoropyrrolidine-2-carbonitrile (11.2 mg).

MS (FAB+) m/z: 492 (MH+). HRMS (FAB+) for C$_{23}$H$_{31}$FN$_5$O$_4$S (MH+): calcd, 492.2081; found, 492.2104.

EXAMPLE 77

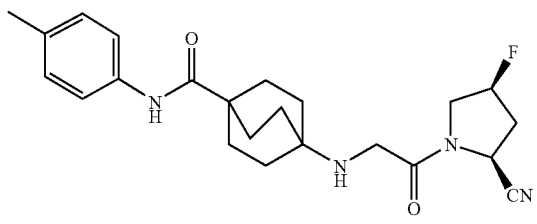

Synthesis of (2S,4S)-4-fluoro-1-[[N-[4-[N-(4-methylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and p-toluidine (36.0 mg) were used to obtain (2S,4S)-4-fluoro-1-[[N-[4-[N-(4-methylphenyl)amino]carbonylbicyclo[2.2.2]oct-1-yl]amino]acetyl]pyrrolidine-2-carbonitrile (14.2 mg).

MS (FAB+) m/z: 413 (MH+). HRMS (FAB+) for C$_{23}$H$_{30}$FN$_4$O$_2$ (MH+): calcd, 413.2353; found, 413.2378.

EXAMPLE 78

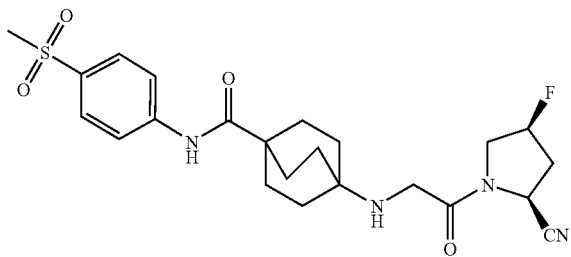

Synthesis of (2S,4S)-4-fluoro-1-[[N-[4-[N-(4-methylsulfonylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-methylsulfonylaniline hydrochloride (71.0 mg) were used to obtain ((2S,4S)-4-fluoro-1-[[N-[4-[N-(4-methylsulfonylphenyl)amino]carbonylbicyclo[2.2.2]oct-1-yl]amino]acetyl]pyrrolidine-2-carbonitrile (13.8 mg).

MS (FAB+) m/z: 477 (MH+). HRMS (FAB+) for C$_{23}$H$_{30}$FN$_4$O$_4$S (MH+): calcd, 477.1972; found, 477.1984.

EXAMPLE 79

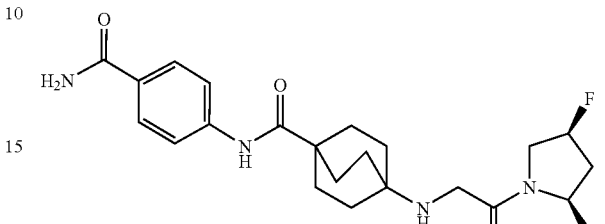

Synthesis of (2S,4S)-1-[[N-[4-[N-(4-carbamoylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminobenzamide (46.0 mg) were used to obtain (2S,4S)-1-[[N-[4-[N-(4-carbamoylphenyl)amino]carbonylbicyclo[2.2.2]oct-1-yl]amino]acetyl]-4-fluoropyrrolidine-2-carbonitrile (13.2 mg).

MS (FAB+) m/z: 442 (MH+). HRMS (FAB+) for C$_{23}$H$_{29}$FN$_5$O$_3$ (MH+): calcd, 442.2254; found, 442.2268.

EXAMPLE 80

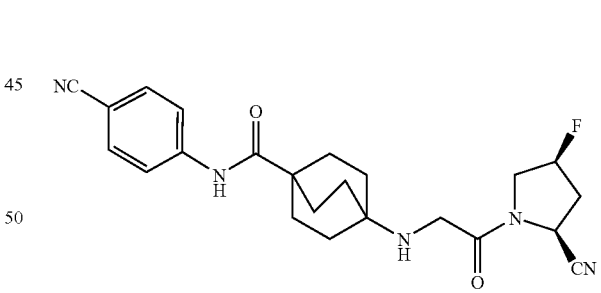

Synthesis of (2S,4S)-1-[[N-[4-[N-(4-cyanophenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminobenzonitrile (40.0 mg) were used to obtain (2S,4S)-1-[[N-[4-[N-(4-cyanophenyl)amino]carbonylbicyclo[2.2.2]oct-1-yl]amino]acetyl]-4-fluoropyrrolidine-2-carbonitrile (17.6 mg).

MS (FAB⁺) m/z: 424 (MH⁺). HRMS (FAB⁺) for $C_{23}H_{27}FN_5O_2$ (MH⁺): calcd, 424.2149; found, 424.2129.

EXAMPLE 81

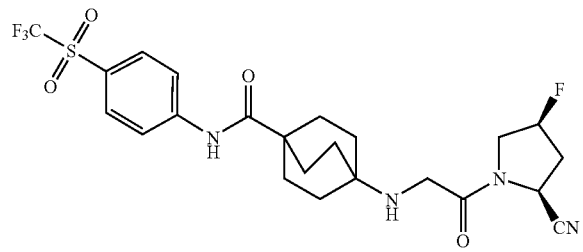

Synthesis of (2S,4S)-4-fluoro-1-[[N-[4-[N-(4-trifluoromethylsulfonylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-trifluoromethylsulfonylaniline (77.0 mg) were used to obtain (2S,4S)-4-fluoro-1-[[N-[4-[N-(4-trifluoromethylsulfonylphenyl)amino]carbonylbicyclo[2.2.2]oct-1-yl]amino]acetyl]pyrrolidine-2-carbonitrile (10.8 mg).

MS (FAB⁺) m/z: 531 (MH⁺). HRMS (FAB⁺) for $C_{23}H_{27}F_4N_4O_4S$ (MH⁺): calcd, 531.1689; found, 531.1682.

EXAMPLE 82

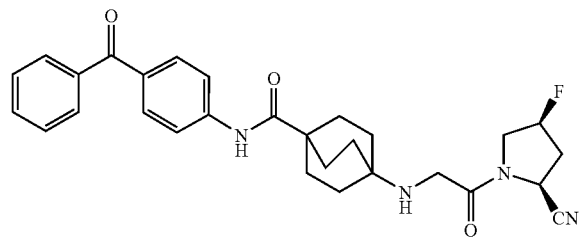

Synthesis of (2S,4S)-1-[[N-[4-[N-(4-benzoylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminobenzophenone (67.0 mg) were used to obtain (2S,4S)-1-[[N-[4-[N-(4-benzoylphenyl)amino]carbonylbicyclo[2.2.2]oct-1-yl]amino]acetyl]-4-fluoropyrrolidine-2-carbonitrile (11.5 mg).

MS (FAB⁺) m/z: 503 (MH⁺). HRMS (FAB⁺) for $C_{29}H_{32}FN_4O_3$ (MH⁺): calcd, 503.2458; found, 503.2439.

EXAMPLE 83

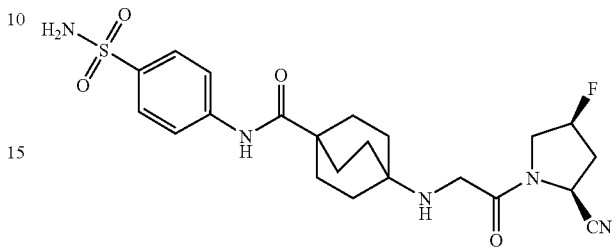

Synthesis of (2S,4S)-1-[[N-[4-[N-(4-aminosulfonylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and sulfanilamide (59.0 mg) were used to obtain (2S,4S)-1-[[N-[4-[N-(4-aminosulfonylphenyl)amino]carbonylbicyclo[2.2.2]oct-1-yl]amino]acetyl]-4-fluoropyrrolidine-2-carbonitrile (18.2 mg).

MS (FAB⁺) m/z: 478 (MH⁺). HRMS (FAB⁺) for $C_{22}H_{29}FN_5O_4S$ (MH⁺): calcd, 478.1924; found, 478.1940.

EXAMPLE 84

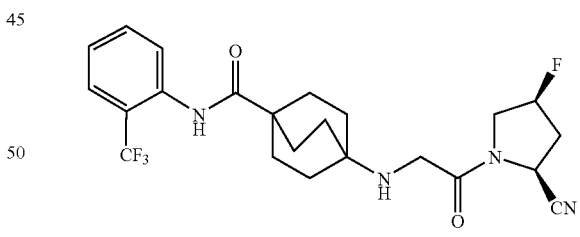

Synthesis of (2S,4S)-4-fluoro-1-[[N-[4-[N-(2-trifluoromethylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-aminobenzotrifluoride (55.0 mg) were used to obtain (2S,4S)-4-fluoro-1-[[N-[4-[N-(2-trifluoromethylphenyl)amino]carbonylbicyclo[2.2.2]oct-1-yl]amino]acetyl]pyrrolidine-2-carbonitrile (28.4 mg).

MS (FAB+) m/z: 467 (MH+). HRMS (FAB+) for $C_{23}H_{27}F_4N_4O_2$ (MH+): calcd, 467.2070; found, 467.2083.

EXAMPLE 85

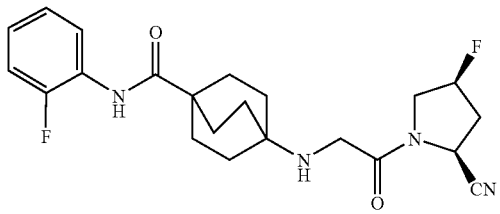

Synthesis of (2S,4S)-4-fluoro-1-[[N-[4-[N-(2-fluorophenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-fluoroaniline (38.0 mg) were used to obtain (2S,4S)-4-fluoro-1-[[N-[4-[N-(2-fluorophenyl)amino]carbonylbicyclo[2.2.2]oct-1-yl]amino]acetyl]pyrrolidine-2-carbonitrile (15.2 mg).

MS (FAB+) m/z: 417 (MH+). HRMS (FAB+) for $C_{22}H_{27}F_2N_4O_2$ (MH+): calcd, 417.2102; found, 417.2151.

EXAMPLE 86

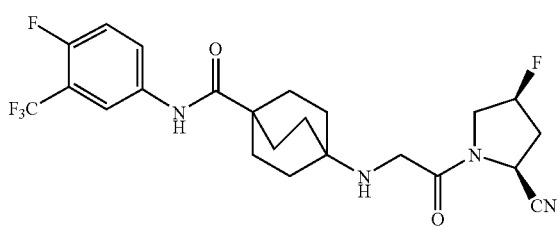

Synthesis of (2S,4S)-4-fluoro-1-[[N-[4-[N-(4-fluoro-3-trifluorophenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 5-amino-2-fluorobenzotrifluoride (41.0 mg) were used to obtain (2S,4S)-4-fluoro-1-[[N-[4-[N-(4-fluoro-3-trifluorophenyl)amino]carbonylbicyclo[2.2.2]oct-1-yl]amino]acetyl]pyrrolidine-2-carbonitrile (17.8 mg).

MS (FAB+) m/z: 485 (MH+). HRMS (FAB+) for $C_{23}H_{26}F_5N_4O_2$ (MH+): calcd, 485.1976; found, 485.1945.

EXAMPLE 87

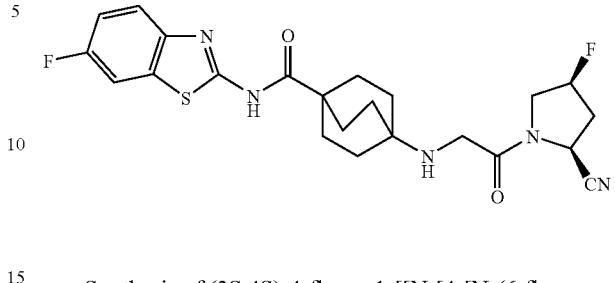

Synthesis of (2S,4S)-4-fluoro-1-[[N-[4-[N-(6-fluorobenzothiazol-2-yl)amino]carbonylbicyclo[2.2.2]oct-1-yl]amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (50.0 mg), benzotriazol-1-yl-oxytris(dimethylamino)phosphonium hexafluorophosphate (137 mg) and dichloromethane (1.5 mL) were mixed together. While the mixture was maintained at 0° C., triethylamine (43.1 μL) was added and the mixture was stirred at room temperature for 75 minutes. Subsequently, 2-amino-6-fluorobenzotriazole (57.2 mg) was added and the mixture was stirred at room temperature for one day. The resulting mixture washed sequentially with water and saturated aqueous sodium bicarbonate solution. The mixture was then dried over anhydrous sodium sulfate and concentrated under reduced pressure. The resulting residue was purified by a silica gel column (eluant:dichloromethane:methanol=10:1) to give (2S,4S)-4-fluoro-1-[[N-[4-[N-(6-fluorobenzothiazol-2-yl)amino]carbonylbicyclo[2.2.2]oct-1-yl]amino]acetyl]pyrrolidine-2-carbonitrile (49.7 mg) as a pale yellow solid.

MS (FAB+) m/z: 474 (MH+). HRMS (FAB+) for $C_{23}H_{26}F_2N_5O_2S$ (MH+): calcd, 474.1775; found, 474.1793.

EXAMPLE 88

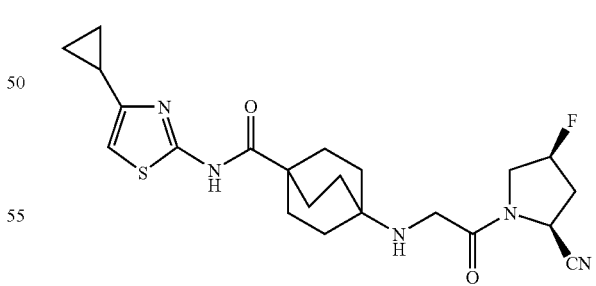

Synthesis of (2S,4S)-1-[[N-[4-[N-(4-cyclopropylthiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-4-cyclopropylthiazole (47.7 mg) were used to obtain (2S,4S)-1-[[N-[4-[N-(4-cyclopropylthiazol-2-yl)amino]carbonylbicyclo[2.2.2]oct-1-yl]amino]acetyl]-4-fluoropyrrolidine-2-carbonitrile (43.1 mg).

MS (FAB$^+$) m/z: 446 (MH$^+$). HRMS (FAB$^+$) for $C_{22}H_{29}FN_5O_2S$ (MH$^+$): calcd, 446.2026; found, 446.2017.

EXAMPLE 89

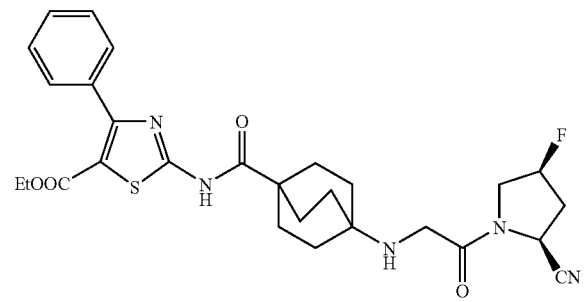

Synthesis of (2S,4S)-4-fluoro-1-[[N-[4-[N-(4-phenyl-5-ethoxycarbonylthiazol-2-yl)amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)]amino)acetyl]-4-fluoropyrrolidine-2-carbonitrile (50.0 mg) and ethyl 2-amino-5-phenylthiazole-6-carboxylate (84.5 mg) were used to obtain (2S,4S)-4-fluoro-1-[(N-[4-[N-(4-phenyl-5-ethoxycarbonylthiazol-2-yl)amino]carbonylbicyclo[2.2.2]oct-1-yl]amino]acetyl]pyrrolidine-2-carbonitrile (34.1 mg).

MS (FAB$^+$) m/z: 554 (MH$^+$). HRMS (FAB$^+$) for $C_{28}H_{33}FN_5O_4S$ (MH$^+$): calcd, 554.2237; found, 554.2235.

EXAMPLE 90

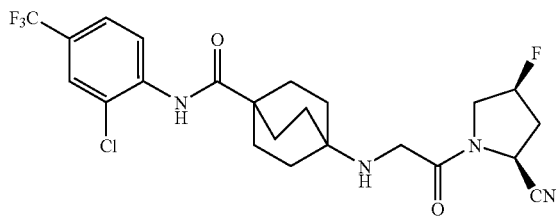

Synthesis of (2S,4S)-1-[[N-[4-[N-(2-chloro-4-trifluorophenyl)amino]carbonylbicyclo[2.2.2]oct-1-yl])amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (80.0 mg) and 4-amino-3-chlorobenzotrifluoride (111 mg) were used to obtain (2S,4S)-1-[[N-[4-[N-(2-chloro-4-trifluorophenyl)amino]carbonylbicyclo[2.2.2]oct-1-yl]]amino]acetyl]-4-fluoropyrrolidine-2-carbonitrile (15.3 mg).

MS (FAB$^+$) m/z: 501 (MH$^+$). HRMS (FAB$^+$) for $C_{23}H_{26}ClF_4N_4O_2$ (MH$^+$): calcd, 501.1680; found, 501.1713.

EXAMPLE 91

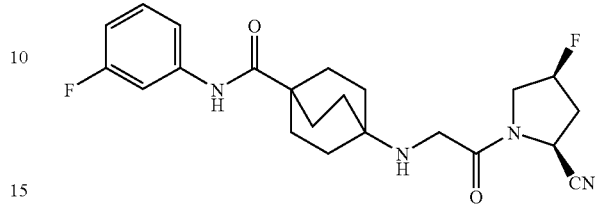

Synthesis of (2S,4S)-4-fluoro-1-[[N-[4-[N-(3-fluorophenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (80.0 mg) and 3-fluoroaniline (63.0 mg) were used to obtain (2S,4S)-4-fluoro-1-[[N-[4-[N-(3-fluorophenyl)amino]carbonylbicyclo[2.2.2]oct-1-yl]amino]acetyl]pyrrolidine-2-carbonitrile (38.1 mg).

MS (FAB$^+$) m/z: 417 (MH$^+$). HRMS (FAB$^+$) for $C_{22}H_{27}F_2N_4O_2$ (MH$^+$): calcd, 417.2102; found, 417.2144.

EXAMPLE 92

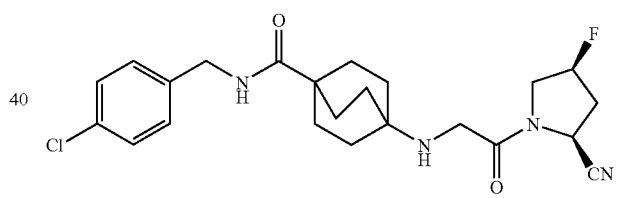

Synthesis of (2S,4S)-1-[[N-[4-[N-(4-chlorophenylmethyl)amino]carbonylbicyclo[2.2.2]oct-1-yl]amino]acetyl]-4-fluoropyrrolidine-2-carbonitrile (2S,4S)-1-[[N-(4-Carboxybicyclo[2.2.2]oct-1-yl)amino]acetyl]-4-fluoropyrrolidine-2-carbonitrile (50.0 mg), 1-hydroxybenzotriazole (28.0 mg), PS-carbodiimide (240 mg) and dichloromethane (4 mL) were mixed together and the mixture was stirred at room temperature for 15 minutes. 4-chlorobenzylamine (19.0 μL) was then added and the mixture was stirred at room temperature for further 24 hours. Subsequently, MP-carbonate (270 mg) was added and the mixture was stirred at room temperature for 5 hours and was left overnight. The insoluble material in the mixture was filtered and the filtrate was concentrated under reduced pressure. The resulting residue was then purified by a silica gel column (eluant:dichloromethane:methanol=10:1) to give (2S,4S)-1-[[N-[4-[N-(4-chlorophenylmethyl)amino]carbonylbicyclo[2.2.2]oct-1-yl]amino]acetyl]-4-fluoropyrrolidine-2-carbonitrile (29.1 mg).

EXAMPLE 93

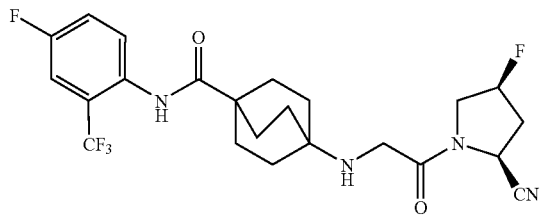

Synthesis of (2S,4S)-4-fluoro-1-[[N-[4-[N-(4-fluoro-2-trifluorophenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-amino-5-fluorobenzotrifluoride (64.0 mg) were used to obtain (2S,4S)-4-fluoro-1-[[N-[4-[N-(4-fluoro-2-trifluorophenyl)amino]carbonylbicyclo[2.2.2]oct-1-yl]amino]acetyl]pyrrolidine-2-carbonitrile (14.8 mg).

MS (FAB$^+$) m/z: 485 (MH$^+$). HRMS (FAB$^+$) for $C_{23}H_{26}F_5N_4O_2$ (MH$^+$): calcd, 485.1976; found, 485.2004.

EXAMPLE 94

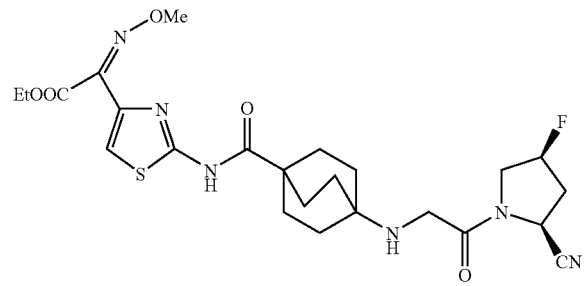

Synthesis of (2S,4S)-1-[[N-[4-[N-[(1-ethoxycarbonyl-1-methoxyiminomethyl)thiazol-2-yl]amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and ethyl 2-amino-α-methoxy-iminothiazole-4-acetate (78.0 mg) were used to obtain (2S,4S)-1-[[N-[4-[N-[(1-ethoxycarbonyl-1-methoxyiminomethyl)thiazol-2-yl]amino]carbonylbicyclo[2.2.2]oct-1-yl]amino]acetyl]-4-fluoropyrrolidine-2-carbonitrile (43.4 mg).

MS (FAB$^+$) m/z: 535 (MH$^+$). HRMS (FAB$^+$) for $C_{24}H_{32}FN_6O_5S$ (MH$^+$): calcd, 535.2139; found, 535.2119

EXAMPLE 95

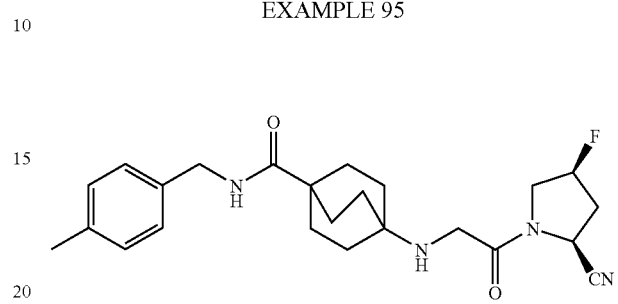

Synthesis of (2S,4S)-4-fluoro-1-[[N-[4-[N-(4-methylphenylmethyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-methylbenzylamine (41.0 mg) were used to obtain (2S,4S)-4-fluoro-1-[[N-[4-[N-(4-methylphenylmethyl)amino]carbonylbicyclo[2.2.2]oct-1-yl]amino]acetyl]pyrrolidine-2-carbonitrile (18.1 mg).

MS (FAB$^+$) m/z: 427 (MH$^+$). HRMS (FAB$^+$) for $C_{24}H_{32}FN_4O_2$ (MH$^+$): calcd, 427.2509; found, 427.2534.

EXAMPLE 96

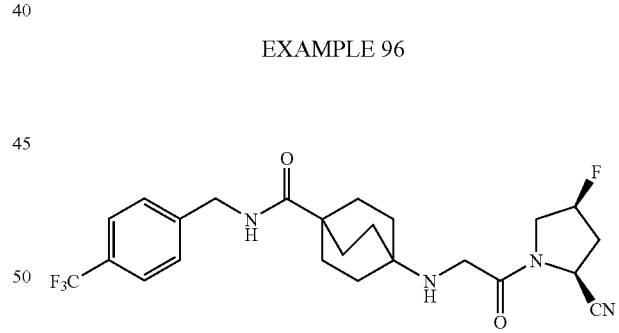

Synthesis of (2S,4S)-4-fluoro-1-[[N-(4-[N-(4-trifluoromethylphenylmethyl)amino]carbonylbicyclo[2.2.2]oct-1-yl)amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-(trifluoromethyl)benzylamine (60.0 mg) were used to obtain (2S,4S)-4-fluoro-1-[[N-(4-[N-(4-trifluoromethylphenylmethyl)amino]carbonylbicyclo[2.2.2]oct-1-yl)amino]acetyl]pyrrolidine-2-carbonitrile (22.0 mg).

MS (FAB⁺) m/z: 481 (MH⁺). HRMS (FAB⁺) for $C_{24}H_{29}F_4N_4O_2$ (MH⁺): calcd, 481.2227; found, 481.2228.

EXAMPLE 97

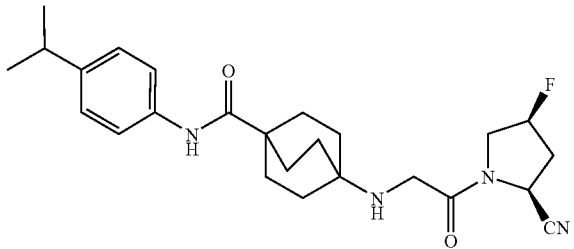

Synthesis of (2S,4S)-4-fluoro-1-[[N-[4-[N-[4-(1-methylethyl)phenyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-isopropylaniline (46.0 mg) were used to obtain (2S,4S)-4-fluoro-1-[[N-[4-[N-[4-(1-methylethyl)phenyl]amino]carbonylbicyclo[2.2.2]oct-1-yl]amino]acetyl]pyrrolidine-2-carbonitrile (36.3 mg).

MS (FAB⁺) m/z: 441 (MH⁺). HRMS (FAB⁺) for $C_{25}H_{34}FN_4O_2$ (MH⁺): calcd, 441.2666; found, 441.2687.

EXAMPLE 98

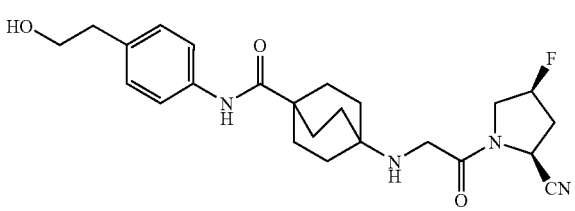

Synthesis of (2S,4S)-4-fluoro-1-[[N-[4-[N-[4-(2-hydroxyethyl)phenyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-(4-aminophenyl)ethanol (47.0 mg) were used to obtain (2S,4S)-4-fluoro-1-[[N-[4-[N-[4-(2-hydroxyethyl)phenyl]amino]carbonylbicyclo[2.2.2]oct-1-yl]amino]acetyl]pyrrolidine-2-carbonitrile (35.6 mg).

MS (FAB⁺) m/z: 443 (MH⁺). HRMS (FAB⁺) for $C_{25}H_{32}FN_4O_3$ (MH⁺): calcd, 443.2548; found, 443.2452.

EXAMPLE 99

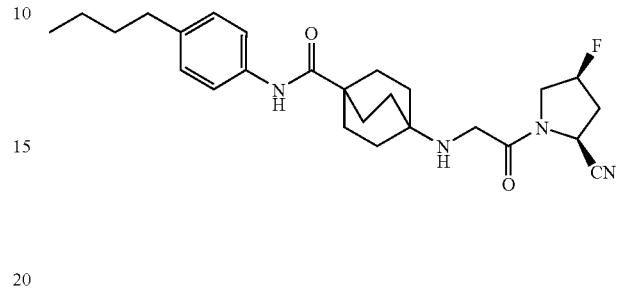

Synthesis of (2S,4S)-1-[[N-[4-[N-(4-butylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-butylaniline (51.0 mg) were used to obtain (2S,4S)-1-[[N-[4-[N-(4-butylphenyl)amino]carbonylbicyclo[2.2.2]oct-1-yl]amino]acetyl]-4-fluoropyrrolidine-2-carbonitrile (28.2 mg).

MS (FAB⁺) m/z: 455 (MH⁺). HRMS (FAB⁺) for $C_{26}H_{36}FN_4O_2$ (MH⁺): calcd, 455.2822; found, 455.2859.

EXAMPLE 100

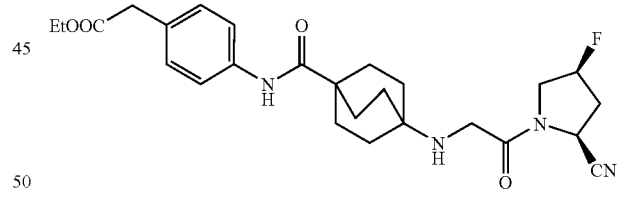

Synthesis of (2S,4S)-1-[[N-[4-[N-(4-ethoxycarbonylmethylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and ethyl 4-aminophenylacetate (61.0 mg) were used to obtain (2S,4S)-1-[[N-[4-[N-(4-ethoxycarbonylmethylphenyl)amino]carbonylbicyclo[2.2.2]oct-1-yl]amino]acetyl]-4-fluoropyrrolidine-2-carbonitrile (33.6 mg).

MS (FAB+) m/z: 485 (MH+). HRMS (FAB+) for $C_{26}H_{34}FN_4O_4$ (MH+): calcd, 485.2564; found, 485.2576.

EXAMPLE 101

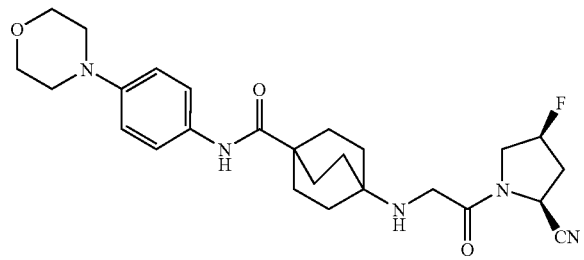

Synthesis of (2S,4S)-4-fluoro-1-[[N-[4-[N-(4-morpholinylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-morpholinylaniline (61.0 mg) were used to obtain (2S,4S)-4-fluoro-1-[[N-[4-[N-(4-morpholinylphenyl)amino]carbonylbicyclo[2.2.2]oct-1-yl]amino]acetyl]pyrrolidine-2-carbonitrile (33.0 mg).

MS (FAB+) m/z: 484 (MH+). HRMS (FAB+) for $C_{26}H_{35}FN_5O_3$ (MH+): calcd, 484.2724; found, 484.2726.

EXAMPLE 102

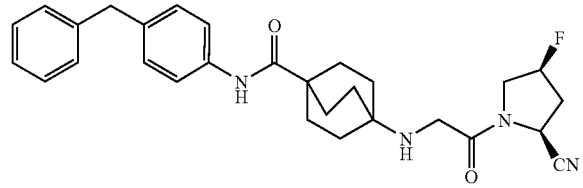

Synthesis of (2S,4S)-4-fluoro-1-[[N-[4-[N-(4-phenylmethylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminodiphenylmethane (62.0 mg) were used to obtain (2S,4S)-4-fluoro-1-[[N-[4-[N-(4-phenylmethylphenyl)amino]carbonylbicyclo[2.2.2]oct-1-yl]amino]acetyl]pyrrolidine-2-carbonitrile (31.1 mg).

MS (FAB+) m/z: 489 (MH+). HRMS (FAB+) for $C_{29}H_{34}FN_4O_2$ (MH+) calcd, 489.2666; found, 489.2638.

EXAMPLE 103

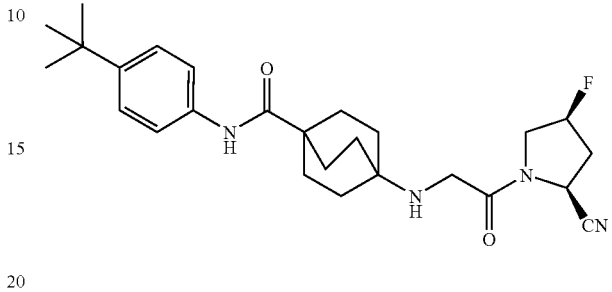

Synthesis of (2S,4S)-4-fluoro-1-[[N-[4-[N-[4-(1,1-dimethylethyl)phenyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-tert-butylaniline (51.0 mg) were used to obtain (2S,4S)-4-fluoro-1-[[N-[4-[N-[4-(1,1-dimethylethyl)phenyl]amino]carbonylbicyclo[2.2.2]oct-1-yl]amino]acetyl]pyrrolidine-2-carbonitrile (21.1 mg).

MS (FAB+) m/z: 455 (MH+). HRMS (FAB+) for $C_{26}H_{36}FN_4O_2$ (MH+): calcd, 455.2822; found, 455.2821.

EXAMPLE 104

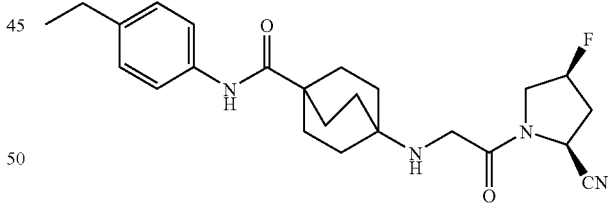

Synthesis of (2S,4S)-1-[[N-[4-[N-(4-ethylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-ethylaniline (40.0 mg) were used to obtain (2S,4S)-1-[[N-[4-[N-(4-ethylphenyl)amino]carbonylbicyclo[2.2.2]oct-1-yl]amino]acetyl]-4-fluoropyrrolidine-2-carbonitrile (24.7 mg).

MS (FAB+) m/z: 427 (MH+). HRMS (FAB+) for C$_{24}$H$_{32}$FN$_4$O$_2$ (MH+): calcd, 427.2509; found, 427.2469.

EXAMPLE 105

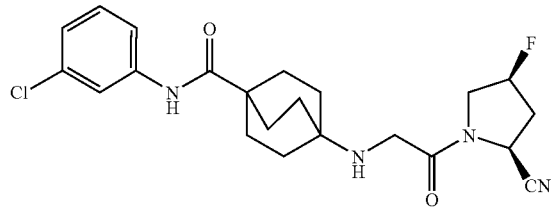

Synthesis of (2S,4S)-1-[[N-[4-[N-(3-chlorophenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 3-chloroaniline (36.0 μL) were used to obtain (2S,4S)-1-[[N-[4-[N-(3-chlorophenyl)amino]carbonylbicyclo[2.2.2]oct-1-yl]amino]acetyl]-4-fluoropyrrolidine-2-carbonitrile (23.3 mg).

MS (FAB+) m/z: 433 (MH+). HRMS (FAB+) for C$_{22}$H$_{27}$ClFN$_4$O$_2$ (MH+): calcd, 433.1807; found, 433.1778.

EXAMPLE 106

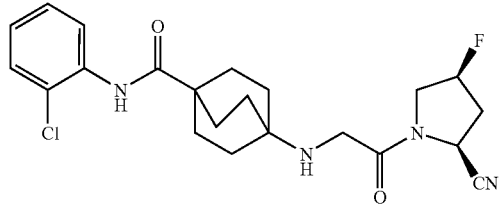

Synthesis of (2S,4S)-1-[[N-[4-[N-(2-chlorophenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-chloroaniline (35.8 μL) were used to obtain (2S,4S)-1-[[N-[4-[N-(2-chlorophenyl)amino]carbonylbicyclo[2.2.2]oct-1-yl]amino]acetyl]-4-fluoropyrrolidine-2-carbonitrile (17.4 mg).

MS (FAB+) m/z: 433 (MH+). HRMS (FAB+) for C$_{22}$H$_{27}$ClFN$_4$O$_2$ (MH+): calcd, 433.1807; found, 433.1846.

EXAMPLE 107

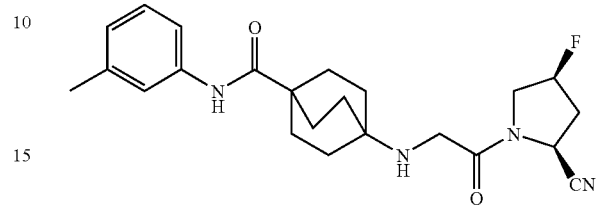

Synthesis of (2S,4S)-4-fluoro-1-[[N-[4-[N-(3-methylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and m-toluidine (25.8 μL) were used to obtain (2S,4S)-4-fluoro-1-[[N-[4-[N-(3-methylphenyl)amino]carbonylbicyclo[2.2.2]oct-1-yl]amino]acetyl]pyrrolidine-2-carbonitrile (18.3 mg).

MS (FAB+) m/z: 413 (MH+). HRMS (FAB+) for C$_{23}$H$_{30}$FN$_4$O$_2$ (MH+): calcd, 413.2353; found, 413.2367.

EXAMPLE 108

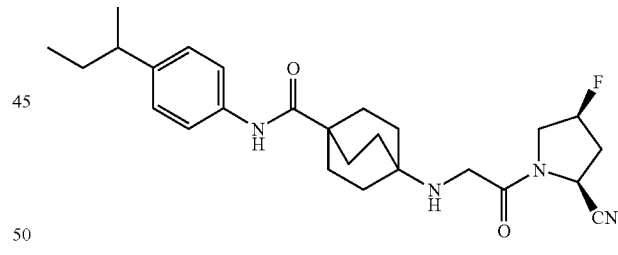

Synthesis of (2S,4S)-4-fluoro-1-[[N-[4-[N-[4-(1-methylpropyl)phenyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-sec-butylaniline (51.5 mg) were used to obtain (2S,4S)-4-fluoro-1-[[N-[4-[N-[4-(1-methylpropyl)phenyl]amino]carbonylbicyclo[2.2.2]oct-1-yl]amino]acetyl)pyrrolidine-2-carbonitrile (13.0 mg).

MS (FAB+) m/z: 455 (MH+). HRMS (FAB+) for C$_{26}$H$_{36}$FN$_4$O$_2$ (MH+): calcd, 455.2822; found, 455.2829.

EXAMPLE 109

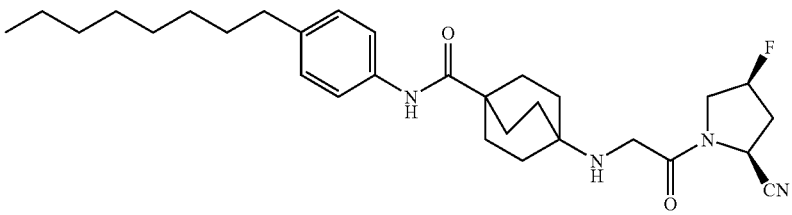

Synthesis of (2S,4S)-4-fluoro-1-[[N-[4-[N-(4-octylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-octylaniline (70.5 mg) were used to obtain (2S,4S)-4-fluoro-1-[[N-[4-[N-(4-octylphenyl)amino]carbonylbicyclo[2.2.2]oct-1-yl]amino]acetyl]pyrrolidine-2-carbonitrile (15.8 mg).

MS (FAB$^+$) m/z: 511 (MH$^+$). HRMS (FAB$^+$) for $C_{30}H_{44}FN_4O_2$ (MH$^+$): calcd, 511.3448; found, 511.3455.

EXAMPLE 110

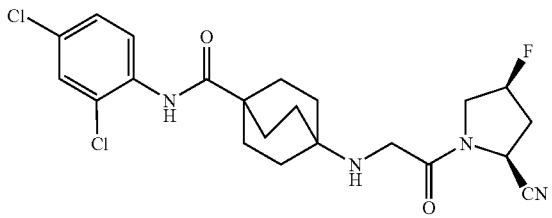

Synthesis of (2S,4S)-1-[[N-[4-[N-(2,4-dichlorophenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2,4-dichloroaniline (55.1 mg) were used to obtain (2S,4S)-1-[[N-[4-[N-(2,4-dichlorophenyl)amino]carbonylbicyclo[2.2.2]oct-1-yl]amino]acetyl]-4-fluoropyrrolidine-2-carbonitrile (25.5 mg).

MS (FAB$^+$) m/z: 467 (MH$^+$). HRMS (FAB$^+$) for $C_{22}H_{26}Cl_2FN_4O_2$ (MH$^+$): calcd, 467.1417; found, 467.1441.

EXAMPLE 111

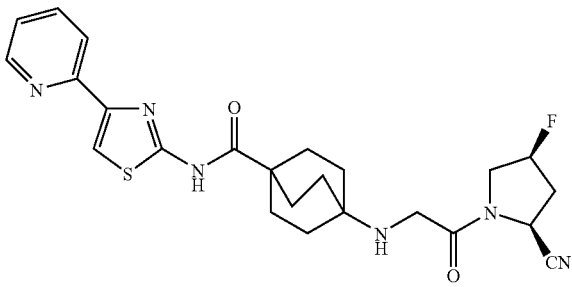

Synthesis of (2S,4S)-4-fluoro-1-[[N-[4-[N-[4-(2-pyridyl)thiazol-2-yl]amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-4-(2-pyridyl)thiazole (60.3 mg) were used to obtain (2S,4S)-4-fluoro-1-[[N-[4-[N-[4-(2-pyridyl)thiazol-2-yl]amino]carbonylbicyclo[2.2.2]oct-1-yl]amino]acetyl)pyrrolidine-2-carbonitrile (11.6 mg).

MS (FAB$^+$) m/z: 483 (MH$^+$). HRMS (FAB$^+$) for $C_{24}H_{28}FN_6O_2S$ (MH$^+$): calcd, 483.1978; found, 483.1966.

EXAMPLE 112

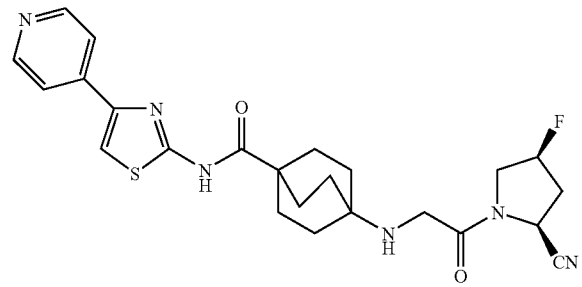

Synthesis of (2S,4S)-4-fluoro-1-[[N-[4-[N-[4-(4-pyridyl)thiazol-2-yl]amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-4-(4-pyridyl)thiazole (60.3 mg) were used to obtain (2S,4S)-4-fluoro-1-[[N-[4-[N-[4-(4-pyridyl)thiazol-2-yl]amino]carbonylbicyclo[2.2.2]oct-1-yl]amino]acetyl]pyrrolidine-2-carbonitrile (15.2 mg).

MS (FAB$^+$) m/z: 483 (MH$^+$). HRMS (FAB$^+$) for $C_{24}H_{28}FN_6O_2S$ (MH$^+$): calcd, 483.1978; found, 483.2014.

EXAMPLE 113

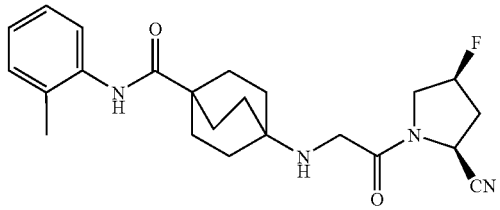

Synthesis of (2S,4S)-4-fluoro-1-[[N-[4-[N-(2-methylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and o-toluidine (36.3 μL) were used to obtain (2S,4S)-4-fluoro-1-[[N-[4-[N-(3-methylphenyl)amino]carbonylbicyclo[2.2.2]oct-1-yl]amino]acetyl]pyrrolidine-2-carbonitrile (22.6 mg).

MS (FAB$^+$) m/z: 413 (MH$^+$). HRMS (FAB$^+$) for $C_{23}H_{30}FN_4O_2$ (MH$^+$): calcd, 413.2353; found, 413.2384.

EXAMPLE 114

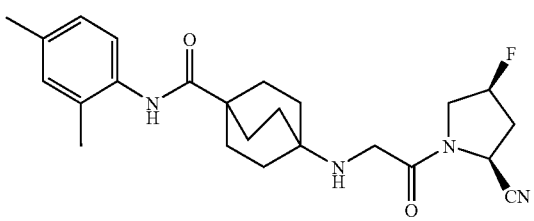

Synthesis of (2S,4S)-4-fluoro-1-[[N-[4-[N-(2,4-dimethylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2,4-dimethylaniline (42.3 μL) were used to obtain (2S,4S)-4-fluoro-1-[[N-[4-[N-(2,4-dimethylphenyl)amino]carbonylbicyclo[2.2.2]oct-1-yl]amino]acetyl]pyrrolidine-2-carbonitrile (22.4 mg).

MS (FAB$^+$) m/z: 427 (MH$^+$). HRMS (FAB$^+$) for $C_{24}H_{32}FN_4O_2$ (MH$^+$): calcd, 427.2509; found, 427.2490.

EXAMPLE 115

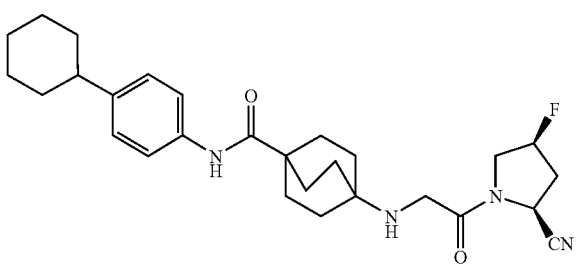

Synthesis of (2S,4S)-1-[[N-[4-[N-(4-cyclohexylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-cyclohexylaniline (60.0 mg) were used to obtain (2S,4S)-1-[[N-[4-[N-(4-cyclohexylphenyl)amino]carbonylbicyclo[2.2.2]oct-1-yl]amino]acetyl]-4-fluoropyrrolidine-2-carbonitrile (22.3 mg).

MS (FAB$^+$) m/z: 481 (MH$^+$). HRMS (FAB$^+$) for $C_{28}H_{38}FN_4O_2$ (MH$^+$): calcd, 481.2979; found, 481.2932.

EXAMPLE 116

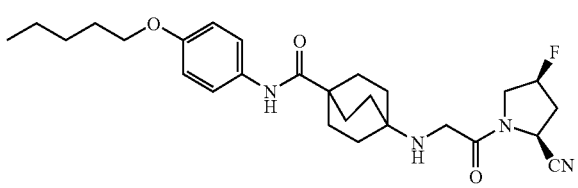

Synthesis of (2S,4S)-4-fluoro-1-[[N-[4-[N-(4-pentyloxyphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-pentyloxyaniline (61.0 mg) were used to obtain (2S,4S)-4-fluoro-1-[[N-[4-[N-(4-pentyloxyphenyl)amino]carbonylbicyclo[2.2.2]oct-1-yl]amino]acetyl]pyrrolidine-2-carbonitrile (37.6 mg).

MS (FAB$^+$) m/z: 485 (MH$^+$). HRMS (FAB$^+$) for $C_{27}H_{38}FN_4O_3$ (MH$^+$): calcd, 485.2928; found, 485.2905.

EXAMPLE 117

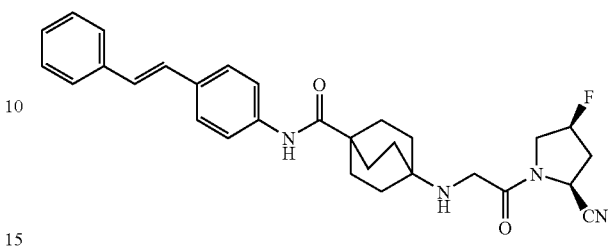

Synthesis of (2S,4S)-4-fluoro-1-[[N-[4-[N-(4-styrylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminostilbene (66.4 mg) were used to obtain (2S,4S)-4-fluoro-1-[[N-[4-[N-(4-styrylphenyl)amino]carbonylbicyclo[2.2.2]oct-1-yl]amino]acetyl]pyrrolidine-2-carbonitrile (21.3 mg).

MS (FAB$^+$) m/z: 501 (MH$^+$). HRMS (FAB$^+$) for $C_{30}H_{34}FN_4O_2$ (MH$^+$): calcd, 501.2666; found, 501.2637.

EXAMPLE 118

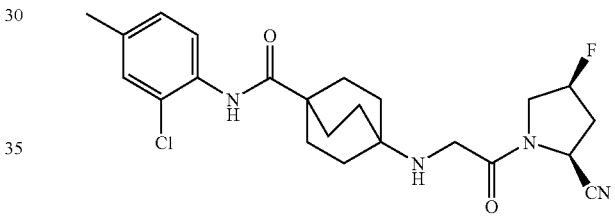

Synthesis of (2S,4S)-1-[[N-[4-[N-(2-chloro-4-methylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-chloro-4-methylaniline (41.8 μL) were used to obtain (2S,4S)-1-[[N-[4-[N-(2-chloro-4-methylphenyl)amino]carbonylbicyclo[2.2.2]oct-1-yl]amino]acetyl]-4-fluoropyrrolidine-2-carbonitrile (22.6 mg).

MS (FAB$^+$) m/z: 447 (MH$^+$). HRMS (FAB$^+$) for $C_{23}H_{29}ClFN_4O_2$ (MH$^+$): calcd, 447.1963; found, 447.2000.

EXAMPLE 119

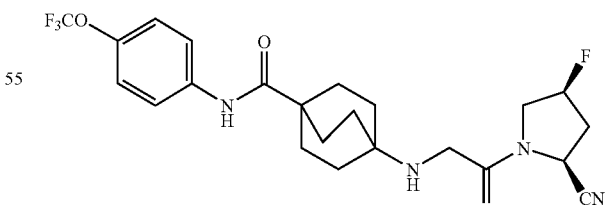

Synthesis of (2S,4S)-4-fluoro-1-[[N-[4-[N-(4-trifluoromethoxyphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.3 mg) and 4-trifluoromethoxyaniline (60.0 mg) were used to obtain (2S,4S)-4-fluoro-1-[[N-[4-[N-(4-trifluoromethoxyphenyl)amino]carbonylbicyclo[2.2.2]oct-1-yl]amino]acetyl]pyrrolidine-2-carbonitrile (28.2 mg).

MS (FAB$^+$) m/z: 483 (MH$^+$). HRMS (FAB$^+$) for $C_{23}H_{27}F_4N_4O_3$ (MH$^+$): calcd, 483.2019; found, 483.1989.

EXAMPLE 120

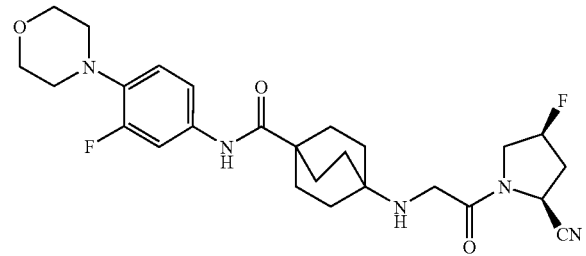

Synthesis of (2S,4S)-4-fluoro-1-[[N-[4-[N-(3-fluoro-4-morpholinylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.3 mg) and 3-fluoro-4-morpholinylaniline (62.0 mg) were used to obtain (2S,4S)-4-fluoro-1-[[N-[4-[N-(3-fluoro-4-morpholinylphenyl)amino]carbonylbicyclo[2.2.2]oct-1-yl]amino]acetyl]pyrrolidine-2-carbonitrile (28.6 mg).

MS (FAB$^+$) m/z: 502 (MH$^+$). HRMS (FAB$^+$) for $C_{26}H_{34}F_2N_5O_3$ (MH$^+$): calcd, 502.2630; found, 502.2647.

EXAMPLE 121

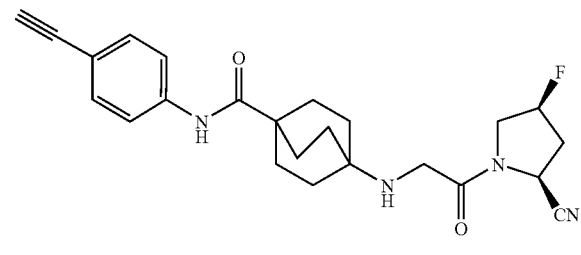

Synthesis of (2S,4S)-1-[[N-[4-[N-(4-ethynylphenyl)amino]carbonylbicyclo[2.2.2]oct-1-yl]amino]acetyl]-4-fluoropyrrolidine-2-carbonitrile In a similar manner to Example 63, ((2S,4S)-1-[[N-(4-carboxybicyclo[2.2.2]oct-1-yl)amino]acetyl]-4-fluoropyrrolidine-2-carbonitrile (50.0 mg) and 4-ethynylaniline (40.0 mg) were used to obtain (2S,4S)-1-[[N-[4-[N-(4-ethynylphenyl)amino]carbonylbicyclo[2.2.2]oct-1-yl]amino]acetyl]-4-fluoropyrrolidine-2-carbonitrile (10.0 mg).

MS (FAB$^+$) m/z: 423 (MH$^+$). HRMS (FAB$^+$) for $C_{24}H_{28}FN_4O_2$ (MH$^+$): calcd, 423.2196; found, 423.2204.

EXAMPLE 122

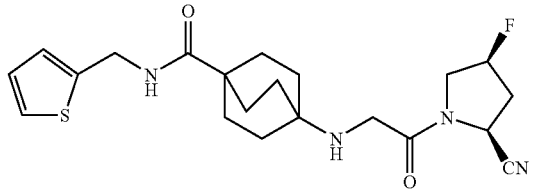

Synthesis of (2S,4S)-4-fluoro-1-[[N-[4-[N-(2-thienylmethyl)amino]carbonylbicyclo[2.2.2]oct-1-yl]amino]acetyl]pyrrolidine-2-carbonitrile In a similar manner to Example 92, (2S,4S)-1-[[N-(4-carboxybicyclo[2.2.2]oct-1-yl)amino]acetyl]-4-fluoropyrrolidine-2-carbonitrile (50.0 mg) and 2-thienylmethylamine (38.5 mg) were used to obtain (2S,4S)-4-fluoro-1-[[N-[4-[N-(2-thienylmethyl)amino]carbonylbicyclo[2.2.2]oct-1-yl]amino]acetyl]pyrrolidine-2-carbonitrile (48.8 mg).

MS (FAB$^+$) m/z: 419 (MH$^+$). HRMS (FAB$^+$) for $C_{21}H_{28}FN_4O_2S$ (MH$^+$): calcd, 419.1917; found, 419.1937.

EXAMPLE 123

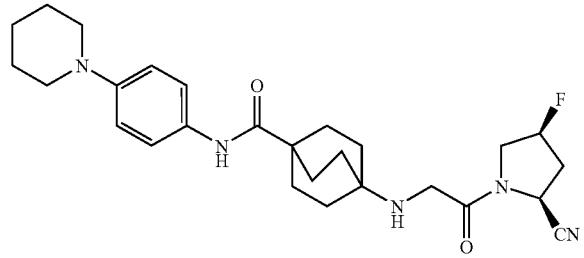

Synthesis of (2S,4S)-4-fluoro-1-[[N-[4-[N-(4-piperidinylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and N-(4-aminophenyl)piperidine (61.4 mg) were used to obtain (2S,4S)-4-fluoro-1-[[N-[4-[N-(4-piperidinylphenyl)amino]carbonylbicyclo[2.2.2]oct-1-yl]amino]acetyl]pyrrolidine-2-carbonitrile (14.6 mg).

MS (FAB$^+$) m/z: 482 (MH$^+$). HRMS (FAB$^+$) for $C_{27}H_{37}FN_5O_2$ (MH$^+$): calcd, 482.2931; found, 482.2913.

EXAMPLE 124

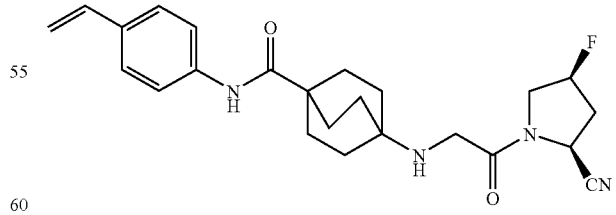

Synthesis of (2S,4S)-4-fluoro-1-[[N-[4-[N-(4-vinylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-aminostyrene (46.0 mg) were used to obtain (2S,4S)-4-fluoro-1-[[N-[4-[N-(4-vinylphenyl)amino]carbonylbicyclo[2.2.2]oct-1-yl]amino]acetyl]pyrrolidine-2-carbonitrile (13.1 mg).

MS (FAB⁺) m/z: 425 (MH⁺). HRMS (FAB⁺) for $C_{24}H_{30}FN_4O_2$ (MH⁺): calcd, 425.2353; found, 425.2314.

EXAMPLE 125

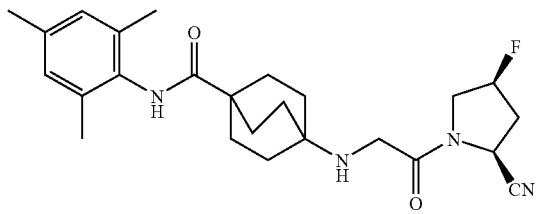

Synthesis of (2S,4S)-4-fluoro-1-[[N-[4-[N-(2,4,6-trimethylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (75.0 mg) and 2,4,6-trimethylaniline (71.6 µL) were used to obtain (2S,4S)-4-fluoro-1-[[N-[4-[N-(2,4,6-trimethylphenyl)amino]carbonylbicyclo[2.2.2]oct-1-yl]amino]acetyl]pyrrolidine-2-carbonitrile (29.1 mg).

MS (FAB⁺) m/z: 441 (MH⁺). HRMS (FAB⁺) for $C_{25}H_{34}FN_4O_2$ (MH⁺): calcd, 441.2666; found, 441.2659.

EXAMPLE 126

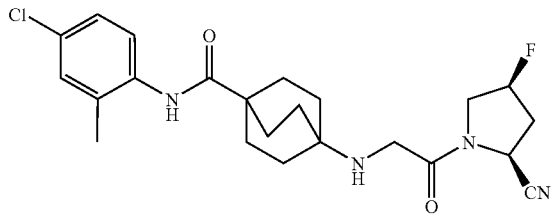

Synthesis of (2S,4S)-1-[[N-[4-[N-(4-chloro-2-methylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 2-amino-5-chlorotoluene (48.2 mg) were used to obtain (2S,4S)-1-[[N-[4-[N-(4-chloro-2-methylphenyl)amino]carbonylbicyclo[2.2.2]oct-1-yl]amino]acetyl]-4-fluoropyrrolidine-2-carbonitrile (16.8 mg).

MS (FAB⁺) m/z: 447 (MH⁺). HRMS (FAB⁺) for $C_{23}H_{29}ClFN_4O_2$ (MH⁺): calcd, 447.1963; found, 447.1973.

EXAMPLE 127

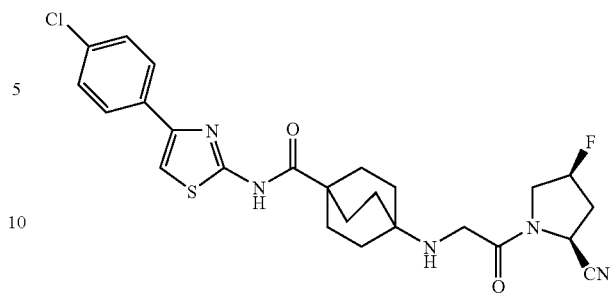

Synthesis of (2S,4S)-1-[[N-[4-[N-[4-(4-chlorophenyl)thiazol-2-yl]amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-4-(4-chlorophenyl)thiazole (71.7 mg) were used to obtain (2S,4S)-1-[[N-[4-[N-4-(4-chlorophenyl)thiazol-2-yl]amino]carbonylbicyclo[2.2.2]oct-1-yl]amino]acetyl]-4-fluoropyrrolidine-2-carbonitrile (23.3 mg).

MS (FAB⁺) m/z: 516 (MH⁺). HRMS (FAB⁺) for $C_{25}H_{28}ClFN_5O_2S$ (MH⁺): calcd, 516.1636; found, 516.1620.

EXAMPLE 128

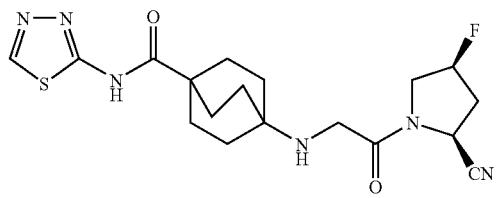

Synthesis of (2S,4S)-1-[[N-[4-[N-(1,3,4-thiadiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-1,3,4-thiadiazole (34.4 mg) were used to obtain (2S,4S)-1-[[N-[4-[N-(1,3,4-thiadiazol-2-yl)amino]carbonylbicyclo[2.2.2]oct-1-yl]amino]acetyl]-4-fluoropyrrolidine-2-carbonitrile (20.9 mg).

MS (FAB⁺) m/z: 407 (MH⁺). HRMS (FAB⁺) for $C_{18}H_{24}FN_6O_2S$ (MH⁺): calcd, 407.1665; found, 407.1620.

EXAMPLE 129

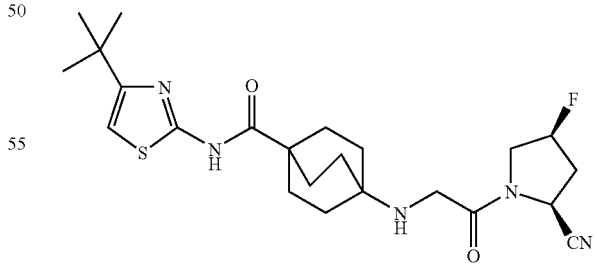

Synthesis of (2S,4S)-4-fluoro-1-[[N-[4-[N-[4-(2,2-dimethylethyl)thiazol-2-yl]amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-4-tert-butylthiazole (53.1 mg) were used to obtain (2S,4S)-4-fluoro-1-[[N-[4-[N-[4-(2,2-dimethylethyl)thiazol-2-yl]amino]carbonylbicyclo[2.2.2]oct-1-yl]amino]acetyl]pyrrolidine-2-carbonitrile (35.9 mg).

MS (FAB$^+$) m/z: 462 (MH$^+$). HRMS (FAB$^+$) for $C_{23}H_{33}FN_5O_2S$ (MH$^+$): calcd, 462.2339; found, 462.2286.

EXAMPLE 130

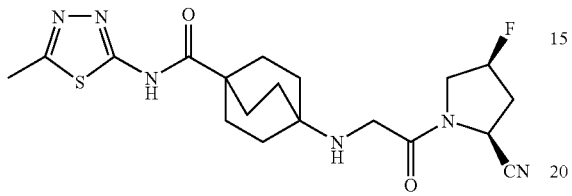

Synthesis of (2S,4S)-4-fluoro-1-[[N-[4-[N-(5-methyl-1,3,4-thiadiazol-2-yl)amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-5-methyl-1,3,4-thiadiazole (39.2 mg) were used to obtain (2S,4S)-4-fluoro-1-[[N-[4-[N-(5-methyl-1,3,4-thiadiazol-2-yl)amino]carbonylbicyclo[2.2.2]oct-1-yl]amino]acetyl]pyrrolidine-2-carbonitrile (40.4 mg).

MS (FAB$^+$) m/z: 421 (MH$^+$). HRMS (FAB$^+$) for $C_{19}H_{26}FN_6O_2S$ (MH$^+$): calcd, 421.1822; found, 421.1862.

EXAMPLE 131

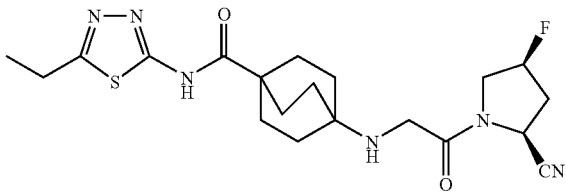

Synthesis of (2S,4S)-1-[[N-[4-[N-(5-ethyl-1,3,4-thiadiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-5-ethyl-1,3,4-thiadiazole (43.9 mg) were used to obtain (2S,4S)-1-[[N-[4-[N-(5-ethyl-1,3,4-thiadiazol-2-yl)amino]carbonylbicyclo[2.2.2]oct-1-yl]amino]acetyl]-4-fluoropyrrolidine-2-carbonitrile (34.8 mg).

MS (FAB$^+$) m/z: 435 (MH$^+$). HRMS (FAB$^+$) for $C_{20}H_{28}FN_6O_2S$ (MH$^+$): calcd, 435.1978; found, 435.1990.

EXAMPLE 132

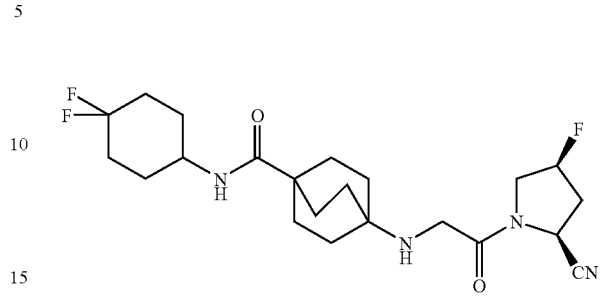

Synthesis of (2S,4S)-4-fluoro-1-[[N-[4-[N-(4,4-difluorocyclohexyl)amino]carbonylbicyclo[2.2.2]oct-1-yl]amino]acetyl]pyrrolidine-2-carbonitrile Step 1:

Synthesis of 4-benzyloxycarbonylamino-N-(4,4-difluorocyclohexyl)bicyclo[2.2.2]octane-1-carboxamide 1-Hydroxybenzotriazole (138 mg), 4-benzyloxycarbonylbicyclo[2.2.2]octane-1-carboxylic acid (72.0 mg) and N,N-dimethylformamide (8 mL) were mixed together. While the mixture was chilled in an ice bath, 1-(3-dimethylaminopropyl)-3-ethylcarbodiimide hydrochloride (265 mg) was added and the mixture was stirred at room temperature for 1 hour. Subsequently, a mixture of 4,4-difluorocyclohexylamine hydrochloride (108 mg), triethylamine (105 μL) and N,N-dimethylformamide (2 mL) was added and the resultant mixture was stirred at room temperature for 18 hours and was then concentrated under reduced pressure. Water (10 mL) was added to the residue and the solution was extracted with ethyl acetate (3×10 mL). The ethyl acetate extracts were combined, washed with saturated brine, dried over anhydrous sodium sulfate and concentrated under reduced pressure. The resulting residue was purified by a silica gel column (eluant:hexane:ethyl acetate=3:1) to give 4-benzyloxycarbonylamino-N-(4,4-difluorocyclohexyl)bicyclo[2.2.2]octane-1-carboxamide (57.0 mg) as a white solid.

MS (EI) m/z: 420 (M$^+$).

Step 2:

Synthesis of 4-amino-N-(4,4-difluorocyclohexyl)bicyclo[2.2.2]octane-1-carboxamide 4-Benzyloxycarbonylamino-N-(4,4-difluorocyclohexyl)bicyclo[2.2.2]octane-1-carboxamide (55.4 mg) was dissolved in tetrahydrofuran (6 mL). To this solution, 10% palladium carbon (20.0 mg) was added and the mixture was stirred at room temperature for 6 hours in a hydrogen atmosphere. The reaction mixture was filtered to remove the catalyst and the filtrate was concentrated under reduced pressure. The resulting residue was purified by a silica gel column (eluant:ethyl acetate:methanol=10:1) to give 4-amino-N-(4,4-difluorocyclohexyl)bicyclo[2.2.2]octane-1-carboxamide (38.1 mg) as a white solid.

MS (EI) m/z: 286 (M$^+$).

Step 3:

Synthesis of (2S,4S)-4-fluoro-1-[[N-[4-[N-(4,4-difluorocyclohexyl)amino]carbonylbicyclo[2.2.2]oct-1-yl]amino]acetyl]pyrrolidine-2-carbonitrile 4-Amino-N-(4,4-difluorocyclohexyl)bicyclo[2.2.2]octane-1-carboxamide (31.8 mg), potassium carbonate (16.4 mg) and N,N-dimethylformamide (1.5 mL) were mixed together. To the mixture, (2S,4S)-1-bromoacetyl-4-fluoropyrrolidine-2-carbonitrile (26.3 mg) in N,N-dimethylformamide (1 mL) was added dropwise at room temperature and the mixture was stirred for 90 minutes. Subsequently, the mixture was concentrated under reduced pressure and the resulting residue was purified by a silica gel column (eluant:dichloromethane:methanol=10:1) to give (2S,4S)-4-fluoro-1-[[N-(4-[N-(4,4-difluorocyclohexyl)amino]carbonylbicyclo[2.2.2]oct-1-yl]amino]acetyl]pyrrolidine-2-carbonitrile (12.0 mg).

MS (FAB$^+$) m/z: 441 (MH$^+$). HRMS (FAB$^+$) for $C_{22}H_{32}F_3N_4O_2$ (MH$^+$): calcd, 441.2477; found, 441.2475.

EXAMPLE 133

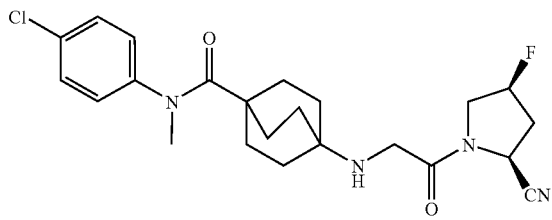

Synthesis of (2S,4S)-1-[[N-[4-[N-(4-chlorophenyl)-N-methylamino]carbonylbicyclo[2.2.2]oct-1-yl]amino]acetyl]-4-fluoropyrrolidine-2-carbonitrile Step 1:

Synthesis of 4-tert-butoxycarbonylamino-N-(4-chlorophenyl)-N-methylbicyclo[2.2.2]octane-1-carboxamide 4-tert-Butoxycarbonylaminobicyclo[2.2.2]octane-1-carboxylic acid (101 mg) was dissolved in dichloromethane (2 mL). To this solution, trichloroacetonitrile (74.0 µL) and triphenylphosphine (196 mg) in dichloromethane (1.5 mL) were sequentially added and the mixture was stirred at room temperature for 2 hours. This was followed by addition of triethylamine (0.18 mL) and 4-chloro-N-methylaniline (98.6 µL) and stirring at room temperature for additional 5.5 hours. The reaction mixture was then poured into aqueous citric acid (5 mL) and was extracted with ethyl acetate (3×10 mL). The ethyl acetate extracts were combined, washed with saturated aqueous sodium bicarbonate solution, dried over anhydrous sodium sulfate and concentrated under reduced pressure. The resulting residue was purified by a silica gel column (eluant: hexane:ethyl acetate=2:1) to give 4-tert-butoxycarbonylamino-N-(4-chlorophenyl)-N-methylbicyclo[2.2.2]octane-1-carboxamide (91.4 mg) as a white powder.

Step 2:

Synthesis of 4-amino-N-(4-chlorophenyl)-N-methylbicyclo[2.2.2]octane-1-carboxamide 4-tert-Butoxycarbonylamino-N-(4-chlorophenyl)-N-methylbicyclo[2.2.2]octane-1-carboxamide (80.0 mg) was mixed with a 4 mol/L dioxane solution of hydrogen chloride (1.2 mL) and the mixture was stirred at room temperature for 40 minutes. The crystallized product was collected by filtration and was suspended in water (0.8 mL). While the suspension was chilled in an ice bath, a 1 mol/L aqueous solution of sodium hydroxide (0.3 mL) was added and the mixture was extracted with dichloromethane (4×3 mL). The dichloromethane extracts were combined, washed with saturated brine, dried over anhydrous sodium sulfate and concentrated under reduced pressure. This gave 4-amino-N-(4-chlorophenyl)-N-methylbicyclo[2.2.2]octane-1-carboxamide (39.8 mg) as a white solid.

Step 3:

Synthesis of (2S,4S)-1-[[N-[4-[N-(4-chlorophenyl)-N-methylamino]carbonylbicyclo[2.2.2]oct-1-yl]amino]acetyl]-4-fluoropyrrolidine-2-carbonitrile In a similar manner to Example 132, 4-amino-N-(4-chlorophenyl)-N-methylbicyclo[2.2.2]octane-1-carboxamide (30.0 mg) and (2S,4S)-4-fluoropyrrolidine-2-carbonitrile (24.0 mg) were used to obtain (2S,4S)-1-[[N-[4-[N-(4-chlorophenyl)-N-methylamino]carbonylbicyclo[2.2.2]oct-1-yl]amino]acetyl]-4-fluoropyrrolidine-2-carbonitrile (30.4 mg).

MS (FAB$^+$) m/z: 447 (MH$^+$). HRMS (FAB$^+$) for $C_{23}H_{29}ClFN_4O_2$ (MH$^+$): calcd, 447.1963; found, 447.1994.

EXAMPLE 134

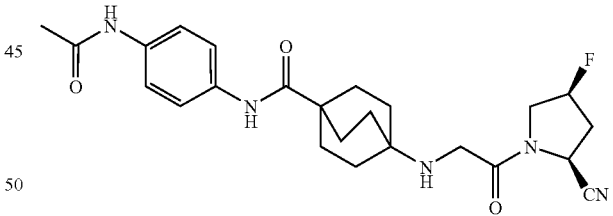

Synthesis of (2S,4S)-1-[[N-[4-[N-(4-acetamidophenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4'-aminoacetanilide (51.0 mg) were used to obtain (2S,4S)-1-[[N-[4-[N-(4-acetamidophenyl)amino]carbonylbicyclo[2.2.2]oct-1-yl]amino]acetyl]-4-fluoropyrrolidine-2-carbonitrile (11.9 mg).

MS (FAB$^+$) m/z: 456 (MH$^+$). HRMS (FAB$^+$) for $C_{24}H_{31}FN_5O_3$ (MH$^+$): calcd, 456.2411; found, 456.2403.

EXAMPLE 135

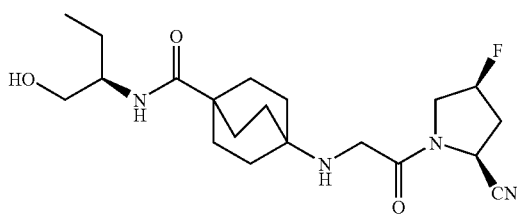

Synthesis of (2S,4S)-4-fluoro-1-[[N-[4-[N-[(2R)-1-hydroxy-2-butyl]amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and (1R)-2-amino-1-butanol (30.1 mg) were used to obtain (2S,4S)-4-fluoro-1-[[N-[4-[N-[(2R)-1-hydroxy-2-butyl]amino]carbonylbicyclo[2.2.2]oct-1-yl]amino]acetyl]pyrrolidine-2-carbonitrile (11.3 mg).

MS (FAB$^+$) m/z: 395 (MH$^+$). HRMS (FAB$^+$) for $C_{20}H_{32}FN_4O_3$ (MH$^+$): calcd, 395.2458; found, 395.2420.

EXAMPLE 136

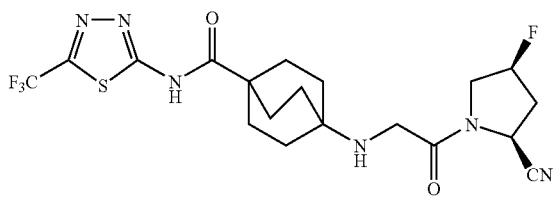

Synthesis of (2S,4S)-4-fluoro-1-[[N-[4-[N-(5-trifluoromethyl-1,3,4-thiadiazol-2-yl)amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-5-trifluoromethyl-1,3,4-thiadiazole (57.5 mg) were used to obtain (2S,4S)-4-fluoro-1-[[N-[4-[N-(5-trifluoromethyl-1,3,4-thiadiazol-2-yl)amino]carbonylbicyclo[2.2.2]oct-1-yl]amino]acetyl]pyrrolidine-2-carbonitrile (12.0 mg).

MS (FAB$^+$) m/z: 475 (MH$^+$). HRMS (FAB$^+$) for $C_{19}H_{23}F_4N_6O_2S$ (MH$^+$): calcd, 475.1539; found, 475.1557.

EXAMPLE 137

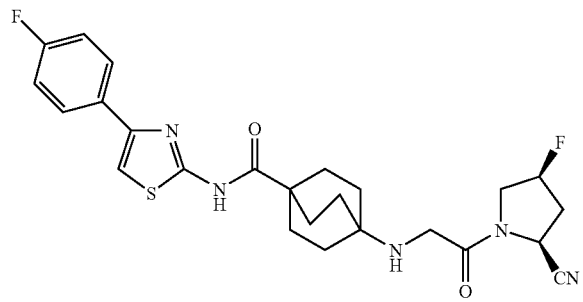

Synthesis of (2S,4S)-4-fluoro-1-[[N-[4-[N-[4-(4-fluorophenyl)thiazol-2-yl]amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-4-(4-fluorophenyl)thiazole (66.1 mg) were used to obtain (2S,4S)-4-fluoro-1-[[N-[4-[N-[4-(4-fluorophenyl)thiazol-2-yl]amino)carbonylbicyclo[2.2.2]oct-1-yl]amino]acetyl]pyrrolidine-2-carbonitrile (50.6 mg).

MS (FAB$^+$) m/z: 500 (MH$^+$). HRMS (FAB$^+$) for $C_{25}H_{28}F_2N_5O_2S$ (MH$^+$): calcd, 500.1932; found, 500.1978.

EXAMPLE 138

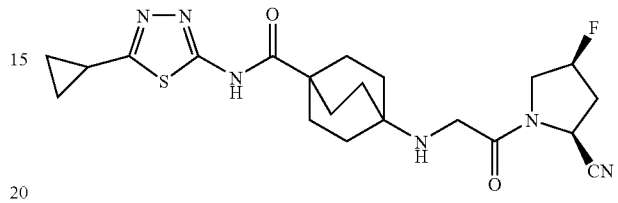

Synthesis of (2S,4S)-1-[[N-[4-[N-(5-cyclopropyl-1,3,4-thiadiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-5-cyclopropyl-1,3,4-thiathiazole (48.0 mg) were used to obtain (2S,4S)-1-[[N-[4-[N-(5-cyclopropyl-1,3,4-thiadiazol-2-yl)amino]carbonylbicyclo[2.2.2]oct-1-yl]amino]acetyl]-4-fluoropyrrolidine-2-carbonitrile (42.2 mg).

MS (FAB$^+$) m/z: 447 (MH$^+$). HRMS (FAB$^+$) for $C_{21}H_{28}FN_6O_2S$ (MH$^+$): calcd, 447.1978; found, 447.2007.

EXAMPLE 139

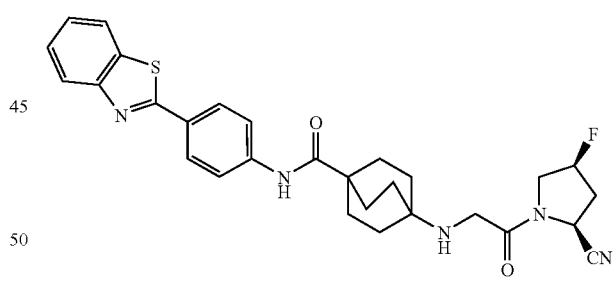

Synthesis of (2S,4S)-1-[[N-[4-[N-[4-(benzothiazol-2-yl)phenyl]amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-(benzothiazol-2-yl)aniline (51.0 mg) were used to obtain (2S,4S)-1-[[N-[4-[N-[4-(benzothiazol-2-yl)phenyl]amino]carbonylbicyclo[2.2.2]oct-1-yl]amino]acetyl]-4-fluoropyrrolidine-2-carbonitrile (10.4 mg).

MS (FAB$^+$) m/z: 532 (MH$^+$). HRMS (FAB$^+$) for $C_{29}H_{31}FN_5O_3S$ (MH$^+$): calcd, 532.2183; found, 532.2158.

EXAMPLE 140

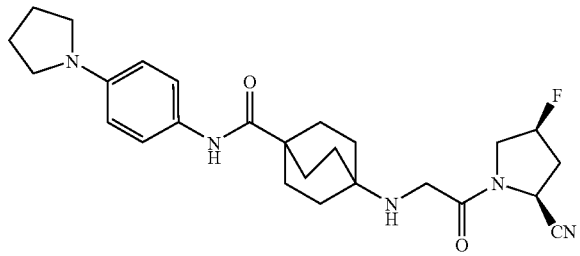

Synthesis of (2S,4S)-1-[[N-[4-[N-[4-(pyrrolidin-1-yl)phenyl]amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-(pyrrolidin-1-yl)aniline (50.2 mg) were used to obtain (2S,4S)-1-[[N-[4-[N-[4-(pyrrolidin-1-yl)phenyl]amino]carbonylbicyclo[2.2.2]oct-1-yl]amino]acetyl]-4-fluoropyrrolidine-2-carbonitrile (13.7 mg).

MS (FAB$^+$) m/z: 468 (MH$^+$). HRMS (FAB$^+$) for $C_{26}H_{35}FN_5O_2$ (MH$^+$): calcd, 468.2775; found, 468.2738.

EXAMPLE 141

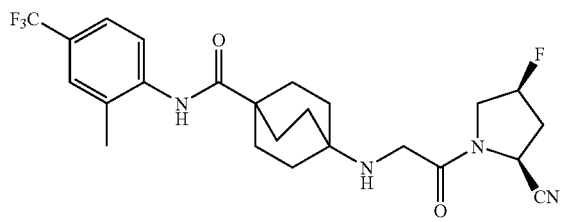

Synthesis of (2S,4S)-4-fluoro-1-[[N-[4-[N-(2-methyl-4-trifluoromethylphenyl)amino]carbonylbicyclo[2.2.2]oct-1-yl]amino]acetyl]pyrrolidine-2-carbonitrile Step 1:

Synthesis of 4-tert-butoxycarbonylamino-N-(2-methyl-4-trifluoromethylphenyl)bicyclo[2.2.2]octane-1-carboxamide In a similar manner to Example 133, 4-tert-butoxycarbonylaminobicyclo[2.2.2]octane-1-carboxylic acid (150 mg) and 2-methyl-4-trifluoromethylaniline (2152 μL) were used to obtain 4-tert-butoxycarbonylamino-N-(2-methyl-4-trifluoromethylphenyl)bicyclo[2.2.2]octane-1-carboxamide (92.5 mg).

MS (FAB$^+$) m/z: 427 (MH$^+$). HRMS (FAB$^+$) for $C_{22}H_{30}F_3N_2O_3$ (MH$^+$): calcd, 427.2209; found, 427.2237.

Step 2:

Synthesis of 4-amino-N-(2-methyl-4-trifluoromethylphenyl)bicyclo[2.2.2]octane-1-carboxamide In a similar manner to Example 133, 4-tert-butoxycarbonylamino-N-(2-methyl-4-trifluoromethylphenyl)bicyclo[2.2.2]octane-1-carboxamide (84.6 mg) was used to obtain 4-amino-N-(2-methyl-4-trifluoromethylphenyl)bicyclo[2.2.2]octane-1-carboxamide (59.8 mg).

MS (FAB$^+$) m/z: 327 (MH$^+$). HRMS (FAB$^+$) for $C_{17}H_{22}F_3N_2O$ (MH$^+$): calcd, 327.1684; found, 327.1711.

Step 3:

Synthesis of (2S,4S)-4-fluoro-1-[[N-[4-[N-(2-methyl-4-trifluoromethylphenyl)amino]carbonylbicyclo[2.2.2]oct-1-yl]amino]acetyl]pyrrolidine-2-carbonitrile In a similar manner to Example 132, 4-amino-N-(2-methyl-4-trifluoromethylphenyl)bicyclo[2.2.2]octane-1-carboxamide (59.8 mg) and (2S,4S)-1-bromoacetyl-4-fluoropyrrolidine-2-carbonitrile (43.1 mg) were used to obtain (2S,4S)-1-[[N-[4-[N-(2-methyl-4-trifluoromethylphenyl)amino]carbonylbicyclo[2.2.2]oct-1-yl]amino]acetyl]-4-fluoropyrrolidine-2-carbonitrile (48.4 mg).

MS (FAB$^+$) m/z: 481 (MH$^+$). HRMS (FAB$^+$) for $C_{24}H_{29}F_4N_4O_2$ (MH$^+$): calcd, 481.2227; found, 481.2247.

EXAMPLE 142

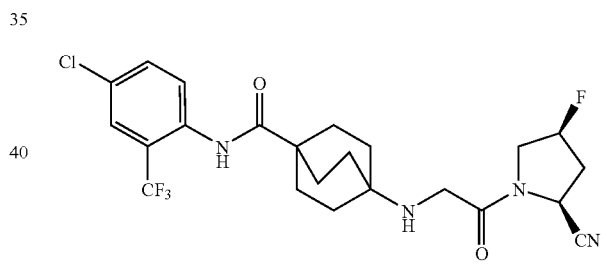

Synthesis of (2S,4S)-1-[[N-[4-[N-(4-chloro-2-trifluoromethylphenyl)amino]carbonylbicyclo[2.2.2]oct-1-yl]amino]acetyl]-4-fluoropyrrolidine-2-carbonitrile Step 1:

Synthesis of 4-tert-butoxycarbonylamino-N-(4-chloro-2-trifluoromethyl-phenyl)bicyclo[2.2.2]octane-1-carboxamide In a similar manner to Example 133, 4-tert-butoxycarbonylaminobicyclo[2.2.2]octane-1-carboxylic acid (150 mg) and 2-amino-5-chlorobenzotrifluoride (173 μL) were used to obtain 4-tert-butoxycarbonylamino-N-(4-chloro-2-trifluoromethylphenyl)bicyclo[2.2.2]octane-1-carboxamide (79.7 mg).

MS (FAB$^+$) m/z: 447 (MH$^+$). HRMS (FAB$^+$) for $C_{21}H_{27}ClF_3N_2O_3$ (MH$^+$): calcd, 447.1662; found, 447.1631.

Step 2:

Synthesis of 4-amino-N-(4-chloro-2-trifluoromethylphenyl)bicyclo[2.2.2]octane-1-carboxamide In a similar manner to Example 133, 4-tert-butoxycarbonylamino-N-(4-chloro-2-trifluoromethylphenyl)bicyclo[2.2.2]octane-1-carboxamide (76.9 mg) was used to obtain 4-amino-N-(2-methyl-4-trifluoromethylphenyl)bicyclo[2.2.2]octane-1-carboxamide (43.0 mg).

MS (FAB$^+$) m/z: 347 (MH$^+$). HRMS (FAB$^+$) for $C_{16}H_{19}ClF_3N_2O$ (MH$^+$): calcd, 347.1138; found, 347.1172.

Step 3:

Synthesis of (2S,4S)-1-[[N-[4-[N-(4-chloro-2-trifluoromethylphenyl)amino]carbonylbicyclo[2.2.2]oct-1-yl]amino]acetyl]-4-fluoropyrrolidine-2-carbonitrile In a similar manner to Example 132, 4-amino-N-(4-chloro-2-trifluoromethylphenyl)bicyclo[2.2.2]octane-1-carboxamide (38.2 mg) and (2S,4S)-1-bromoacetyl-4-fluoropyrrolidine-2-carbonitrile (24.2 mg) were used to obtain (2S,4S)-1-[[N-[4-[N-(4-chloro-2-trifluoromethylphenyl)amino]carbonylbicyclo[2.2.2]oct-1-yl]amino]acetyl]-4-fluoropyrrolidine-2-carbonitrile (21.9 mg).

MS (FAB$^+$) m/z: 501 (MH$^+$). HRMS (FAB$^+$) for $C_{23}H_{26}ClF_4N_4O_2$ (MH$^+$): calcd, 501.1680; found, 501.1662.

EXAMPLE 143

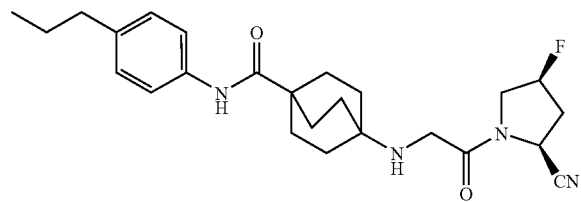

Synthesis of (2S,4S)-4-fluoro-1-[[N-[4-[N-(4-propylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-propylaniline (46.0 mg) were used to obtain (2S,4S)-4-fluoro-1-[[N-[4-[N-(4-propylphenyl)amino]carbonylbicyclo[2.2.2]oct-1-yl]amino]acetyl]pyrrolidine-2-carbonitrile (19.1 mg).

MS (FAB$^+$) m/z: 441 (MH$^+$). HRMS (FAB$^+$) for $C_{25}H_{34}FN_4O_2$ (MH$^+$): calcd, 441.2666; found, 441.2672.

EXAMPLE 144

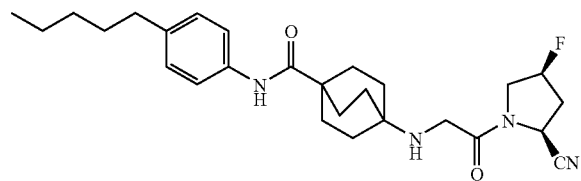

Synthesis of (2S,4S)-4-fluoro-1-[[N-[4-[N-(4-pentylphenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and 4-pentylaniline (55.5 mg) were used to obtain (2S,4S)-4-fluoro-1-[[N-[4-[N-(4-pentylphenyl)amino]carbonylbicyclo[2.2.2]oct-1-yl]amino]acetyl]pyrrolidine-2-carbonitrile (15.7 mg).

MS (FAB$^+$) m/z: 469 (MH$^+$). HRMS (FAB$^+$) for $C_{27}H_{38}FN_4O_2$ (MH$^+$): calcd, 469.2979; found, 49.2977.

EXAMPLE 145

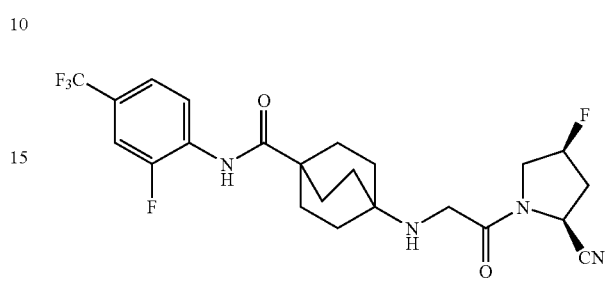

Synthesis of (2S,4S)-4-fluoro-1-[[N-[4-[N-(2-fluoro-4-trifluoromethylphenyl)amino]carbonylbicyclo[2.2.2]oct-1-yl]amino]acetyl]pyrrolidine-2-carbonitrile Step 1:

Synthesis of 4-tert-butoxycarbonylamino-N-(2-fluoro-4-trifluoromethylphenyl)bicyclo[2.2.2]octane-1-carboxamide In a similar manner to Example 133, 4-tert-butoxycarbonylaminobicyclo[2.2.2]octane-1-carboxylic acid (100 mg) and 4-amino-3-fluorobenzotrifluoride (106 μL) were used to obtain 4-tert-butoxycarbonylamino-N-(2-fluoro-4-trifluoromethylphenyl)bicyclo[2.2.2]octane-1-carboxamide (58.6 mg).

MS (FAB$^+$) m/z: 431 (MH$^+$). HRMS (FAB$^+$) for $C_{21}H_{27}F_4N_2O_3$ (MH$^+$): calcd, 431.1958; found, 431.1970.

Step 2:

Synthesis of 4-amino-N-(2-fluoro-4-trifluoromethylphenyl)bicyclo[2.2.2]octane-1-carboxamide In a similar manner to Example 133, 4-tert-butoxycarbonylamino-N-(2-fluoro-4-trifluoromethylphenyl)bicyclo[2.2.2]octane-1-carboxamide (55.0 mg) was used to obtain 4-amino-N-(2-fluoro-4-trifluoromethylphenyl)bicyclo[2.2.2]octane-1-carboxamide (36.2 mg).

Step 3:

Synthesis of (2S,4S)-4-fluoro-1-[[N-[4-[N-(2-fluoro-4-trifluoromethylphenyl)amino]carbonylbicyclo[2.2.2]oct-1-yl]amino]acetyl]pyrrolidine-2-carbonitrile In a similar manner to Example 133, 4-amino-N-(2-fluoro-4-trifluoromethylphenyl)bicyclo[2.2.2]octane-1-carboxamide (33.0 mg) and (2S,4S)-1-bromoacetyl-4-fluoropyrrolidine-2-carbonitrile (23.5 mg) were used to obtain (2S,4S)-4-fluoro-1-[[N-[4-[N-(2-fluoro-4-trifluoromethylphenyl)amino]carbonylbicyclo[2.2.2]oct-1-yl]amino]acetyl]pyrrolidine-2-carbonitrile (19.6 mg).

EXAMPLE 146

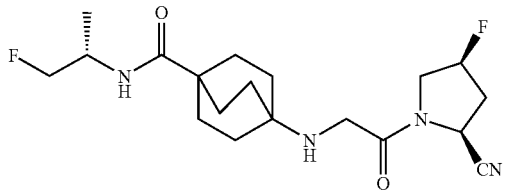

Synthesis of (2S,4S)-4-fluoro-1-[[N-[4-[N-[(2S)-1-fluoro-2-propyl]amino]carbonylbicyclo[2.2.2]oct-1-yl]amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (100 mg) and 1-hydroxybenzotriazole (61.5 mg) were dissolved in dichloromethane (4 mL). While this solution was chilled in an ice bath, 1-(3-dimethylaminopropyl)-3-ethylcarbodiimide hydrochloride (119 mg) was added and the mixture was stirred at room temperature for 1 hour. Subsequently, a mixture of (2S)-1-fluoro-2-propylamine hydrochloride (32.0 mg), triethylamine (56.0 μL) and dichloromethane (2 mL) was added and the resulting mixture was stirred at room temperature for further 8 hours. Following addition of water, the dichloromethane layer was collected. The dichloromethane layer washed with saturated brine, dried over anhydrous sodium sulfate and concentrated under reduced pressure. The resulting residue was purified by a silica gel column (eluant:dichloromethane:methanol=10:1) to give (2S,4S)-4-fluoro-1-[[N-(4-[N-[(2S)-1-fluoro-2-propyl]amino]carbonylbicyclo[2.2.2]oct-1-yl)amino]acetyl]pyrrolidine-2-carbonitrile (34.0 mg) as a white powder.

MS (FAB$^+$) m/z: 383 (MH$^+$). HRMS (FAB$^+$) for $C_{19}H_{29}F_2N_4O_2$ (MH$^+$): calcd, 383.2259; found, 383.2227.

EXAMPLE 147

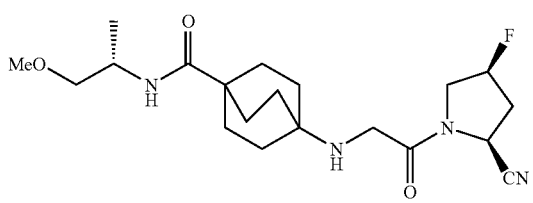

Synthesis of (2S,4S)-4-fluoro-1-[[N-[4-[N-[(2S)-1-methoxy-2-propyl]amino]carbonylbicyclo[2.2.2]oct-1-yl)amino]acetyl]pyrrolidine-2-carbonitrile Step 1:

Synthesis of (2S,4S)-1-[[N-benzyloxycarbonyl-N-[(2S)-1-methoxy-2-propyl]amino]carbonylbicyclo[2.2.2]oct-1-yl]amino]acetyl]-4-fluoropyrrolidine-2-carbonitrile In a similar manner to Example 72, (2S,4S)-1-[[N-benzyloxycarbonyl-N-(4-carboxybicyclo[2.2.2]oct-1-yl)amino]acetyl]-4-fluoropyrrolidine-2-carbonitrile (40.0 mg) and (2S)-1-methoxy-2-propylamine (10.2 mg) were used to obtain (2S,4S)-1-[[N-benzyloxycarbonyl-N-[(2S)-1-methoxy-2-propyl]amino]carbonylbicyclo[2.2.2]oct-1-yl]amino]acetyl]-4-fluoropyrrolidine-2-carbonitrile (47.5 mg).

MS (FAB$^+$) m/z: 529 (MH$^+$).

Step 2:

Synthesis of (2S,4S)-4-fluoro-1-[[N-[4-[N-[(2S)-1-methoxy-2-propyl]amino]carbonylbicyclo[2.2.2]oct-1-yl]amino]acetyl]pyrrolidine-2-carbonitrile In a similar manner to Example 5, (2S,4S)-1-[[N-benzyloxycarbonyl-N-[(2S)-1-methoxy-2-propyl]amino]carbonylbicyclo[2.2.2]oct-1-yl]amino]acetyl]-4-fluoropyrrolidine-2-carbonitrile (34.3 mg) was used to obtain (2S,4S)-4-fluoro-1-[[N-[4-[N-[(2S)-1-methoxy-2-propyl]amino]carbonylbicyclo[2.2.2]oct-1-yl]amino]acetyl]pyrrolidine-2-carbonitrile (11.2 mg).

MS (FAB$^+$) m/z: 395 (MH$^+$). HRMS (FAB$^+$) for $C_{20}H_{32}FN_4O_3$ (MH$^+$): calcd, 395.2458; found, 395.2426.

EXAMPLE 148

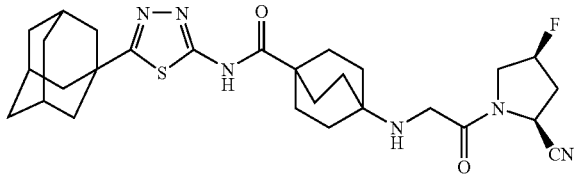

Synthesis of (2S,4S)-1-[[N-[4-[N-(5-adamantyl-1,3,4-thiadiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 5-adamantyl-2-amino-1,3,4-thiadiazole (80.0 mg) were used to obtain (2S,4S)-1-[[N-[4-[N-(5-adamantyl-1,3,4-thiadiazol-2-yl)amino]carbonylbicyclo[2.2.2]oct-1-yl]amino]acetyl]-4-fluoropyrrolidine-2-carbonitrile (56.7 mg).

MS (FAB$^+$) m/z: 541 (MH$^+$). HRMS (FAB$^+$) for $C_{28}H_{38}FN_6O_2S$ (MH$^+$): calcd, 541.2761; found, 541.2782.

EXAMPLE 149

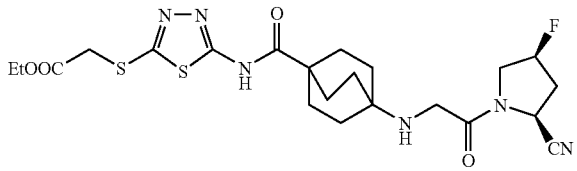

Synthesis of (2S,4S)-1-[[N-[4-[N-(5-ethoxycarbonylmethylthio-1,3,4-thiadiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and ethyl[(5-amino-1,3,4-thiadiazol-2-yl)thio]acetate (74.6 mg) were used to obtain (2S,4S)-1-[[N-[4-[N-(5-ethoxycarbonylmethylthio-1,3,4-thiadiazol-2-yl)amino]carbonylbicyclo[2.2.2]oct-1-yl]amino]acetyl]-4-fluoropyrrolidine-2-carbonitrile (16.4 mg).

MS (FAB$^+$) m/z: 525 (MH$^+$). HRMS (FAB$^+$) for $C_{22}H_{30}FN_6O_4S_2$ (MH$^+$): calcd, 525.1754; found, 525.1771.

EXAMPLE 150

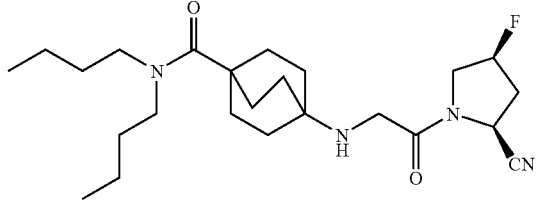

Synthesis of (2S,4S)-1-[[N-[4-(N,N-dibutylamino)carbonylbicyclo[2.2.2]oct-1-yl]amino]acetyl]-4-fluoropyrrolidine-2-carbonitrile Step 1:

Synthesis of 4-benzyloxycarbonylamino-N,N-dibutylbicyclo[2.2.2]octane-1-carboxamide Dibutylamine (94.4 μL) and triethylamine (77.9 μL) were dissolved in dichloromethane (2 mL). While this solution was chilled in a salt/ice bath, 4-benzyloxycarbonylbicyclo[2.2.2]octane-1-carbonyl chloride (150 mg) in dichloromethane (2 mL) was added dropwise and the mixture was stirred for 40 minutes and was concentrated under reduced pressure. Ethyl acetate (30 mL) was then added to the resulting residue and the mixture washed sequentially with water (1.5 mL), a 2 mol/L aqueous sodium hydroxide solution (1.5 mL), water (1.5 mL) and saturated brine (1.5 mL). The mixture was then dried over anhydrous sodium sulfate and concentrated under reduced pressure. Purification of the resulting residue by a silica gel column (eluant:hexane:ethyl acetate=3:1) gave 4-benzyloxycarbonylamino-N,N-dibutylbicyclo[2.2.2]octane-1-carboxamide (171 mg) as a white solid.

MS (FAB$^+$) m/z: 415 (MH$^+$). HRMS (FAB$^+$) for $C_{25}H_{39}N_2O_3$ (MH$^+$): calcd, 415.2961; found, 415.2987.

Step 2:

Synthesis of 4-amino-N,N-dibutylbicyclo[2.2.2]octane-1-carboxamide

In a similar manner to Example 132, 4-benzyloxycarbonylamino-N,N-dibutylbicyclo[2.2.2]octane-1-carboxamide (159 mg) was used to obtain 4-amino-N,N-dibutylbicyclo[2.2.2]octane-1-carboxamide (107 mg).

MS (FAB$^+$) m/z: 281 (MH$^+$). HRMS (FAB$^+$) for $C_{17}H_{33}N_2O$ (MH$^+$): calcd, 281.2593; found, 281.2624.

Step 3:

Synthesis of (2S,4S)-1-[[N-[4-(N,N-dibutylamino)carbonylbicyclo[2.2.2]oct-1-yl]amino]acetyl]-4-fluoropyrrolidine-2-carbonitrile In a similar manner to Example 87, 4-amino-N,N-dibutylbicyclo[2.2.2]octane-1-carboxamide (58.5 mg) and (2S,4S)-4-fluoropyrrolidine-2-carbonitrile (49.0 mg) were used to obtain (2S,4S)-1-bromoacetyl-1-[[N-[4-(N,N-dibutylamino) carbonylbicyclo[2.2.2]oct-1-yl]amino]acetyl]-4-fluoropyrrolidine-2-carbonitrile (18.9 mg).

MS (FAB$^+$) m/z: 435 (MH$^+$). HRMS (FAB$^+$) for $C_{24}H_{40}FN_4O_2$ (MH$^+$): calcd, 435.3135; found, 435.3156.

EXAMPLE 151

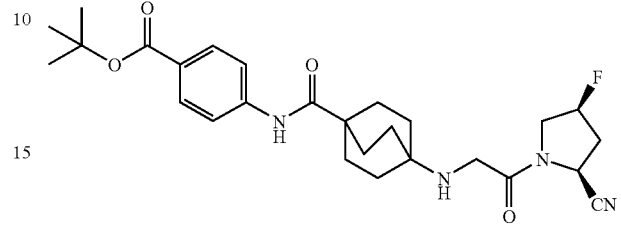

Synthesis of (2S,4S)-4-fluoro-1-[[N-[4-[N-[4-(1,1-dimethylethyloxycarbonyl)phenyl]amino]carbonylbicyclo[2.2.2]oc t-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (120 mg) and 1,1-dimethylethyl 4-aminobenzoate (158 mg) were used to obtain (2S,4S)-4-fluoro-1-[[N-[4-[N-[4-(1,1-dimethylethyloxycarbonyl)phenyl]amino]carbonylbicyclo[2.2.2]oc t-1-yl]amino]acetyl]pyrrolidine-2-carbonitrile (20.1 mg).

MS (FAB$^+$) m/z: 499 (MH$^+$). HRMS (FAB$^+$) for $C_{27}H_{36}FN_4O_4$ (MH$^+$): calcd, 499.2721; found, 499.2721.

EXAMPLE 152

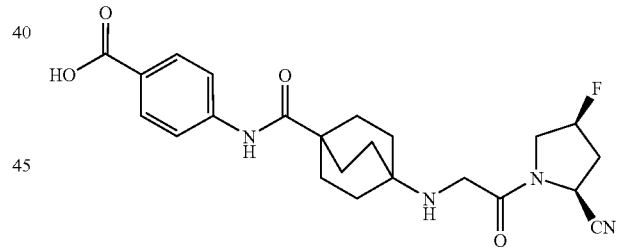

Synthesis of (2S,4S)-4-fluoro-1-[[N-[4-[N-(4-carboxyphenyl)amino]carbonylbicyclo[2.2.2]oct-1-yl]amino]acetyl]pyrrolidine-2-carbonitrile trifluoroacetate (2S,4S)-4-Fluoro-1-[[N-[4-[N-[4-(1,1-dimethylethyloxycarbonyl)phenyl]amino]carbonylbicyclo[2.2.2]oc t-1-yl]amino]acetyl]pyrrolidine-2-carbonitrile (23.0 mg) was dissolved in dichloromethane (0.2 mL). To this solution, trifluoroacetic acid (0.2 mL) was added and the mixture was stirred at room temperature for 1 hour. Subsequently, the reaction mixture was concentrated under reduced pressure to give (2S,4S)-4-fluoro-1-[[N-[4-[N-(4-carboxyphenyl)amino]carbonylbicyclo[2.2.2]oct-1-yl]amino]acetyl]pyrrolidine-2-carbonitrile trifluoroacetate (24.5 mg).

MS (FAB$^+$) m/z: 443 (MH$^+$). HRMS (FAB$^+$) for $C_{23}H_{28}FN_4O_4$ (MH$^+$) calcd, 443.2095; found, 443.2077.

EXAMPLE 153

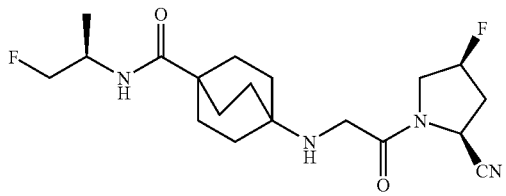

Synthesis of (2S,4S)-4-fluoro-1-[[N-[4-[N-[(2R)-1-fluoro-2-propyl]amino]carbonylbicyclo[2.2.2]oct-1-yl)amino]acetyl]pyrrolidine-2-carbonitrile In a similar manner to Example 146, (2S,4S)-1-[[N-(4-carboxybicyclo[2.2.2]oct-1-yl)amino]acetyl]-4-fluoropyrrolidine-2-carbonitrile (100 mg) and (2R)-1-fluoro-2-propylamine hydrochloride (32.0 mg) were used to obtain (2S,4S)-4-fluoro-1-[[N-(4-[N-[(2R)-1-fluoro-2-propyl]amino]carbonylbicyclo[2.2.2]oct-1-yl)amino]acetyl]pyrrolidine-2-carbonitrile (41.9 mg).

MS (FAB$^+$) m/z: 383 (MH$^+$). HRMS (FAB$^+$) for $C_{19}H_{29}F_2N_4O_2$ (MH$^+$): calcd, 383.2259; found, 383.2229.

EXAMPLE 154

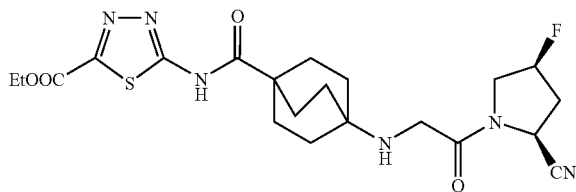

Synthesis of (2S,4S)-1-[[N-[4-[N-(5-ethoxycarbonyl-1,3,4-thiadiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and ethyl (5-amino-1,3,4-thiadiazole-2-carboxylate) (58.9 mg) were used to obtain (2S,4S)-1-[[N-[4-[N-(5-ethoxycarbonyl-1,3,4-thiadiazol-2-yl)amino]carbonylbicyclo[2.2.2]oct-1-yl]amino]acetyl]-4-fluoropyrrolidine-2-carbonitrile (31.9 mg).

MS (FAB$^+$) m/z: 479 (MH$^+$). HRMS (FAB$^+$) for $C_{21}H_{28}FN_6O_4S$ (MH$^+$): calcd, 479.1877; found, 479.1916.

EXAMPLE 155

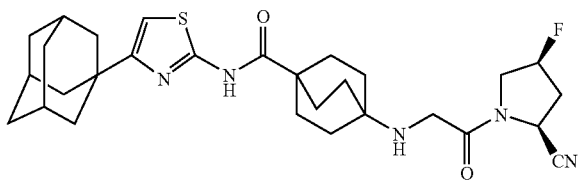

Synthesis of (2S,4S)-1-[[N-[4-[N-(4-adamantylthiazol-2-yl)amino]carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 4-adamantyl-2-aminothiazole (79.7 mg) were used to obtain (2S,4S)-1-[[N-[4-[N-(4-adamantylthiazol-2-yl)amino]carbonylbicyclo[2.2.2]oct-1-yl]amino]acetyl]-4-fluoropyrrolidine-2-carbonitrile (29.5 mg).

MS (FAB$^+$) m/z: 540 (MH$^+$). HRMS (FAB$^+$) for $C_{29}H_{39}FN_5O_2S$ (MH$^+$): calcd, 540.2809; found, 540.2816.

EXAMPLE 156

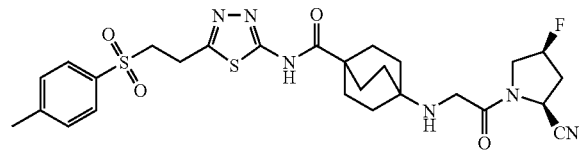

Synthesis of (2S,4S)-4-fluoro-1-[[N-[4-[N-[5-[2-(4-methylphenylsulfonyl)ethyl]-1,3,4-thiadiazol-2-yl]amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-5-[4-methylphenylsulfonyl)ethyl]-1,3,4-thiadiazole (96.4 mg) were used to obtain (2S,4S)-4-fluoro-1-[[N-[4-[N-[5-[2-(4-methylphenylsulfonyl)ethyl]-1,3,4-thiadiazol-2-yl]amino]carbonylbicyclo[2.2.2]oct-1-yl]amino]acetyl]pyrrolidine-2-carbonitrile (30.6 mg).

MS (FAB$^+$) m/z: 589 (MH$^+$). HRMS (FAB$^+$) for $C_{27}H_{34}FN_6O_4S_2$ (MH$^+$): calcd, 589.2067; found, 589.2081.

EXAMPLE 157

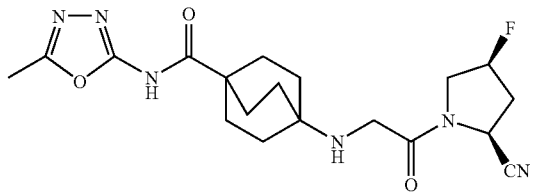

Synthesis of (2S,4S)-4-fluoro-1-[[N-[4-[N-(5-methyl-1,3,4-oxadiazol-2-yl)amino]carbonylbicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-amino-5-methyl-1,3,4-oxadiazole (33.7 mg) were used to obtain (2S,4S)-4-fluoro-1-[[N-[4-[N-(5-methyl-1,3,4-oxadiazol-2-yl)amino]carbonylbicyclo[2.2.2]oct-1-yl]amino]acetyl]pyrrolidine-2-carbonitrile (14.5 mg).

MS (FAB$^+$) m/z: 405 (MH$^+$). HRMS (FAB$^+$) for $C_{19}H_{26}FN_6O_3$ (MH$^+$): calcd, 405.2050; found, 405.2075.

EXAMPLE 158

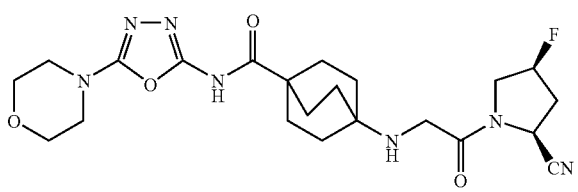

Synthesis of (2S,4S)-4-fluoro-1-[[N-[4-[N-[5-(4-morpholinyl)-1,3,4-oxadiazol-2-yl]amino]carbonyl-bicyclo[2.2.2]oct-1-yl]amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 4-(2-amino-1,3,4-oxadiazole-5-yl)morpholine (57.9 mg) were used to obtain (2S,4S)-4-fluoro-1-[[N-[4-[N-[5-(4-morpholinyl)-1,3,4-oxadiazol-2-yl]amino]carbonylbicyclo[2.2.2]oct-1-yl]amino]acetyl]pyrrolidine-2-carbonitrile (10.1 mg).

MS (FAB$^+$) m/z: 476 (MH$^+$). HRMS (FAB$^+$) for $C_{22}H_{31}FN_7O_4$ (MH$^+$): calcd, 476.2422; found, 476.2456.

EXAMPLE 159

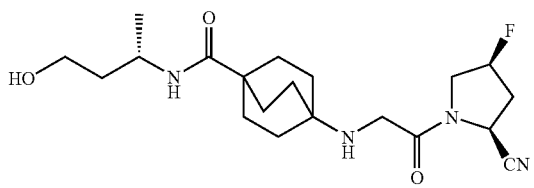

Synthesis of (2S,4S)-4-fluoro-1-[[N-[4-[N-[(2S)-4-hydroxy-2-butyl]amino]carbonylbicyclo[2.2.2]oct-1-yl)amino]acetyl]pyrrolidine-2-carbonitrile In a similar manner to Example 146, ((2S,4S)-1-[[N-(4-carboxybicyclo[2.2.2]oct-1-yl)amino]acetyl]-4-fluoropyrrolidine-2-carbonitrile (100 mg) and (2S)-3-aminobutanol hydrochloride (39.0 mg) were used to obtain (2S,4S)-4-fluoro-1-[[N-[4-[N-[(2S)-4-hydroxy-2-butyl]amino]carbonylbicyclo[2.2.2]oct-1-yl]amino]acetyl]pyrrolidine-2-carbonitrile (20.8 mg).

MS (FAB$^+$) m/z: 395 (MH$^+$). HRMS (FAB$^+$) for $C_{20}H_{32}FN_4O_3$ (MH$^+$): calcd, 395.2458; found, 395.2462.

EXAMPLE 160

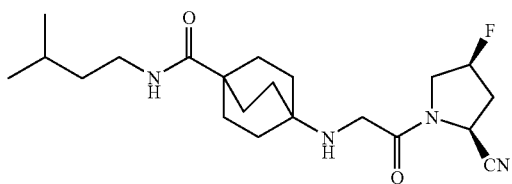

Synthesis of (2S,4S)-4-fluoro-1-[[N-[4-[N-(3-methylbutyl)amino]carbonylbicyclo[2.2.2]oct-1-yl)amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and isoamylamine (39.5 μL) were used to obtain (2S,4S)-4-fluoro-1-[[N-[4-[N-(3-methylbutyl)amino]carbonylbicyclo[2.2.2]oct-1-yl]amino]acetyl]pyrrolidine-2-carbonitrile (22.3 mg).

MS (FAB$^+$) m/z: 393 (MH$^+$). HRMS (FAB$^+$) for $C_{21}H_{34}FN_4O_2$ (MH$^+$): calcd, 393.2666; found, 393.2679.

EXAMPLE 161

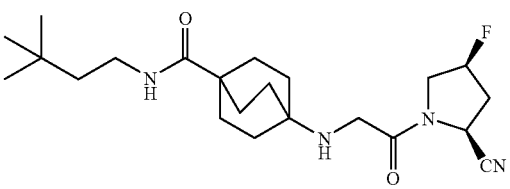

Synthesis of (2S,4S)-4-fluoro-1-[[N-[4-[N-(3,3-dimethylbutyl)amino]carbonylbicyclo[2.2.2]oct-1-yl)amino]acetyl]pyrrolidine-2-carbonitrile In a similar manner to Example 87, (2S,4S)-1-[[N-[4-carboxybicyclo[2.2.2]oct-1-yl)amino]acetyl]-4-fluoropyrrolidine-2-carbonitrile (50.0 mg) and 3,3-dimethylbutylamine (45.8 μL) were used to obtain (2S,4S)-4-fluoro-1-[[N-[4-[N-(3,3-dimethylbutyl)amino]carbonylbicyclo[2.2.2]oct-1-yl]amino]acetyl]pyrrolidine-2-carbonitrile (24.6 mg).

MS (FAB$^+$) m/z: 407 (MH$^+$). HRMS (FAB$^+$) for $C_{22}H_{36}FN_4O_2$ (MH$^+$): calcd, 407.2822; found, 407.2779.

EXAMPLE 162

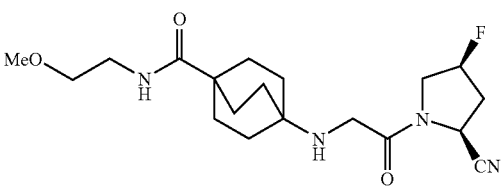

Synthesis of (2S,4S)-4-fluoro-1-[[N-[4-[N-(2-methoxyethyl)amino]carbonylbicyclo[2.2.2]oct-1-yl)amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 2-methoxyethylamine (29.6 μL) were used to obtain (2S,4S)-4-fluoro-1-[[N-[4-[N-(2-methoxyethyl)amino]carbonylbicyclo[2.2.2]oct-1-yl]amino]acetyl]pyrrolidine-2-carbonitrile (31.2 mg).

MS (FAB$^+$) m/z: 381 (MH$^+$). HRMS (FAB$^+$) for $C_{19}H_{30}FN_4O_3$ (MH$^+$): calcd, 381.2302; found, 381.2306.

EXAMPLE 163

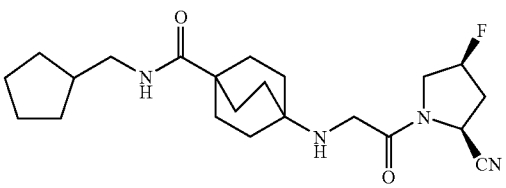

Synthesis of (2S,4S)-1-[[N-[4-(N-cyclopentylmethylamino)carbonylbicyclo[2.2.2]oct-1-yl]amino]acetyl]-4-fluoropyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (70.0 mg) and cyclopentylmethylamine hydrochloride (72.2 mg) were used to obtain (2S,4S)-1-[[N-[4-(N-cyclopentylmethylamino)carbonylbicyclo[2.2.2]oct-1-yl]amino]acetyl]-4-fluoropyrrolidine-2-carbonitrile (19.4 mg).

MS (FAB$^+$) m/z: 405 (MH$^+$). HRMS (FAB$^+$) for $C_{22}H_{34}FN_4O_2$ (MH$^+$): calcd, 405.2666; found, 405.2698.

EXAMPLE 164

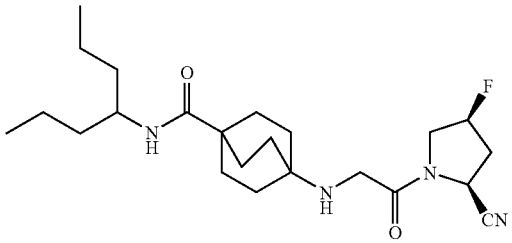

Synthesis of (2S,4S)-4-fluoro-1-[[N-[4-[N-(4-heptyl)amino]carbonylbicyclo[2.2.2]oct-1-yl)amino]acetyl]pyrrolidine-2-carbonitrile In a similar manner to Example 87, (2S,4S)-1-[[N-(4-carboxybicyclo[2.2.2]oct-1-yl)amino]acetyl]-4-fluoropyrrolidine-2-carbonitrile (50.0 mg) and 4-heptylamine (50.9 μL) were used to obtain (2S,4S)-4-fluoro-1-[[N-[4-[N-(4-heptyl)amino]carbonylbicyclo[2.2.2]oct-1-yl]amino]acetyl]pyrrolidine-2-carbonitrile (36.4 mg).

MS (FAB$^+$) m/z: 421 (MH$^+$). HRMS (FAB$^+$) for $C_{23}H_{38}FN_4O_2$ (MH$^+$): calcd, 421.2979; found, 421.2968.

EXAMPLE 165

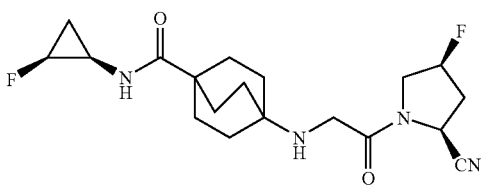

Synthesis of (2S,4S)-4-fluoro-1-[[N-[4-[N-[(1R,2S)-2-fluoro-1-cyclopropyl]amino]carbonylbicyclo[2.2.2]oct-1-yl]amino]acetyl]pyrrolidine-2-carbonitrile Step 1:

Synthesis of 4-benzyloxycarbonylamino-N-[(1R,2S)-2-fluoro-1-cyclopropyl]bicyclo[2.2.2]octane-1-carboxamide In a similar manner to Example 150, 4-benzyloxycarbonylbicyclo[2.2.2]octane-1-carbonyl chloride (200 mg) and (1R,2S)-2-fluoro-1-cyclopropylamine p-toluene sulfonate (184 mg) were used to obtain 4-benzyloxycarbonylamino-N-[(1R,2S)-2-fluoro-1-cyclopropyl]bicyclo[2.2.2]octane-1-carboxamide (189 mg).

Step 2:

Synthesis of 4-amino-N-[(1R,2S)-2-fluoro-1-cyclopropyl]bicyclo[2.2.2]octane-1-carboxamide In a similar manner to Example 132, 4-benzyloxycarbonylamino-N-[(1R,2S)-2-fluoro-1-cyclopropyl]bicyclo[2.2.2]octane-1-carboxamide (189 mg) was used to obtain 4-amino-N-[(1R,2S)-2-fluoro-1-cyclopropyl]bicyclo[2.2.2]octane-1-carboxamide (59.1 mg).

Step 3:

Synthesis of (2S,4S)-4-fluoro-1-[[N-[4-[N-[(1R,2S)-2-fluoro-1-cyclopropyl]amino]carbonylbicyclo[2.2.2]oct-1-yl]amino]acetyl]pyrrolidine-2-carbonitrile In a similar manner to Example 87, 4-amino-N-[(1R,2S)-2-fluoro-1-cyclopropyl]bicyclo[2.2.2]octane-1-carboxamide (47.5 mg) and (2S,4S)-1-bromoacetyl-4-fluoropyrrolidine-2-carbonitrile (49.3 mg) were used to obtain (2S,4S)-4-fluoro-1-[[N-[4-[N-[(1R,2S)-2-fluoro-1-cyclopropyl]amino]carbonylbicyclo[2.2.2]oct-1-yl]amino]acetyl]pyrrolidine-2-carbonitrile (34.6 mg).

MS (FAB$^+$) m/z: 381 (MH$^+$). HRMS (FAB$^+$) for $C_{19}H_{27}F_2N_4O_2$ (MH$^+$): calcd, 381.2102; found, 381.2128.

EXAMPLE 166

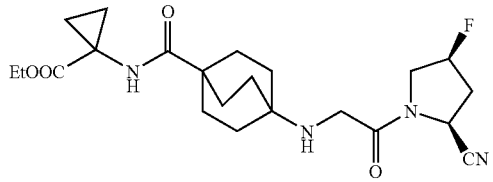

Synthesis of (2S,4S)-1-[[N-[4-[N-(1-ethoxycarbonyl-1-cyclopropyl)amino]carbonylbicyclo[2.2.2]oct-1-yl]amino]acetyl]-4-fluoropyrrolidine-2-carbonitrile Step 1:

Synthesis of 4-benzyloxycarbonylamino-N-(1-ethoxycarbonyl-1-cyclopropyl)bicyclo[2.2.2]octane-1-carboxamide In a similar manner to Example 150, 4-benzyloxycarbonylbicyclo[2.2.2]octane-1-carbonyl chloride (200 mg) and ethyl 1-amino-1-cyclopropylcarboxylate hydrochloride (123 mg) were used to obtain 4-benzyloxycarbonylamino-N-[(1R,2S)-1-ethoxycarbonyl-1-cyclopropyl]bicyclo[2.2.2]octane-1-carboxamide (217 mg).

Step 2:

Synthesis of 4-amino-N-(1-ethoxycarbonyl-1-cyclopropyl)bicyclo[2.2.2]octane-1-carboxamide In a similar manner to Example 132, 4-benzyloxycarbonylamino-N-[(1R,2S)-1-ethoxycarbonyl-1-cyclopropyl]bicyclo[2.2.2]octane-1-carboxamide (205 mg) was used to obtain 4-amino-N-(1-ethoxycarbonyl-1-cyclopropyl)bicyclo[2.2.2]octane-1-carboxamide (124 mg).

MS (FAB⁺) m/z: 281 (MH⁺). HRMS (FAB⁺) for $C_{15}H_{25}N_2O_3$ (MH⁺): calcd, 281.1865; found, 281.1856.

Step 3:

Synthesis of (2S,4S)-1-[[N-[4-[N-(1-ethoxycarbonyl-1-cyclopropyl)amino]carbonylbicyclo[2.2.2]oct-1-yl]amino]acetyl]-4-fluoropyrrolidine-2-carbonitrile In a similar manner to Example 87, 4-amino-N-(1-ethoxycarbonyl-1-cyclopropyl)bicyclo[2.2.2]octane-1-carboxamide (62.6 mg) and (2S,4S)-1-bromoacetyl-4-fluoropyrrolidine-2-carbonitrile (52.5 mg) were used to obtain (2S,4S)-1-[[N-[4-[N-(1-ethoxycarbonyl-1-cyclopropyl)amino]carbonylbicyclo[2.2.2]oct-1-yl]amino]acetyl]-4-fluoropyrrolidine-2-carbonitrile (20.2 mg).

MS (FAB⁺) m/z: 435 (MH⁺). HRMS (FAB⁺) for $C_{22}H_{32}FN_4O_4$ (MH⁺): calcd, 435.2408; found, 435.2408.

EXAMPLE 167

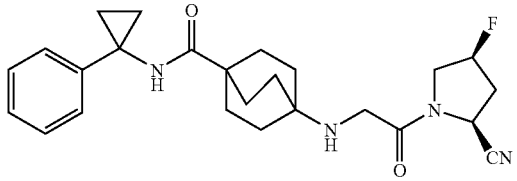

Synthesis of (2S,4S)-4-fluoro-1-[[N-[4-[N-(1-phenyl-1-cyclopropyl)amino]carbonylbicyclo[2.2.2]oct-1-yl]amino]acetyl]pyrrolidine-2-carbonitrile Step 1:

Synthesis of 4-benzyloxycarbonylamino-N-(1-phenyl-1-cyclopropyl)bicyclo[2.2.2]octane-1-carboxamide In a similar manner to Example 150, 4-benzyloxycarbonylbicyclo[2.2.2]octane-1-carbonyl chloride (480 mg) and 1-phenyl-1-cyclopropylamine (99.3 mg) were used to obtain 4-benzyloxycarbonylamino-N-(1-phenyl-1-cyclopropyl)bicyclo[2.2.2]octane-1-carboxamide (255 mg).

MS (FAB⁺) m/z: 419 (MH⁺). HRMS (FAB⁺) for $C_{26}H_{31}N_2O_3$ (MH⁺): calcd, 419.2335; found, 419.2345.

Step 2:

Synthesis of 4-amino-N-(1-phenyl-1-cyclopropyl)bicyclo[2.2.2]octane-1-carboxamide In a similar manner to Example 132, 4-benzyloxycarbonylamino-N-(1-phenyl-1-cyclopropyl)bicyclo[2.2.2]octane-1-carboxamide (255 mg) was used to obtain 4-amino-N-(1-phenyl-1-cyclopropyl)bicyclo[2.2.2]octane-1-carboxamide (118 mg).

MS (FAB⁺) m/z: 285 (MH⁺). HRMS (FAB⁺) for $C_{18}H_{25}N_2O$ (MH⁺): calcd, 285.1967; found, 285.1982.

Step 3:

Synthesis of (2S,4S)-4-fluoro-1-[[N-[4-[N-(1-phenyl-1-cyclopropyl)amino]carbonylbicyclo[2.2.2]oct-1-yl]amino]acetyl]pyrrolidine-2-carbonitrile In a similar manner to Example 87, 4-amino-N-(1-phenyl-1-cyclopropyl)bicyclo[2.2.2]octane-1-carboxamide (50.0 mg) and (2S,4S)-1-bromoacetyl-4-fluoropyrrolidine-2-carbonitrile (41.9 mg) were used to obtain (2S,4S)-4-fluoro-1-[[N-[4-[N-(1-phenyl-1-cyclopropyl)amino]carbonylbicyclo[2.2.2]oct-1-yl]amino]acetyl]pyrrolidine-2-carbonitrile (38.1 mg).

MS (FAB⁺) m/z: 439 (MH⁺). HRMS (FAB⁺) for $C_{25}H_{32}FN_4O_2$ (MH⁺): calcd, 439.2509; found, 439.2512.

EXAMPLE 168

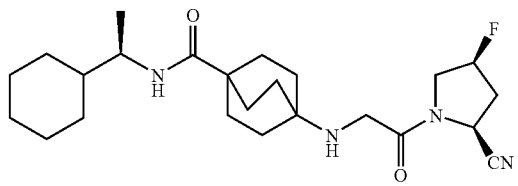

Synthesis of (2S,4S)-1-[[N-(4-[-N-[(1R)-1-cyclohexylethyl]amino]carbonylbicyclo[2.2.2]oct-1-yl)amino]acetyl]-4-fluoropyrrolidine-2-carbonitrile In a similar manner to Example 63, (2S,4S)-1-[[N-[4-carboxybicyclo[2.2.2]oct-1-yl]amino]acetyl]-4-fluoropyrrolidine-2-carbonitrile (50.0 mg) and (1R)-1-cyclohexylethylamine (49.7 μL) were used to obtain (2S,4S)-1-[[N-(4-[-N-[(1R)-1-cyclohexylethyl]amino]carbonylbicyclo[2.2.2]oct-1-yl)amino]acetyl]-4-fluoropyrrolidine-2-carbonitrile (29.9 mg).

MS (FAB⁺) m/z: 433 (MH⁺). HRMS (FAB⁺) for $C_{24}H_{38}FN_4O_2$ (MH⁺): calcd, 433.2979; found, 433.2996.

EXAMPLE 169

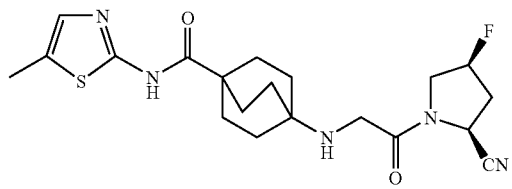

Synthesis of (2S,4S)-4-fluoro-1-[[N-[4-[N-(3-methylthiazol-2-yl)amino]carbonylbicyclo[2.2.2]oct-1-yl]amino]acetyl]pyrrolidine-2-carbonitrile In a similar manner to Example 63, (2S,4S)-1-[[N-[4-carboxybicyclo[2.2.2]oct-1-yl]amino]acetyl]-4-fluoropyrrolidine-2-carbonitrile (50.0 mg) and 2-amino-5-methylthiazole (38.8 mg) were used to obtain (2S,4S)-4-fluoro-1-[[N-[4-[N-(3-methylthiazol-2-yl)amino]carbonylbicyclo[2.2.2]oct-1-yl]amino]acetyl]pyrrolidine-2-carbonitrile (9.5 mg).

MS (FAB+) m/z: 420 (MH+). HRMS (FAB+) for $C_{20}H_{27}FN_5O_2S$ (MH+): calcd, 420.1870; found, 420.1874.

EXAMPLE 170

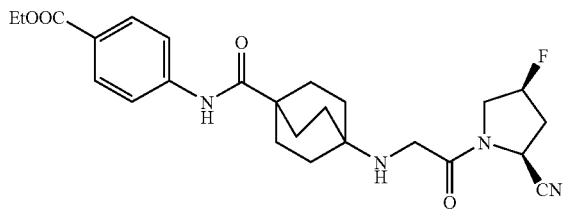

Synthesis of (2S,4S)-1-[[N-[4-[N-(4-ethoxycarbonylphenyl)amino]carbonylbicyclo[2.2.2]oct-1-yl]amino]acetyl]-4-fluoropyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (50.0 mg) and ethyl 4-aminobenzoate (56.0 mg) were used to obtain (2S,4S)-1-[[N-[4-[N-(4-ethoxycarbonylphenyl)amino]carbonylbicyclo[2.2.2]oct-1-yl]amino]acetyl]-4-fluoropyrrolidine-2-carbonitrile (24.9 mg).

MS (FAB+) m/z: 471 (MH+). HRMS (FAB+) for $C_{25}H_{32}FN_4O_4$ (MH+): calcd, 471.2408; found, 471.2412.

EXAMPLE 171

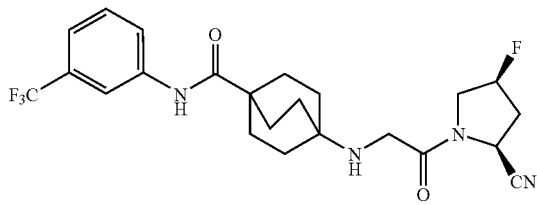

Synthesis of (2S,4S)-4-fluoro-1-[[N-[4-[N-(3-trifluorophenyl)amino]carbonylbicyclo[2.2.2]oct-1-yl]amino]acetyl]pyrrolidine-2-carbonitrile In a similar manner to Example 63, (2S,4S)-1-[[N-(4-carboxybicyclo[2.2.2]oct-1-yl)amino]acetyl]-4-fluoropyrrolidine-2-carbonitrile (80.0 mg) and 3-aminobenzotrifluoride (92.0 mg) were used to obtain (2S,4S)-4-fluoro-1-[[N-[4-[N-(3-trifluorophenyl)amino]carbonylbicyclo[2.2.2]oct-1-yl]amino]acetyl]pyrrolidine-2-carbonitrile (23.2 mg).

MS (FAB+) m/z: 467 (MH+). HRMS (FAB+) for $C_{23}H_{27}F_4N_4O_2$ (MH+): calcd, 467.2070; found, 467.2087.

TEST EXAMPLE 1

Test for the Ability of the Compounds of the Invention to Inhibit of Dipeptidylpeptidase IV Activity The concentration of free 7-amino-4-methyl-coumarin (AMC) generated by hydrolysis of H-Gly-Pro-AMC.HBr substrate by plasma dipeptidylpeptidase IV was determined by fluorometry.

Method

A 20 μL of buffer (25 mmol/L hepes, 140 mmol/L sodium chloride, 1% bovine serum albumin, 80 mmol/L magnesium chloride hexahydrate, pH 7.4) containing each compound was added to 20 μL of plasma diluted 8-fold with saline in a well of a 96-well flat bottom plate. The plate was left at room temperature for 5 minutes and 10 μL of 0.1 mmol/L H-Gly-Pro-AMC.HBr solution was added to each well to initiate the reaction. The plate was left in a dark environment at room temperature for 20 minutes, at which point 20 μL 25% acetic acid was added to terminate the reaction. Using a fluorescent plate reader, the free AMC concentration was determined by exciting the samples at 355 nm and measuring the fluorescence intensity at 460 nm. Using Prism 3.02 (GraphPad Software), the results were analyzed to determine the 50% inhibitory concentration (IC50). The results are shown in Table 1.

TABLE 1

| In vitro dipeptidylpeptidase IV inhibition | |
|---|---|
| Test compound | IC50 (nmol/L) |
| Example 1 | 0.89 |
| Example 8 | 0.83 |
| Example 16 | 0.082 |
| Example 52 | 0.057 |
| Compound A | 3.3 |

Compound A: (2S)-1-[[(3-hydroxy-1-adamantyl)amino]acetyl]-2-cyanopyrrolidine (LAF-237)

TEST EXAMPLE 2

Test for the Inhibition of Dipeptidylpeptidase IV Activity in Mice by Oral Administration of the Compounds of the Invention Each compound was suspended in 0.3% sodium carboxymethylcellulose to a concentration of 0.1 mg/mL. The preparation was orally administered to 8-week old male ICR mice (Charles River Laboratories Japan) at a dose of 10 mL/kg. Using an EDTA 2K-treated capillary tube, blood samples were collected from the tail vein before administration and 30 minutes after administration. The blood samples were centrifuged at 6000 rpm for 2 minutes to separate plasma. The enzymatic activity was determined using the same procedure as in Test Example 1. The inhibition was determined from the decrease in the enzymatic activity from the initial activity (% inhibition={(activity before administration−activity after administration)/(activity before administration)}×100). The results are shown in Table 2.

TABLE 2

| Inhibition of plasma dipeptidylpeptidase IV activity in mice by oral administration | |
|---|---|
| Test compound | % inhibition |
| Example 1 | 71 |
| Example 9 | 87 |
| Example 15 | 66 |
| Example 30 | 77 |
| Example 52 | 70 |
| Compound A | 81 |

Compound A: (2S)-1-[[(3-hydroxy-1-adamantyl)amino]acetyl]-2-cyanopyrrolidine (LAF-237)

TEST EXAMPLE 3

Oral Glucose Tolerance Test in Mice

The compound of the present invention of Example 58 was suspended in 0.3% sodium carboxymethylcellulose (CMC-Na, Sigma). Seven weeks old male ICR mice (Charles River Laboratories Japan) were acclimatized for 1 week. During the acclimatization period, the animals were allowed to freely consume standard feed (CE-2, Clea Japan) and water. The ICR mice reaching 8-weeks old were fasted for 16 hours. Subsequently, the animals were orally administered 0.3% CMC-Na (10 mL/kg) or Compound 1 (1 mg/kg, 10 mL/kg) and were immediately administered a glucose solution orally at a dose of 5 g/kg. Using an EDTA 2K-treated capillary tube, blood samples were collected from the tail vein before administration of glucose solution and 15, 30, 60, and 120 minutes after administration. The blood glucose level was determined using glucose B-test Wako (Wako Pure Chemical Industries). The results were shown in means ± standard errors. Statistical analysis was performed using t-test with a significant level of less than 5%. The results are shown in FIG. 1.

TEST EXAMPLE 4

Test for the Efficacy of the Compounds of the Invention Against Drug-Induced Hypoleukocytosis The efficacy of the compounds of the present invention against drug-induced hypoleukocytosis was evaluated by conducting an experiment according to the method described by Okabe et al (Japanese Pharmacology and Therapeutics, Vol. 19, No. 6 (1991): p 55).

Eight weeks old male ICR mice (Charles River Laboratories Japan) were intraperitoneally administered a single dose of cyclophosphamide (200 mg/kg) on Day 0. Starting from the following day, control group was given saline and test group was orally administered the compound of the present invention (1 to 200 mg/kg) once or twice a day over a five day period. Blood samples were collected 2, 4, 6, and 8 days after the beginning of the test and the white blood cell count was monitored over time. The white blood cell count of the test group at a given time was compared with the white blood cell count before administration of cyclophosphamide to evaluate the efficacy of the compound of the present invention against the drug-induced hypoleukocytosis. The results indicate that the decrease in the white blood cell count is significantly suppressed in the group administered the compound of the present invention as compared to control group.

TEST EXAMPLE 5

Test for the Ability of the Compounds of the Invention to Increase the Blood G-CSF Level Seven weeks old male ICR mice (Charles River Laboratories Japan) were used. Control group was given saline and test group was orally administered the compound of the present invention (1 to 200 mg/kg) once or twice a day over a five day period. Mice were anesthetized on the day following the cessation of administration and blood samples were collected. Plasma G-CSF level was determined using mouse G-CSF ELISA kit (R&D SYSTEM). The results indicate that the plasma G-CSF level was significantly increased in the group administered the compound of the present invention as compared to control group.

INDUSTRIAL APPLICABILITY

As set forth, the compounds of the present invention are novel bicycloamide derivatives and pharmaceutically acceptable salts thereof that effectively inhibit DPP-IV. Pharmaceutical compositions that contain the present compound as an active ingredient are useful in the prevention and/or treatment of diabetes and associated diabetic complications, as well as in the prevention and/or treatment of other diseases that involve DPP-IV.

What is claimed is:

1. A bicycloamide derivative represented by the following general formula (1):

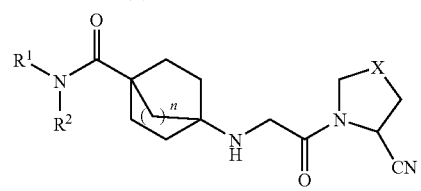

(1)

wherein $R^1$ and $R^2$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^3R^4$ (wherein $R^3$ and $R^4$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^3$ and $R^4$ may together form a ring structure), or $R^1$ and $R^2$ may together form a ring structure; X is $CH_2$, CHF, $CF_2$, CHOH, S or O; and n is 1, 2 or 3, or a pharmaceutically acceptable salt thereof.

2. The bicycloamide derivative according to claim 1, represented by the following general formula (2):

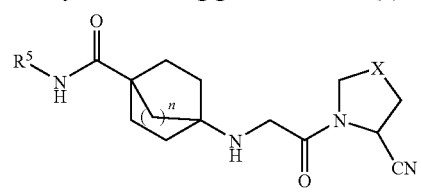

(2)

wherein $R^5$ is a substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^3R^4$ (wherein $R^3$ and $R^4$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^3$ and $R^4$ may together form a ring structure); X is $CH_2$, CHF, $CF_2$, CHOH, S or O; and n is 1, 2 or 3, or a pharmaceutically acceptable salt thereof.

3. The bicycloamide derivative according to claim 1, represented by the following general formula (3):

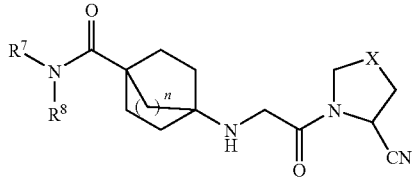

(3)

wherein $R^7$ and $R^8$ may or may not be identical to one another and are each independently a substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^3R^4$ (wherein $R^3$ and $R^4$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^3$ and $R^4$ may together form a ring structure), or $R^7$ and $R^8$ may together form a ring structure; X is $CH_2$, CHF, $CF_2$, CHOH, S or O; and n is 1, 2 or 3, or a pharmaceutically acceptable salt thereof.

4. An intermediate in the production of the bicycloamide derivative of claim 1, represented by the following formula (4):

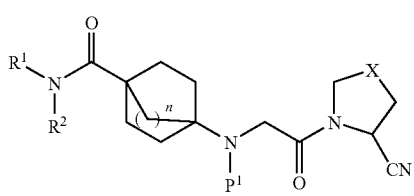

(4)

wherein $R^1$ and $R^2$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted arylethyl group, substituted or unsubstituted aromatic hydrocarbon group, substituted or unsubstituted aromatic heterocyclic ring, substituted or unsubstituted aliphatic heterocyclic ring or $NR^4R^5$ (wherein $R^4$ and $R^5$ may or may not be identical to one another and are each independently a hydrogen atom, substituted or unsubstituted $C_1$ to $C_6$ alkyl group, substituted or unsubstituted $C_3$ to $C_6$ cycloalkyl group, substituted or unsubstituted arylmethyl group, substituted or unsubstituted aromatic hydrocarbon group, substituted or unsubstituted aromatic heterocyclic ring or substituted or unsubstituted aliphatic heterocyclic ring, or $R^4$ and $R^5$ may together form a ring structure), or $R^1$ and $R^2$ may together form a ring structure; X is $CH_2$, CHF, $CF_2$, CHOH, S or O; n is 1, 2 or 3; and $P^1$ is an amino-protecting group.

5. A pharmaceutical composition, containing as an active ingredient the bicycloamide derivative according to claim 1 or a pharmaceutically acceptable salt thereof, and a pharmaceutically acceptable auxiliary agent.

6. A DPP-IV inhibitor, containing as an active ingredient the bicycloamide derivative according to claim 1 or a pharmaceutically acceptable salt thereof, and a pharmaceutically acceptable auxiliary agent.

7. A therapeutic agent for treating type II diabetes, containing as an active ingredient the bicycloamide derivative according to claim 1 or a pharmaceutically acceptable salt thereof, and a pharmaceutically acceptable auxiliary agent.

8. A method of treating type II diabetes, which comprises administering to a patient in need of said treatment a therapeutically effective amount of the bicycloamide derivative according to claim 1 or a pharmaceutically acceptable salt thereof.

* * * * *